(12) United States Patent
Andersen

(10) Patent No.: US 12,234,288 B2
(45) Date of Patent: Feb. 25, 2025

(54) IMMUNOGENIC ARGINASE 2 POLYPEPTIDES

(71) Applicant: IO Biotech ApS, Copenhagen (DK)

(72) Inventor: Mads Hald Andersen, Nærum (DK)

(73) Assignee: IO Biotech ApS, Copenhagen (DK)

( * ) Notice: Subject to any disclaimer, the term of this patent is extended or adjusted under 35 U.S.C. 154(b) by 886 days.

(21) Appl. No.: 17/293,325

(22) PCT Filed: Nov. 14, 2019

(86) PCT No.: PCT/EP2019/081369
§ 371 (c)(1),
(2) Date: May 12, 2021

(87) PCT Pub. No.: WO2020/099582
PCT Pub. Date: May 22, 2020

(65) Prior Publication Data
US 2021/0403566 A1 Dec. 30, 2021

(30) Foreign Application Priority Data
Nov. 14, 2018 (GB) ..................................... 1818576

(51) Int. Cl.
*C07K 16/28* (2006.01)
*A61K 39/00* (2006.01)
(Continued)

(52) U.S. Cl.
CPC .. *C07K 16/2818* (2013.01); *A61K 39/001154* (2018.08); *A61P 35/00* (2018.01);
(Continued)

(58) Field of Classification Search
CPC . C07K 16/2818; C07K 2317/76; A61P 35/00; C12N 9/78; A61K 2039/505; A61K 39/001154; A61K 38/00; A61K 39/395; A61K 2300/00; A61K 2039/55594; C12Y 305/03001
See application file for complete search history.

(56) References Cited

U.S. PATENT DOCUMENTS 10,858,642 B2 * 12/2020 Andersen ....... A61K 39/001154
2002/0119554 A1 * 8/2002 Vockley .................... A61P 9/12
435/325

(Continued)

FOREIGN PATENT DOCUMENTS

EP       1033401 A2    9/2000
WO    WO-0230268 A2 *  4/2002 .............. A61P 13/08
(Continued)

OTHER PUBLICATIONS

NIH/National Library of Medicine/National Center for Biotechnology Information, arginase-2, mitochondrial precursor [*Homos sapiens*], NCBI Reference sequence: NP_001163.1, pp. 1-3, printed Mar. 27, 2024.*
(Continued)

*Primary Examiner* — Alana Harris Dent
(74) *Attorney, Agent, or Firm* — COOLEY LLP

(57) ABSTRACT

The present invention relates to novel polypeptides, which are derived from Arginase2. The invention also concerns uses of the polypeptides and compositions comprising the polypeptides.

7 Claims, 24 Drawing Sheets

Specification includes a Sequence Listing.

```
                ARG2-E18        ARG2-E20
ARG2-E17        ARG2-E19
GFSWIKPCIS  SASIVYIGLR  DVDPPEHFIL  KNYDIQYFSM  RDIDRLGIQK    Human ARG2 "hotspot region":180-229 aa
GFSWVTPCIS  AKDIVYIGLR  DVDPGEHYIL  KTLGIKYFSM  TEVDRLGIGK    Human ARG1 "hotspot region":161-210 aa
ARG-17                  ARG-19
        ARG-18                  ARG-20
```

(51) Int. Cl.
*A61P 35/00* (2006.01)
*C12N 9/78* (2006.01)

(52) U.S. Cl.
CPC .......... *C12N 9/78* (2013.01); *A61K 2039/505* (2013.01); *C12Y 305/03001* (2013.01)

(56) References Cited

U.S. PATENT DOCUMENTS

| | | | | |
|---|---|---|---|---|
| 2007/0014801 A1* | 1/2007 | Gish | ........................ | A61P 35/00 424/155.1 |
| 2014/0242060 A1* | 8/2014 | Georgiou | ............... | A61K 33/24 424/94.6 |
| 2017/0128553 A1 | 5/2017 | Georgiou et al. | | |

FOREIGN PATENT DOCUMENTS

| | | | |
|---|---|---|---|
| WO | 2016/172722 A1 | 10/2016 | |
| WO | 2018/065563 A1 | 4/2018 | |
| WO | 2020/064744 A1 | 4/2020 | |

OTHER PUBLICATIONS

Khong et al. Adjuvants for peptide-based cancer vaccines. Journal for Immuno Therapy of Cancer 4:56, pp. 1-11, published online Sep. 20, 2016.*
Castro et al., "Interferon-Gamma at the Crossroads of Tumor Immune Surveillance or Evasion," Front. Immunol. (2018) 9:847, 19 pages.
Mandai et al., "Dual Faces of IFNγ in Cancer Progression: A Role of PD-L1 Induction in the Determination of Pro-and Antitumor Immunity," Clin Cancer Res; May 2016, 22(10); 2329-2334.
Database Geneseq [Online] Aug. 10, 2017, "Mitochondrial targeting peptide, SEQ: 431.", XP002796410, retrieved from EBI accession No. GSP:BEA23126. Database accession No. BEA23126.
Database Geneseq [Online] Sep. 19, 2001, "Arginase peptide fragment.", retrieved from EBI accession No. GSP:AAG64222. Database accession No. AAG64222.
Singapore Search Report for Singapore Application No. 11202104881V, dated Dec. 13, 2022, 2 pages.
Singapore Written Opinion for Singapore Application No. 11202104881V, dated Dec. 14, 2022, 6 pages.

* cited by examiner

| ARG2-E17 | ARG2-E18 | ARG2-E19 | ARG2-E20 | |
|---|---|---|---|---|
| GFSWIKPCIS | SASIVYIGLR | DVDPPEHFIL | KNYDIQYFSM | RDIDRLGIQK | Human ARG2 "hotspot region":180-229 aa |
| GFSWVTPCIS | AKDIVYIGLR | DVDPGEHYIL | KTLGIKYFSM | TEVDRLGIGK | Human ARG1 "hotspot region":161-210 aa |
| ARG-17 | | ARG-19 | | | |
| | ARG-18 | | ARG-20 | | |

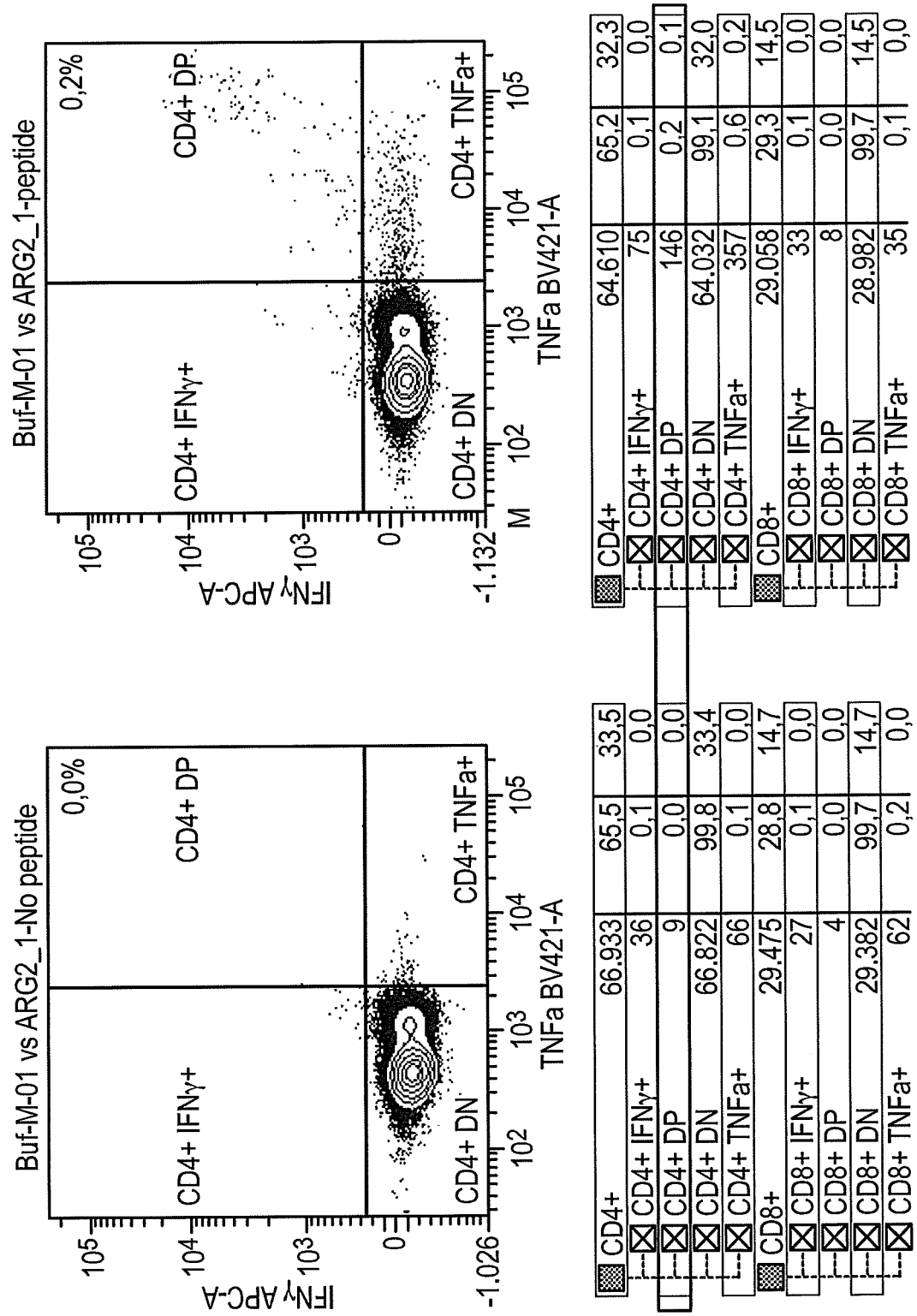

A

B

A

B

C

D

E

A

B

I

A

A

B

SEQUENCE LISTING

<160> NUMBER OF SEQ ID NOS: 64

<210> SEQ ID NO 1
<211> LENGTH: 20
<212> TYPE: PRT
<213> ORGANISM: Homo sapiens

<400> SEQUENCE: 1

Met Ser Leu Arg Gly Ser Leu Ser Arg Leu Leu Gln Thr Arg Val His
1               5                   10                  15

Ser Ile Leu Lys
            20

<210> SEQ ID NO 2
<211> LENGTH: 20
<212> TYPE: PRT
<213> ORGANISM: Homo sapiens

<400> SEQUENCE: 2

Leu Gln Thr Arg Val His Ser Ile Leu Lys Lys Ser Val His Ser Val
1               5                   10                  15

```
Ala Val Ile Gly
            20

<210> SEQ ID NO 3
<211> LENGTH: 20
<212> TYPE: PRT
<213> ORGANISM: Homo sapiens

<400> SEQUENCE: 3

Lys Ser Val His Ser Val Ala Val Ile Gly Ala Pro Phe Ser Gln Gly
1               5                   10                  15

Gln Lys Arg Lys
            20

<210> SEQ ID NO 4
<211> LENGTH: 20
<212> TYPE: PRT
<213> ORGANISM: Homo sapiens

<400> SEQUENCE: 4

Ala Pro Phe Ser Gln Gly Gln Lys Arg Lys Gly Val Glu His Gly Pro
1               5                   10                  15

Ala Ala Ile Arg
            20

<210> SEQ ID NO 5
<211> LENGTH: 20
<212> TYPE: PRT
<213> ORGANISM: Homo sapiens

<400> SEQUENCE: 5

Gly Val Glu His Gly Pro Ala Ala Ile Arg Glu Ala Gly Leu Met Lys
1               5                   10                  15

Arg Leu Ser Ser
            20

<210> SEQ ID NO 6
<211> LENGTH: 20
<212> TYPE: PRT
<213> ORGANISM: Homo sapiens

<400> SEQUENCE: 6

Glu Ala Gly Leu Met Lys Arg Leu Ser Ser Leu Gly Cys His Leu Lys
1               5                   10                  15

Asp Phe Gly Asp
            20

<210> SEQ ID NO 7
<211> LENGTH: 20
<212> TYPE: PRT
<213> ORGANISM: Homo sapiens

<400> SEQUENCE: 7

Leu Gly Cys His Leu Lys Asp Phe Gly Asp Leu Ser Phe Thr Pro Val
1               5                   10                  15

Pro Lys Asp Asp
            20

<210> SEQ ID NO 8
<211> LENGTH: 20
<212> TYPE: PRT
<213> ORGANISM: Homo sapiens
```

<400> SEQUENCE: 8

Leu Ser Phe Thr Pro Val Pro Lys Asp Asp Leu Tyr Asn Asn Leu Ile
1               5                   10                  15

Val Asn Pro Arg
            20

<210> SEQ ID NO 9
<211> LENGTH: 20
<212> TYPE: PRT
<213> ORGANISM: Homo sapiens

<400> SEQUENCE: 9

Leu Tyr Asn Asn Leu Ile Val Asn Pro Arg Ser Val Gly Leu Ala Asn
1               5                   10                  15

Gln Glu Leu Ala
            20

<210> SEQ ID NO 10
<211> LENGTH: 20
<212> TYPE: PRT
<213> ORGANISM: Homo sapiens

<400> SEQUENCE: 10

Ser Val Gly Leu Ala Asn Gln Glu Leu Ala Glu Val Val Ser Arg Ala
1               5                   10                  15

Val Ser Asp Gly
            20

<210> SEQ ID NO 11
<211> LENGTH: 20
<212> TYPE: PRT
<213> ORGANISM: Homo sapiens

<400> SEQUENCE: 11

Glu Val Val Ser Arg Ala Val Ser Asp Gly Tyr Ser Cys Val Thr Leu
1               5                   10                  15

Gly Gly Asp His
            20

<210> SEQ ID NO 12
<211> LENGTH: 20
<212> TYPE: PRT
<213> ORGANISM: Homo sapiens

<400> SEQUENCE: 12

Tyr Ser Cys Val Thr Leu Gly Gly Asp His Ser Leu Ala Ile Gly Thr
1               5                   10                  15

Ile Ser Gly His
            20

<210> SEQ ID NO 13
<211> LENGTH: 20
<212> TYPE: PRT
<213> ORGANISM: Homo sapiens

<400> SEQUENCE: 13

Ser Leu Ala Ile Gly Thr Ile Ser Gly His Ala Arg His Cys Pro Asp
1               5                   10                  15

Leu Cys Val Val
            20

```
<210> SEQ ID NO 14
<211> LENGTH: 20
<212> TYPE: PRT
<213> ORGANISM: Homo sapiens

<400> SEQUENCE: 14

Ala Arg His Cys Pro Asp Leu Cys Val Val Trp Val Asp Ala His Ala
1               5                   10                  15

Asp Ile Asn Thr
            20

<210> SEQ ID NO 15
<211> LENGTH: 20
<212> TYPE: PRT
<213> ORGANISM: Homo sapiens

<400> SEQUENCE: 15

Trp Val Asp Ala His Ala Asp Ile Asn Thr Pro Leu Thr Thr Ser Ser
1               5                   10                  15

Gly Asn Leu His
            20

<210> SEQ ID NO 16
<211> LENGTH: 20
<212> TYPE: PRT
<213> ORGANISM: Homo sapiens

<400> SEQUENCE: 16

Pro Leu Thr Thr Ser Ser Gly Asn Leu His Gly Gln Pro Val Ser Phe
1               5                   10                  15

Leu Leu Arg Glu
            20

<210> SEQ ID NO 17
<211> LENGTH: 20
<212> TYPE: PRT
<213> ORGANISM: Homo sapiens

<400> SEQUENCE: 17

Gly Gln Pro Val Ser Phe Leu Leu Arg Glu Leu Gln Asp Lys Val Pro
1               5                   10                  15

Gln Leu Pro Gly
            20

<210> SEQ ID NO 18
<211> LENGTH: 20
<212> TYPE: PRT
<213> ORGANISM: Homo sapiens

<400> SEQUENCE: 18

Leu Gln Asp Lys Val Pro Gln Leu Pro Gly Phe Ser Trp Ile Lys Pro
1               5                   10                  15

Cys Ile Ser Ser
            20

<210> SEQ ID NO 19
<211> LENGTH: 20
<212> TYPE: PRT
<213> ORGANISM: Homo sapiens

<400> SEQUENCE: 19

Phe Ser Trp Ile Lys Pro Cys Ile Ser Ser Ala Ser Ile Val Tyr Ile
1               5                   10                  15
```

Gly Leu Arg Asp
        20

<210> SEQ ID NO 20
<211> LENGTH: 20
<212> TYPE: PRT
<213> ORGANISM: Homo sapiens

<400> SEQUENCE: 20

Ala Ser Ile Val Tyr Ile Gly Leu Arg Asp Val Asp Pro Glu His
1               5                   10                  15

Phe Ile Leu Lys
        20

<210> SEQ ID NO 21
<211> LENGTH: 20
<212> TYPE: PRT
<213> ORGANISM: Homo sapiens

<400> SEQUENCE: 21

Val Asp Pro Pro Glu His Phe Ile Leu Lys Asn Tyr Asp Ile Gln Tyr
1               5                   10                  15

Phe Ser Met Arg
        20

<210> SEQ ID NO 22
<211> LENGTH: 20
<212> TYPE: PRT
<213> ORGANISM: Homo sapiens

<400> SEQUENCE: 22

Asn Tyr Asp Ile Gln Tyr Phe Ser Met Arg Asp Ile Asp Arg Leu Gly
1               5                   10                  15

Ile Gln Lys Val
        20

<210> SEQ ID NO 23
<211> LENGTH: 20
<212> TYPE: PRT
<213> ORGANISM: Homo sapiens

<400> SEQUENCE: 23

Asp Ile Asp Arg Leu Gly Ile Gln Lys Val Met Glu Arg Thr Phe Asp
1               5                   10                  15

Leu Leu Ile Gly
        20

<210> SEQ ID NO 24
<211> LENGTH: 20
<212> TYPE: PRT
<213> ORGANISM: Homo sapiens

<400> SEQUENCE: 24

Met Glu Arg Thr Phe Asp Leu Leu Ile Gly Lys Arg Gln Arg Pro Ile
1               5                   10                  15

His Leu Ser Phe
        20

<210> SEQ ID NO 25
<211> LENGTH: 20
<212> TYPE: PRT
<213> ORGANISM: Homo sapiens

```
<400> SEQUENCE: 25

Lys Arg Gln Arg Pro Ile His Leu Ser Phe Asp Ile Asp Ala Phe Asp
1               5                   10                  15

Pro Thr Leu Ala
            20

<210> SEQ ID NO 26
<211> LENGTH: 20
<212> TYPE: PRT
<213> ORGANISM: Homo sapiens

<400> SEQUENCE: 26

Asp Ile Asp Ala Phe Asp Pro Thr Leu Ala Pro Ala Thr Gly Thr Pro
1               5                   10                  15

Val Val Gly Gly
            20

<210> SEQ ID NO 27
<211> LENGTH: 20
<212> TYPE: PRT
<213> ORGANISM: Homo sapiens

<400> SEQUENCE: 27

Pro Ala Thr Gly Thr Pro Val Val Gly Gly Leu Thr Tyr Arg Glu Gly
1               5                   10                  15

Met Tyr Ile Ala
            20

<210> SEQ ID NO 28
<211> LENGTH: 20
<212> TYPE: PRT
<213> ORGANISM: Homo sapiens

<400> SEQUENCE: 28

Leu Thr Tyr Arg Glu Gly Met Tyr Ile Ala Glu Glu Ile His Asn Thr
1               5                   10                  15

Gly Leu Leu Ser
            20

<210> SEQ ID NO 29
<211> LENGTH: 20
<212> TYPE: PRT
<213> ORGANISM: Homo sapiens

<400> SEQUENCE: 29

Glu Glu Ile His Asn Thr Gly Leu Leu Ser Ala Leu Asp Leu Val Glu
1               5                   10                  15

Val Asn Pro Gln
            20

<210> SEQ ID NO 30
<211> LENGTH: 20
<212> TYPE: PRT
<213> ORGANISM: Homo sapiens

<400> SEQUENCE: 30

Ala Leu Asp Leu Val Glu Val Asn Pro Gln Leu Ala Thr Ser Glu Glu
1               5                   10                  15

Glu Ala Lys Thr
            20
```

```
<210> SEQ ID NO 31
<211> LENGTH: 20
<212> TYPE: PRT
<213> ORGANISM: Homo sapiens

<400> SEQUENCE: 31

Leu Ala Thr Ser Glu Glu Ala Lys Thr Thr Ala Asn Leu Ala Val
1               5                   10                  15

Asp Val Ile Ala
            20

<210> SEQ ID NO 32
<211> LENGTH: 20
<212> TYPE: PRT
<213> ORGANISM: Homo sapiens

<400> SEQUENCE: 32

Thr Ala Asn Leu Ala Val Asp Val Ile Ala Ser Ser Phe Gly Gln Thr
1               5                   10                  15

Arg Glu Gly Gly
            20

<210> SEQ ID NO 33
<211> LENGTH: 20
<212> TYPE: PRT
<213> ORGANISM: Homo sapiens

<400> SEQUENCE: 33

Ser Ser Phe Gly Gln Thr Arg Glu Gly Gly His Ile Val Tyr Asp Gln
1               5                   10                  15

Leu Pro Thr Pro
            20

<210> SEQ ID NO 34
<211> LENGTH: 24
<212> TYPE: PRT
<213> ORGANISM: Homo sapiens

<400> SEQUENCE: 34

His Ile Val Tyr Asp Gln Leu Pro Thr Pro Ser Ser Pro Asp Glu Ser
1               5                   10                  15

Glu Asn Gln Ala Arg Val Arg Ile
            20

<210> SEQ ID NO 35
<211> LENGTH: 20
<212> TYPE: PRT
<213> ORGANISM: Homo sapiens

<400> SEQUENCE: 35

Gly Phe Ser Trp Ile Lys Pro Cys Ile Ser Ser Ala Ser Ile Val Tyr
1               5                   10                  15

Ile Gly Leu Arg
            20

<210> SEQ ID NO 36
<211> LENGTH: 20
<212> TYPE: PRT
<213> ORGANISM: Homo sapiens

<400> SEQUENCE: 36

Ser Ala Ser Ile Val Tyr Ile Gly Leu Arg Asp Val Asp Pro Pro Glu
```

```
1               5                  10                 15
His Phe Ile Leu
            20

<210> SEQ ID NO 37
<211> LENGTH: 20
<212> TYPE: PRT
<213> ORGANISM: Homo sapiens

<400> SEQUENCE: 37

Asp Val Asp Pro Pro Glu His Phe Ile Leu Lys Asn Tyr Asp Ile Gln
1               5                  10                 15

Tyr Phe Ser Met
            20

<210> SEQ ID NO 38
<211> LENGTH: 20
<212> TYPE: PRT
<213> ORGANISM: Homo sapiens

<400> SEQUENCE: 38

Lys Asn Tyr Asp Ile Gln Tyr Phe Ser Met Arg Asp Ile Asp Arg Leu
1               5                  10                 15

Gly Ile Gln Lys
            20

<210> SEQ ID NO 39
<211> LENGTH: 50
<212> TYPE: PRT
<213> ORGANISM: Homo sapiens

<400> SEQUENCE: 39

Gly Phe Ser Trp Ile Lys Pro Cys Ile Ser Ser Ala Ser Ile Val Tyr
1               5                  10                 15

Ile Gly Leu Arg Asp Val Asp Pro Pro Glu His Phe Ile Leu Lys Asn
            20                 25                 30

Tyr Asp Ile Gln Tyr Phe Ser Met Arg Asp Ile Asp Arg Leu Gly Ile
                35                 40                 45

Gln Lys
    50

<210> SEQ ID NO 40
<211> LENGTH: 50
<212> TYPE: PRT
<213> ORGANISM: Homo sapiens

<400> SEQUENCE: 40

Gly Phe Ser Trp Val Thr Pro Cys Ile Ser Ala Lys Asp Ile Val Tyr
1               5                  10                 15

Ile Gly Leu Arg Asp Val Asp Pro Gly Glu His Tyr Ile Leu Lys Thr
            20                 25                 30

Leu Gly Ile Lys Tyr Phe Ser Met Thr Glu Val Asp Arg Leu Gly Ile
            35                 40                 45

Gly Lys
    50

<210> SEQ ID NO 41
<211> LENGTH: 20
<212> TYPE: PRT
<213> ORGANISM: Homo sapiens
```

<400> SEQUENCE: 41

Gly Phe Ser Trp Val Thr Pro Cys Ile Ser Ala Lys Asp Ile Val Tyr
1               5                   10                  15

Ile Gly Leu Arg
            20

<210> SEQ ID NO 42
<211> LENGTH: 20
<212> TYPE: PRT
<213> ORGANISM: Homo sapiens

<400> SEQUENCE: 42

Ala Lys Asp Ile Val Tyr Ile Gly Leu Arg Asp Val Asp Pro Gly Glu
1               5                   10                  15

His Tyr Ile Leu
            20

<210> SEQ ID NO 43
<211> LENGTH: 20
<212> TYPE: PRT
<213> ORGANISM: Homo sapiens

<400> SEQUENCE: 43

Asp Val Asp Pro Gly Glu His Tyr Ile Leu Lys Thr Leu Gly Ile Lys
1               5                   10                  15

Tyr Phe Ser Met
            20

<210> SEQ ID NO 44
<211> LENGTH: 20
<212> TYPE: PRT
<213> ORGANISM: Homo sapiens

<400> SEQUENCE: 44

Lys Thr Leu Gly Ile Lys Tyr Phe Ser Met Thr Glu Val Asp Arg Leu
1               5                   10                  15

Gly Ile Gly Lys
            20

<210> SEQ ID NO 45
<211> LENGTH: 9
<212> TYPE: PRT
<213> ORGANISM: Mus musculus

<400> SEQUENCE: 45

Val Val Tyr Pro Arg Ser Val Gly Leu
1               5

<210> SEQ ID NO 46
<211> LENGTH: 18
<212> TYPE: PRT
<213> ORGANISM: Mus musculus

<400> SEQUENCE: 46

Val Val Tyr Pro Arg Ser Val Gly Leu Ala Asn Gln Glu Leu Ala Glu
1               5                   10                  15

Val Val

<210> SEQ ID NO 47
<211> LENGTH: 8
<212> TYPE: PRT
<213> ORGANISM: Mus musculus

```
<400> SEQUENCE: 47

Pro Asn Ile Val Tyr Ile Gly Leu
1               5

<210> SEQ ID NO 48
<211> LENGTH: 16
<212> TYPE: PRT
<213> ORGANISM: Mus musculus

<400> SEQUENCE: 48

Trp Ile Lys Pro Cys Leu Ser Pro Pro Asn Ile Val Tyr Ile Gly Leu
1               5                   10                  15

<210> SEQ ID NO 49
<211> LENGTH: 9
<212> TYPE: PRT
<213> ORGANISM: Mus musculus

<400> SEQUENCE: 49

Leu Ser Pro Pro Asn Ile Val Tyr Ile
1               5

<210> SEQ ID NO 50
<211> LENGTH: 9
<212> TYPE: PRT
<213> ORGANISM: Mus musculus

<400> SEQUENCE: 50

Ile Gln Tyr Phe Ser Met Arg Glu Ile
1               5

<210> SEQ ID NO 51
<211> LENGTH: 354
<212> TYPE: PRT
<213> ORGANISM: Homo sapiens

<400> SEQUENCE: 51

Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
                20                  25                  30

Phe Ser Gln Gly Gln Lys Arg Lys Gly Val Glu His Gly Pro Ala Ala
            35                  40                  45

Ile Arg Glu Ala Gly Leu Met Lys Arg Leu Ser Ser Leu Gly Cys His
        50                  55                  60

Leu Lys Asp Phe Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
        115                 120                 125

Gly His Ala Arg His Cys Pro Asp Leu Cys Val Val Trp Val Asp Ala
    130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175
```

Gln Leu Pro Gly Phe Ser Trp Ile Lys Pro Cys Ile Ser Ala Ser
            180                 185                 190

Ile Val Tyr Ile Gly Leu Arg Asp Val Asp Pro Pro Glu His Phe Ile
        195                 200                 205

Leu Lys Asn Tyr Asp Ile Gln Tyr Phe Ser Met Arg Asp Ile Asp Arg
    210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
        275                 280                 285

Leu Ser Ala Leu Asp Leu Val Glu Val Asn Pro Gln Leu Ala Thr Ser
    290                 295                 300

Glu Glu Glu Ala Lys Thr Thr Ala Asn Leu Ala Val Asp Val Ile Ala
305                 310                 315                 320

Ser Ser Phe Gly Gln Thr Arg Glu Gly Gly His Ile Val Tyr Asp Gln
                325                 330                 335

Leu Pro Thr Pro Ser Ser Pro Asp Glu Ser Glu Asn Gln Ala Arg Val
            340                 345                 350

Arg Ile

<210> SEQ ID NO 52
<211> LENGTH: 354
<212> TYPE: PRT
<213> ORGANISM: Mus musculus

<400> SEQUENCE: 52

Met Phe Leu Arg Ser Ser Ala Ser Arg Leu Leu His Gly Gln Ile Pro
1               5                   10                  15

Cys Val Leu Thr Arg Ser Val His Ser Val Ala Ile Val Gly Ala Pro
            20                  25                  30

Phe Ser Arg Gly Gln Lys Lys Leu Gly Val Glu Tyr Gly Pro Ala Ala
        35                  40                  45

Ile Arg Glu Ala Gly Leu Leu Lys Arg Leu Ser Arg Leu Gly Cys His
    50                  55                  60

Leu Lys Asp Phe Gly Asp Leu Ser Phe Thr Asn Val Pro Gln Asp Asp
65                  70                  75                  80

Pro Tyr Asn Asn Leu Val Val Tyr Pro Arg Ser Val Gly Leu Ala Asn
                85                  90                  95

Gln Glu Leu Ala Glu Val Val Ser Arg Ala Val Ser Gly Gly Tyr Ser
            100                 105                 110

Cys Val Thr Met Gly Gly Asp His Ser Leu Ala Ile Gly Thr Ile Ile
        115                 120                 125

Gly His Ala Arg His Arg Pro Asp Leu Cys Val Ile Trp Val Asp Ala
    130                 135                 140

His Ala Asp Ile Asn Thr Pro Leu Thr Thr Val Ser Gly Asn Ile His
145                 150                 155                 160

Gly Gln Pro Leu Ser Phe Leu Ile Lys Glu Leu Gln Asp Lys Val Pro
                165                 170                 175

Gln Leu Pro Gly Phe Ser Trp Ile Lys Pro Cys Leu Ser Pro Pro Asn
            180                 185                 190

-continued

Ile Val Tyr Ile Gly Leu Arg Asp Val Glu Pro Glu His Phe Ile
                195                 200                 205

Leu Lys Asn Tyr Asp Ile Gln Tyr Phe Ser Met Arg Glu Ile Asp Arg
210                 215                 220

Leu Gly Ile Gln Lys Val Met Glu Gln Thr Phe Asp Arg Leu Ile Gly
225                 230                 235                 240

Lys Arg Gln Arg Pro Ile His Leu Ser Phe Asp Ile Asp Ala Phe Asp
                245                 250                 255

Pro Lys Leu Ala Pro Ala Thr Gly Thr Pro Val Val Gly Gly Leu Thr
                260                 265                 270

Tyr Arg Glu Gly Val Tyr Ile Thr Glu Glu Ile His Asn Thr Gly Leu
                275                 280                 285

Leu Ser Ala Leu Asp Leu Val Glu Val Asn Pro His Leu Ala Thr Ser
                290                 295                 300

Glu Glu Glu Ala Lys Ala Thr Ala Arg Leu Ala Val Asp Val Ile Ala
305                 310                 315                 320

Ser Ser Phe Gly Gln Thr Arg Glu Gly Gly His Ile Val Tyr Asp His
                325                 330                 335

Leu Pro Thr Pro Ser Ser Pro His Glu Ser Glu Asn Glu Glu Cys Val
                340                 345                 350

Arg Ile

<210> SEQ ID NO 53
<211> LENGTH: 322
<212> TYPE: PRT
<213> ORGANISM: Homo sapiens

<400> SEQUENCE: 53

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
                20                  25                  30

Lys Ala Gly Leu Leu Glu Lys Leu Lys Glu Gln Glu Cys Asp Val Lys
            35                  40                  45

Asp Tyr Gly Asp Leu Pro Phe Ala Asp Ile Pro Asn Asp Ser Pro Phe
50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
                100                 105                 110

Arg Val His Pro Asp Leu Gly Val Ile Trp Val Asp Ala His Thr Asp
            115                 120                 125

Ile Asn Thr Pro Leu Thr Thr Thr Ser Gly Asn Leu His Gly Gln Pro
130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
                180                 185                 190

Leu Gly Ile Lys Tyr Phe Ser Met Thr Glu Val Asp Arg Leu Gly Ile
                195                 200                 205

```
Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Leu Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
            275                 280                 285

Val Thr Arg Thr Val Asn Thr Ala Val Ala Ile Thr Leu Ala Cys Phe
            290                 295                 300

Gly Leu Ala Arg Glu Gly Asn His Lys Pro Ile Asp Tyr Leu Asn Pro
305                 310                 315                 320

Pro Lys

<210> SEQ ID NO 54
<211> LENGTH: 10
<212> TYPE: PRT
<213> ORGANISM: Homo sapiens

<400> SEQUENCE: 54

Ile Leu Lys Lys Ser Val His Ser Val Ala
1               5                   10

<210> SEQ ID NO 55
<211> LENGTH: 9
<212> TYPE: PRT
<213> ORGANISM: Homo sapiens

<400> SEQUENCE: 55

Ile Leu Lys Lys Ser Val His Ser Val
1               5

<210> SEQ ID NO 56
<211> LENGTH: 10
<212> TYPE: PRT
<213> ORGANISM: Homo sapiens

<400> SEQUENCE: 56

Ser Ile Leu Lys Lys Ser Val His Ser Val
1               5                   10

<210> SEQ ID NO 57
<211> LENGTH: 29
<212> TYPE: PRT
<213> ORGANISM: Homo sapiens

<400> SEQUENCE: 57

Ser Leu Ser Arg Leu Leu Gln Thr Arg Val His Ser Ile Leu Lys Lys
1               5                   10                  15

Ser Val His Ser Val Ala Val Ile Gly Ala Pro Phe Ser
            20                  25

<210> SEQ ID NO 58
<211> LENGTH: 30
<212> TYPE: PRT
<213> ORGANISM: Homo sapiens

<400> SEQUENCE: 58
```

```
Ser Leu Arg Gly Ser Leu Ser Arg Leu Leu Gln Thr Arg Val His Ser
1               5                   10                  15

Ile Leu Lys Lys Ser Val His Ser Val Ala Val Ile Gly Ala
            20                  25                  30
```

<210> SEQ ID NO 59
<211> LENGTH: 33
<212> TYPE: PRT
<213> ORGANISM: Homo sapiens

<400> SEQUENCE: 59

```
Ser Leu Arg Gly Ser Leu Ser Arg Leu Leu Gln Thr Arg Val His Ser
1               5                   10                  15

Ile Leu Lys Lys Ser Val His Ser Val Ala Val Ile Gly Ala Pro Phe
            20                  25                  30

Ser
```

<210> SEQ ID NO 60
<211> LENGTH: 29
<212> TYPE: PRT
<213> ORGANISM: Homo sapiens

<400> SEQUENCE: 60

```
Phe Ser Trp Ile Lys Pro Cys Ile Ser Ser Ala Ser Ile Val Tyr Ile
1               5                   10                  15

Gly Leu Arg Asp Val Asp Pro Pro Glu His Phe Ile Leu
            20                  25
```

<210> SEQ ID NO 61
<211> LENGTH: 32
<212> TYPE: PRT
<213> ORGANISM: Homo sapiens

<400> SEQUENCE: 61

```
Leu Pro Gly Phe Ser Trp Ile Lys Pro Cys Ile Ser Ser Ala Ser Ile
1               5                   10                  15

Val Tyr Ile Gly Leu Arg Asp Val Asp Pro Pro Glu His Phe Ile Leu
            20                  25                  30
```

<210> SEQ ID NO 62
<211> LENGTH: 22
<212> TYPE: PRT
<213> ORGANISM: Homo sapiens

<400> SEQUENCE: 62

```
Met Ser Leu Arg Gly Ser Leu Ser Arg Leu Leu Gln Thr Arg Val His
1               5                   10                  15

Ser Ile Leu Lys Lys Ser
            20
```

<210> SEQ ID NO 63
<211> LENGTH: 56
<212> TYPE: PRT
<213> ORGANISM: Homo sapiens

<400> SEQUENCE: 63

```
Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
```

```
                35                  40                  45

Ile Arg Glu Ala Gly Leu Met Lys
        50                  55

<210> SEQ ID NO 64
<211> LENGTH: 38
<212> TYPE: PRT
<213> ORGANISM: Homo sapiens

<400> SEQUENCE: 64

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu
            35
```

IMMUNOGENIC ARGINASE 2 POLYPEPTIDES

RELATED INFORMATION PARAGRAPH

This application is a 35 U.S.C. 371 national stage filing of International Application No. PCT/EP2019/081369, filed on Nov. 14, 2019, which claims the benefit of the priority date of United Kingdom Application No. GB1818576.9, filed on Nov. 14, 2018, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 12, 2021, is named JKJ-072US_Sequence_Listing.txt and is 25,030 bytes in size.

FIELD OF THE INVENTION

The present invention relates to novel polypeptides, which are derived from Arginase2. The invention also concerns uses of the polypeptides and compositions comprising the polypeptides.

BACKGROUND OF THE INVENTION

Arginases are enzymes that catalyse a reaction which converts the amino acid L-arginine into L-ornithine and urea. This depletes the microenvironment of arginine and leads to a suppression of tumor-specific cytotoxic T-cell responses. Increased Arginase activity has been detected in the cancer cells of patients with, for example, breast, lung, colon or prostate cancer. It has been shown both in vitro and in vivo that mouse macrophages transfected with a rat Arginase gene promote the proliferation of co-cultured tumour cells. Furthermore induction of Arginase expression by macrophages has been shown to increase tumour vascularization through polyamine synthesis. The results of a murine lung carcinoma model showed that there existed a subpopulation of mature tumor-associated myeloid cells that expressed high levels of Arginase. These tumor-associated myeloid cells depleted the extracellular L-Arginine which inhibited antigen-specific proliferation of the tumor infiltrating lymphocytes (TILs). Injection of an Arginase inhibitor blocked the growth of the lung carcinoma in the mice. This shows how induction of Arginase expression in tumor cells and tumor associated myeoloid cells might promote tumor growth by suppression of the anti-tumor immune responses through negative effects on TILs.

MDSCs (myeloid-derived suppressor cells) inhibit the activation, proliferation, and cytotoxicity of effector T cells and natural killer cells, as well as induce Treg differentiation and expansion. Both cancer cells and MDSCs can suppress T cells by manipulating L-arginine metabolism via the enzymes nitric-oxide synthase (NOS) and arginase. Many tumours exhibit increased expressions of arginase and inducible NOS (iNOS), leading to arginine depletion from the tumour microenvironment. Several studies emphasize the importance of this altered tumour arginine metabolism in the suppression of tumour-specific T-cell responses, and it was recently demonstrated that Acute Myeloid Leukemia (AML) blasts show an arginase-dependent ability to inhibit T-cell proliferation and hematopoietic stem cells. Furthermore, arginase and iNOS inhibitors reduce the suppressive activity of AML.

In mammals, two arginase isoenzymes exist: Arginase1 and Arginase2. The two isoenzymes catalyse the same biochemical reaction (and thus cannot be disntinguished by enzymatic assays) but differ in cellular expression, regulation and subcellular localisation.

SUMMARY OF THE INVENTION

The present inventors have previously identified a 50 amino acid region of Arginase1 and Arginase2 which is a "hot spot" for immunogenicity. This region corresponds to positions 161-210 of full length human Arginase1 (SEQ ID NO: 53) or positions 180-229 of full length human Arginase2 (SEQ ID NO: 51), or corresponding positions in murine Arginases. The region and peptides derived from it are described in WO2018065563. The present inventors have also identified that a specific sub-set of polypeptides derived from the "hot spot" region of Arginase1 are particularly effective at stimulating immune responses. These peptides correspond to positions 169-206 of full length human Arginase1, positions 169-200 of full length human Arginase1 or positions 169-210 of full length human Arginase1 (or corresponding positions in human Arginase2 or murine Arginase1). This sub-set of polypeptides is described in PCT/EP2019/075731 and its priority application GB1815549.9.

The present inventors have now identified that polypeptides derived from an entirely different region of human Arginase2 are particularly effective at stimulating immune responses. Surprisingly, the region spans the C-terminus of the transit peptide of human Arginase2 (position 22 of SEQ ID NO: 51-see schematic diagram in FIG. 7). Sequence identity to human Arginase1 is relatively low in this region.

The polypeptides of the present invention are expected to be particularly effective at stimulating a beneficial immune response against Arginase2 and Arginase2-expressing cells. The development of novel immune therapies for cancer requires a thorough understanding of the molecules that are involved in the pathogenesis as well as the specific proteins recognized by the immune system. In the clinical setting the induction of Arginase specific immune responses could in addition to the killing of cancer cells support anti-cancer immune responses in general by suppressing the immune suppressive function of Arginase expressing cells especially MDSC and tumor-associated macrophages (TAMs). Hence, since Arginase-expressing cells antagonize the desired effects of other immunotherapeutic approaches targeting myeloid dendritic cells e.g. by vaccination with the polypeptides of the present invention, would consequently be highly synergistic with additional anti-cancer immunotherapy.

The present invention provides a polypeptide which is an immunogenic fragment of human Arginase2 (SEQ ID NO: 51) that comprises or consists of a sequence of at least 9 consecutive amino acids of SEQ ID NO: 51 which (i) include at least the amino acids at positions 21, 22 and 23 of SEQ ID NO: 51, or (ii) are selected from positions 180-229 of SEQ ID NO: 51. The polypeptide may comprise or consist of up to 15, 20, 25, 30, 35, 40, 45 or 50 consecutive amino acids of SEQ ID NO: 51 as defined in (i) or (ii). The polypeptide may comprise or consist of the amino acid sequence of any one of SEQ ID NOs: 59, 58, 57, 54, 55, 56, 2, 3, 19, 20, 21, 60 or 61. The polypeptide may have a maximum length of 9, 10, 15, 20, 25, 30, 35, 40, 45 or 50 amino acids and/or in which the C terminal amino acid is replaced with the corresponding amide. The polypeptide may be isolated.

The present invention also provides a polypeptide which is an immunogenic fragment of murine Arginase2 (SEQ ID NO: 52) that comprises or consists of a sequence of at least 9 consecutive amino acids of SEQ ID NO: 52 which (i) include at least the amino acids at positions 21, 22 and 23 of SEQ ID NO: 52, or (ii) are selected from positions 180-229 of SEQ ID NO: 52. The polypeptide may comprise or consist of up to 15, 20, 25, 30, 35, 40, 45 or 50 consecutive amino acids of SEQ ID NO: 52 as defined in (i) or (ii). The polypeptide may have a maximum length of 9, 10, 15, 20, 25, 30, 35, 40, 45 or 50 amino acids and/or in which the C terminal amino acid is replaced with the corresponding amide. The polypeptide may be isolated.

The present invention also provides a composition comprising a polypeptide of the invention, at least one pharmaceutically acceptable diluent, carrier or preservative, and optionally an adjuvant.

The present invention also provides a method of treating or preventing a disease or condition in a subject, the method comprising administering to the subject a polypeptide or a composition of the invention.

BRIEF DESCRIPTION OF THE FIGURES

FIGS. 6A and 6B show CD4+ T cell responses of two healthy donors to ARG2_1 or with no peptide. PBMC cells were stained with CD4 antibody and analyzed in an intracellular cytokine release assay by flow cytometry with or without ARG2_1 stimulation. It can be seen from the figure that the CD4 cells release both IFN-gamma (y-axis) or TNF-alfa (x-axis) when stimulated with the ARG2-derived peptide.

BRIEF DESCRIPTION OF THE SEQUENCS

Figures 1, 2:
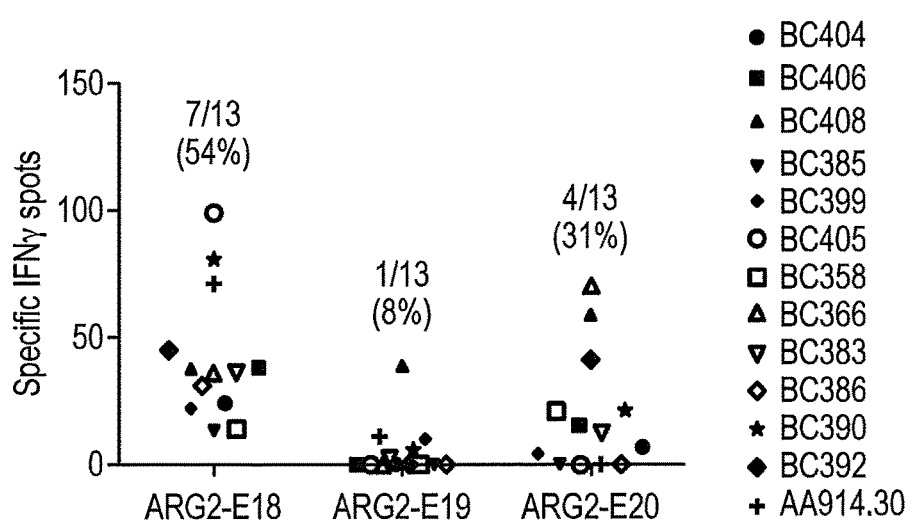
FIG. 1 shows the design of certain polypeptides spanning the "hotspot" region of both human Arginase1 and human Arginase2. Sequence identifier numbers are provided in Table X of the specification.
FIG. 2 shows that ARG2 peptides that correspond to the hotspot region are recognized by PBMCs from healthy donors and a melanoma patient (AA914.30). Spot counts are given as a difference between averages of the wells stimulated with peptide and control wells without peptide. $5*10^5$ cells were plated pr. well and peptide and control stimulations were performed in triplicates. Responses were analyzed using distribution free resampling (DFR) rule.

SEQ ID NOs: 1-38 are each an amino acid sequence of a polypeptide derived from human Arginase2.

SEQ ID NOs: 39 and 40 are corresponding "hot spot" regions of human Arginase2 and Arginase1 respectively.

SEQ ID Nos: 41-44 are each an amino acid sequence of a polypeptide derived from human Arginase1.

SEQ ID NOs: 45-50 are each an amino acid sequence of a polypeptide derived from murine Arginase2.

SEQ ID NO: 51 is the amino acid sequence of the full length human Arginase2.

SEQ ID NO: 52 is the amino acid sequence of the full length murine Arginase2.

SEQ ID NO: 53 is the amino acids sequence of full length human Arginase 1.

SEQ ID NOs: 54-56 are each an amino acid sequence of a polypeptide derived from human Arginase2, which correspond to the sequences of predicted HLA-A2 or A3 epitopes within the polypeptide of SEQ ID NO: 2 (Arg2_1).

SEQ ID NOs: 57-59 are each an amino acid sequence of a further polypeptide derived from human Arginase2 comprising at least one of the epitopes of SEQ ID NOs: 54-56.

SEQ ID NOs: 60-61 are each an amino acid sequence of a further polypeptide derived from human Arginase 2 including sequences from the "hotspot" region of SEQ ID NO: 39.

SEQ ID NO: 62 is the predicted signal sequence of human Arginase 2.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polypeptide" includes "polypeptides", and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

The terms "patient" and "subject" are used interchangeably and typically refer to a human.

All publications, patents and patent applications cited herein, whether supra or infra, are hereby incorporated by reference in their entirety.

The present inventors have identified that the region of human Arginase2 spanning the C-terminus of the transit peptide is particularly immunogenic. The C-terminal residue of the transit peptide corresponds to position 22 of SEQ ID NO: 51. Thus, the region spanning the C-terminus of the transit peptide encompasses at least the amino acids of positions 21, 22 and 23 of SEQ ID NO: 51.

By "immunogenic" herein it is meant that a polypeptide is capable of eliciting an immune response to the Arginase2 protein, preferably when said protein is present in or on cells expressing the Arginase2 protein. In other words, the polypeptide may be described as immunogenic to Arginase2. The polypeptide may alternatively be described as an immunogenic fragment of Arginase2. The immune response is preferably a T cell response, and so the polypeptide may be described as an immunogenic fragment of Arginase2 comprising a T cell epitope. The immune response may be detected in at least one individual (or in sample taken from the individual) after administration of the polypeptide to said individual (or said sample).

A polypeptide may be identified as immunogenic using any suitable method, including in vitro methods. For example, a peptide may be identified as immunogenic if it has at least one of the following characteristics:
 (i) It is capable of eliciting IFN-γ-producing cells in a PBL population of a healthy subject and/or a cancer patient as determined by an ELISPOT assay, and/or
 (ii) It is capable of in situ detection in a sample of tumor tissue of CTLs that are reactive with Arginase2; and/or (iii) It is capable of inducing the in vitro growth of specific T-cells.

Methods suitable for determining whether a polypeptide is immunogenic are also described in the Examples section below.

The polypeptide of the invention is an immunogenic fragment of human Arginase2 (SEQ ID NO: 51) that comprises or consists of a sequence of at least 9 consecutive amino acids of SEQ ID NO: 51 which (i) include at least the amino acids at positions 21, 22 and 23 of SEQ ID NO: 51, or (ii) are selected from positions 180-229 of SEQ ID NO: 51. The polypeptide may comprise or consist of up to 15, 20, 25, 30, 35, 40, 45 or 50 consecutive amino acids of SEQ ID NO: 51 as defined in (i) or (ii). The polypeptide may comprise or consist of the amino acid sequence of any one of SEQ ID NOs: 59, 58, 57, 54, 55, 56, 2, 3, 19, 20, 21, 60 or 61. The polypeptide may have a maximum length of 9, 10, 15, 20, 25, 30, 35, 40, 45 or 50 amino acids and/or in which the C terminal amino acid is replaced with the corresponding amide. The polypeptide may be isolated.

The polypeptide preferably comprises or consists of a sequence of at least 9 consecutive amino acids of SEQ ID NO: 51 which include at least the amino acids at positions 21, 22 and 23 of SEQ ID NO: 51, that is the sequence KSV. Said at least 9 consecutive amino acids of SEQ ID NO: 51 preferably include the amino acid sequence of SEQ ID NO: 54 (ILKKSVHSVA), SEQ ID NO: 55 (ILKKSVHSV) or SEQ ID NO: 56 (SILKKSVHSV). Preferred polypeptides of the invention may comprises or consist of the amino acid sequence of SEQ ID NO: 54, 55 or 56. Longer polypeptide fragments of SEQ ID NO: 51 which incorporate these sequences are particularly preferred. For example, the present invention provides a polypeptide of up to 50 consecutive amino acids of SEQ ID NO: 51, which consecutive amino acids include the amino sequence of any one of SEQ ID NOs: 54, 55 or 56. An exemplary polypeptide of this type is the polypeptide which comprises or consists of the sequence any one of SEQ ID NOs: 2, 3, 57, 58, or 59. A polypeptide which comprises or consists of the sequence of any one of SEQ ID NOs: 59, 58 and 57 is preferred. A polypeptide which comprises or consists of the sequence of SEQ ID NO: 59 is particularly preferred.

In any polypeptide described herein, the amino acid sequence may be modified by one, two, three, four, or five (that is upto five) additions, deletions or substitutions, provided that a polypeptide having the modified sequence exhibits the same or increased immunogenicity to Arginase2, as compared to a polypeptide having the unmodified sequence. By "the same" it is to be understood that the polypeptide of the modified sequence does not exhibit significantly reduced immunogenicity to Arginase2 as compared to polypeptide of the unmodified sequence. Any comparison of immunogenicity between sequences is to be conducted using the same assay. Unless otherwise specified, modifications to a polypeptide sequence are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2.

TABLE A1

Chemical properties of amino acids

| | |
|---|---|
| Ala (A) | aliphatic, hydrophobic, neutral |
| Cys (C) | polar, hydrophobic, neutral |
| Asp (D) | polar, hydrophilic, charged (−) |
| Glu (E) | polar, hydrophilic, charged (−) |
| Phe (F) | aromatic, hydrophobic, neutral |
| Gly (G) | aliphatic, neutral |
| His (H) | aromatic, polar, hydrophilic, charged (+) |
| Ile (I) | aliphatic, hydrophobic, neutral |
| Lys (K) | polar, hydrophilic, charged(+) |
| Leu (L) | aliphatic, hydrophobic, neutral |
| Met (M) | hydrophobic, neutral |
| Asn (N) | polar, hydrophilic, neutral |
| Pro (P) | hydrophobic, neutral |
| Gln (Q) | polar, hydrophilic, neutral |
| Arg (R) | polar, hydrophilic, charged (+) |
| Ser (S) | polar, hydrophilic, neutral |
| Thr (T) | polar, hydrophilic, neutral |
| Val (V) | aliphatic, hydrophobic, neutral |
| Trp (W) | aromatic, hydrophobic, neutral |
| Tyr (Y) | aromatic, polar, hydrophobic |

TABLE A2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

In any polypeptide disclosed herein, any one or more of the following modifications may be made to improve physiochemical properties (e.g. stability), provided that the polypeptide exhibits the same or increased immunogenicity to Arginase2, as compared to a polypeptide having the unmodified sequence:

a) Replacement of the C terminal amino acid with the corresponding amide (may increase resistance to carboxypeptidases);
b) Replacement of the N terminal amino acid with the corresponding acylated amino acid (may increase resistance to aminopeptidases);
c) Replacement of one or more amino acids with the corresponding methylated amino acids (may improve proteolytic resistance);
d) Replacement of one or more amino acids with the corresponding amino acid in D-configuration (may improve proteolytic resistance).

Any polypeptide disclosed herein may have attached at the N and/or C terminus at least one additional moiety to improve solubility, stability and/or to aid with manufacture/isolation, provided that the polypeptide exhibits the same or increased immunogenicity to Arginase2, as compared to a polypeptide lacking the additional moiety. Suitable moieties include hydrophilic amino acids. For example, the amino acid sequences KK, KR or RR may be added at the N terminus and/or C terminus. Other suitable moieties include Albumin or PEG (Polyethylene Glycol).

A polypeptide as disclosed herein may be produced by any suitable means. For example, the polypeptide may be synthesised directly using standard techniques known in the art, such as Fmoc solid phase chemistry, Boc solid phase chemistry or by solution phase peptide synthesis. Alternatively, a polypeptide may be produced by transforming a cell, typically a bacterial cell, with a nucleic acid molecule or vector which encodes said polypeptide.

The invention provides nucleic acid molecules and vectors which encode a polypeptide of the invention. The invention also provides a host cell comprising such a nucleic acid or vector.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences, for example in an expression vector. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides can be synthesised according to methods well known in the art, as described by way of example in Sambrook et al (1989, Molecular Cloning—a laboratory manual; Cold Spring Harbor Press). The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express a polypeptide of the invention. Such cells typically include prokaryotic cells such as bacterial cells, for example E. coli. Such cells may be cultured using routine methods to produce a polypeptide of the invention.

The polypeptide of the invention may be in a substantially isolated form. It may be mixed with carriers, preservatives, or diluents (discussed below) which will not interfere with the intended use, and/or with an adjuvant (also discussed below) and still be regarded as substantially isolated. It may also be in a substantially purified form, in which case it will generally comprise at least 90%, e.g. at least 95%, 98% or 99%, of the protein in the preparation.

Compositions Comprising Polypeptides

In another aspect, the present invention provides a composition comprising a polypeptide of the invention. For example, the invention provides a composition comprising one or more polypeptides of the invention, and at least one pharmaceutically acceptable carrier, preservative or excipient. The carrier, preservative and excipient must be 'acceptable' in the sense of being compatible with the other ingredients of the composition and not deleterious to a subject to which the composition is administered. Typically, all components and the final composition are sterile and pyrogen free. The composition may be a pharmaceutical composition. The composition may preferably comprise an adjuvant.

Adjuvants are any substance whose admixture into the composition increases or otherwise modifies the immune response elicited by the composition. Adjuvants, broadly defined, are substances which promote immune responses. Adjuvants may also preferably have a depot effect, in that they also result in a slow and sustained release of an active agent from the administration site. A general discussion of adjuvants is provided in Goding, Monoclonal Antibodies: Principles & Practice (2nd edition, 1986) at pages 61-63.

Adjuvants may be selected from the group consisting of: AlK(SO4)2, AlNa(SO4)2, AlNH4 (SO4), silica, alum, Al(OH)3, Ca3 (PO4)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80.RTM. emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in

*Corynebacterium parvum, Bordetella pertussis*, and members of the genus Brucella, Titermax, ISCOMS, Quil A, ALUN (see US 58,767 and U.S. Pat. No. 5,554,372), Lipid A derivatives, choleratoxin derivatives, HSP derivatives, LPS derivatives, synthetic peptide matrixes or GMDP, Interleukin 1, Interleukin 2, Montanide™ ISA-51 and QS-21. Various saponin extracts have also been suggested to be useful as adjuvants in immunogenic compositions. Granulocyte-macrophage colony stimulating factor (GM-CSF) may also be used as an adjuvant.

Preferred adjuvants to be used with the invention include oil/surfactant based adjuvants such as Montanide™ adjuvants (available from Seppic, Belgium), preferably Montanide™ ISA-51. Other preferred adjuvants are bacterial DNA based adjuvants, such as adjuvants including CpG oligonucleotide sequences. Yet other preferred adjuvants are viral dsRNA based adjuvants, such as poly 1:C. GM-CSF and imidazoquinolines are also examples of preferred adjuvants.

The adjuvant is most preferably a Montanide™ ISA adjuvant. The Montanide™ ISA adjuvant is preferably Montanide™ ISA 51 or Montanide™ ISA 720.

In Goding, Monoclonal Antibodies: Principles & Practice (2nd edition, 1986) at pages 61-63 it is also noted that, when an antigen of interest is of low molecular weight, or is poorly immunogenic, coupling to an immunogenic carrier is recommended. A polypeptide of the invention may therefore be coupled to a carrier. A carrier may be present independently of an adjuvant. The function of a carrier can be, for example, to increase the molecular weight of a polypeptide fragment in order to increase activity or immunogenicity, to confer stability, to increase the biological activity, or to increase serum half-life. Furthermore, a carrier may aid in presenting the polypeptide or fragment thereof to T-cells. Thus, in the composition, the polypeptide may be associated with a carrier such as those set out below.

The carrier may be any suitable carrier known to a person skilled in the art, for example a protein or an antigen presenting cell, such as a dendritic cell (DC). Carrier proteins include keyhole limpet hemocyanin, serum proteins such as transferrin, bovine serum albumin, human serum albumin, thyroglobulin or ovalbumin, immunoglobulins, or hormones, such as insulin or palmitic acid. Alternatively the carrier protein may be tetanus toxoid or diphtheria toxoid. Alternatively, the carrier may be a dextran such as sepharose. The carrier must be physiologically acceptable to humans and safe.

If the composition comprises an excipient, it must be 'pharmaceutically acceptable' in the sense of being compatible with the other ingredients of the composition and not deleterious to the recipient thereof. Auxiliary substances, such as wetting or emulsifying agents, pH buffering substances and the like, may be present in the excipient. These excipients and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Formulation of a suitable composition can be carried out using standard pharmaceutical formulation chemistries and methodologies all of which are readily available to the reasonably skilled artisan. Such compositions may be prepared, packaged, or sold in a form suitable for bolus administration or for continuous administration. Injectable compositions may be prepared, packaged, or sold in unit dosage form, such as in ampoules or in multi-dose containers optionally containing a preservative. Compositions include, but are not limited to, suspensions, solutions, emulsions in oily or aqueous vehicles, pastes, and implantable sustained-release or biodegradable formulations. In one embodiment of a composition, the active ingredient is provided in dry (for e.g., a powder or granules) form for reconstitution with a suitable vehicle (e. g., sterile pyrogen-free water) prior to administration of the reconstituted composition. The composition may be prepared, packaged, or sold in the form of a sterile injectable aqueous or oily suspension or solution. This suspension or solution may be formulated according to the known art, and may comprise, in addition to the active ingredient, additional ingredients such as the adjuvants, excipients and auxiliary substances described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. Alternatively, the active ingredients of the composition may be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

Methods of Use

The polypeptide or composition of the invention may be used in a method of treating or preventing a disease or condition in a subject. The polypeptide or composition of the invention may be used in the manufacture of a medicament for use in a method of treating or preventing a disease or condition in a subject. The method comprises administering to the said subject the said polypeptide or the said composition. Administration may be of a therapeutically or prophylactically effective quantity of the said polypeptide or the said composition, to a subject in need thereof.

The disease or condition may be characterized at least in part by inappropriate or excessive immune suppressive function of Arginase2. The disease or condition may be a cancer, preferably a cancer which expresses Arginase2 and/ or which is associated with inappropriate or excessive immune suppressive function of Arginase2. The cancer may be a cancer of the kidney, prostate, breast, brain, head and neck, or small intestine, or may be a colorectal or gastric cancer, or may be a melanoma, or may be a leukemia, preferably acute myeloid leukemia (AML) or Chronic lymphocytic leukemia (CLL). The cancer may be resistant to other cancer therapies, in particular it may be resistant to immune system checkpoint inhibitors such as anti-PD1 therapy.

The method may comprise simultaneous or sequential administration with an additional cancer therapy. The additional cancer therapy may be selected from a cytokine therapy, a T-cell therapy, an NK therapy, an immune system checkpoint inhibitor, chemotherapy, radiotherapy, immunostimulating substances (such as an additional vaccine), or gene therapy.

Immune system checkpoint inhibitors are particularly preferred as an additional cancer therapy. Vaccination against Arginase2 may have a synergistic effect when combined with inhibition of an immune system checkpoint. Examples of immune system checkpoints include:

a) The interaction between Indoleamine 2,3-dioxygenase (IDO1) and its substrate;
b) The interaction between PD1 and PDLL and/or PD1 and PDL2;
c) The interaction between CTLA4 and CD86 and/or CTLA4 and CD80;
d) The interaction between B7-H3 and/or B7-H4 and their respective ligands;
e) The interaction between HVEM and BTLA;
f) The interaction between GAL9 and TIM3;
g) The interaction between MHC class I or II and LAG3; and
h) The interaction between MHC class I or II and KIR.

Inhibition of checkpoints (a), (b) and (c) is particularly preferred as an additional cancer therapy. A checkpoint inhibitor may be any immunomodulatory agent (such as an antibody) which blocks or inhibits an immune system checkpoint, or it may be an immunotherapeutic composition comprising a component of an immune system checkpoint, or an immunogenic fragment of said component, which stimulates targeting of the checkpoint by the immune system.

The additional cancer therapy may be an antibody.

The antibody may be Abagovomab, Abciximab,Actoxumab, Adalimumab, Adecatumumab, Afelimomab, Afutuzumab, Alacizumab pegol, ALD518, Alemtuzumab, Alirocumab, Altumomab pentetate, Amatuximab, Anatumomab mafenatox, Anrukinzumab, Apolizumab, Arcitumomab, Aselizumab, Atinumab, Atlizumab (=tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Elotuzumab Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab,Ganitumab, Gantenerumab, Gavilimomab, Gemtuzumab ozogamicin, Gevokizumab, Girentuximab,Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Obinutuzumab, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Sipilizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab (=tremelimumab), Tildrakizumab, Tigatuzumab, TNX-650, Tocilizumab (=atlizumab), Toralizumab, Tositumomab, Tralokinumab, Trastuzumab, TRBS07, Tregalizumab, Tremelimumab Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab Vesencumab, Visilizumab, Volociximab, Vorsetuzumab mafodotin, Votumumab, Zalutumumab, Zanolimumab, Zatuximab, Ziralimumab or Zolimomab aritox.

Preferred antibodies include Natalizumab, Vedolizumab, Belimumab, Atacicept, Alefacept, Otelixizumab, Teplizumab, Rituximab, Ofatumumab, Ocrelizumab, Epratuzumab, Alemtuzumab, Abatacept, Eculizumab, Omalizumab, Canakinumab, Meplizumab, Reslizumab, Tocilizumab, Ustekinumab, Briakinumab, Etanercept, Inlfliximab, Adalimumab, Certolizumab pegol, Golimumab, Trastuzumab, Gemtuzumab, Ozogamicin, Ibritumomab, Tiuxetan, Tostitumomab, Cetuximab, Bevacizumab, Panitumumab, Denosumab, Ipilimumab, Brentuximab and Vedotin.

Particularly preferred antibodies that may be used in the method of the invention include: daratumumab, nivolumab, pembrolizumab, avelumab, rituximab, trastuzumab, pertuzumab, alemtuzumab, cetuximab, panitumumab, tositumomab and ofatumumab. Daratumumab is especially preferred. Anti-PD1 antibodies such as nivolumab and pembrolizumab are also especially preferred.

The additional cancer therapy may be selected from the group consisting of Actimide, Azacitidine, Azathioprine, Bleomycin, Carboplatin, Capecitabine, Cisplatin, Chlorambucil, Cyclophosphamide, Cytarabine, Dauno-rubicin, Docetaxel, Doxifluridine, Doxorubicin, Epirubicin, Etoposide, Fludarabine, Fluor-ouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine.

The polypeptide or composition of the invention may also be used in a method of stimulating arginase1-specific T cells, such as CD4 and CD8 T-cells, comprising contacting cells with the said polypeptide or composition. The method may be conducted ex vivo. The cells may be present in a sample taken from a healthy subject or from a cancer patient, such as in a tumour sample.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXAMPLE 1

Materials and Methods

Patient Material

PBMCs from healthy donors were isolated using density gradient separation over Lymphoprep™ (STEMCELL Technologies) and cryopreserved at −150° C. in FBS supplemented with 10% DMSO. PBMCs from cancer patients were isolated from blood sample a minimum of four weeks after the termination of any anti-cancer therapy. The protocol was approved by the Scientific Ethics Committee for The Capital Region of Denmark and conducted in accordance with the provisions of the Declaration of Helsinki. Written informed consent from the patients was obtained before study entry.

Peptides

Peptides were synthesized by standard methods and provided dissolved in DMSO to obtain a stock concentration of 10 mM. The sequences of the peptides used in these experiments are shown in the section entitled "Sequences"). Peptides are described by SEQ ID NO, by name, or by reference to the start and end positions of each peptide sequence within the full length sequence of Arginase2. Each may be used interchangeably. For example, the peptide of SEQ ID NO: 2 may alternatively be referred to by the name Arg2_1, or may alternatively be referred to as Arg2 aa11-30 (given a start position of 11 and end position of 30). The intended reference in each case will be clear from the context.

ELISPOT Assay

For in vitro ELISPOT, PBMCs from cancer patients and healthy donors were pulsed with 20 µM of arginase1-derived peptides (or with no peptide as a control) and 120 U/ml IL-2 in 24-well plates for 7 days before being used in an ELISPOT assay. The cells were placed in 96-well nitrocellulose ELISPOT plates (MultiScreen MAIP N45; Millipore) pre-coated with IFNγ capture antibody (Mabtech). Arginase peptides added to a final concentration of 5 µM and plates incubated at 37° C. for 14-16 hours. After the incubation the cells were washed off and secondary biotinylated Ab (Mabtech, cat. 3420-{6-1000) was added for 2 hours at room temperature. Unbound secondary antibody was washed off and streptavidin conjugated alkaline phosphatase (AP) (Mabtech, cat. 3310-10) was added for 1 hour at room temperature. Unbound conjugated enzyme was washed off and the assay was developed by adding BCIP/NBT substrate (Mabtech, cat. 3650-10). Developed ELISPOT plates were analyzed on CTL ImmunoSpot S6 Ultimate-V analyzer using Immunospot software v5.1. Responses were reported as the difference between average numbers of spots in wells stimulated with arginase2 and wells without added peptide.

Intracellular Staining

Intracellular staining of cell cultures was performed after PBMCs were stimulated with arginase-derived peptides (or incubated with no peptide as a control) for 5 hours in the presence of BD GolgiPlug™ (added after the first hour of peptide stimulation). Stimulated cells were stained with fluorescently labeled antibodies for surface markers (CD3, CD4, CD8) and thereafter permeabilized by using Fixation/Permeabilization and Permeabilization Buffer (eBioscience, cat. 00-{5123-43), according to manufacturer's instructions. Permeabilized cells were then stained with fluorochrome-labeled antibodies for IFNγ and TNFα. Flow cytometry analysis was performed on a FACSCanto™ II (BD Biosciences). Antibodies used: IFNγ-APC (cat.341117), TNFα-455 BV421 (cat.562783), CD4-FITC (cat.347413), CD8-PerCP (cat.345774), CD3-APC-H7 (cat. 560275) (all from BD Biosciences), dead cells stain-FVS510 (564406, BD Biosciences) according to manufacturer's instructions.

Results

Screening for Arginase2 Peptides Based on the Arginase1 Hotspot

Based on the previously identified 50-amino acid long Arginase1 hotspot region at positions 161-210 of Arginase1, four peptides that cover the corresponding region in Arginase2 (positions 180-229) were chosen for testing. These peptides are Arg2-E17 (aa180-199), Arg2-E18 (aa190-209), Arg2-E19 (aa200-219) and Arg2-E20 (210-229)—see FIG. 1 for schematic representation relative to Arginase1 and Arginase2. Arg2-E17 could not be synthesised by routine methods, and so the experiment was conducted with the remaining three peptides.

To test whether these peptides could be used to identify Arginase2 responses, PBMCs from 12 healthy donors and one cancer patients were screened for responses in IFNγ ELISPOT. PBMCs were stimulated with Arginase2 peptides and low dose IL-2 for 1 week prior to ELISPOT.

As is shown in FIG. 2, the peptides were all recognised by PBMCs from at least one subject. Arg2-E18 showed the highest and most consistent response.

Peptide Library Screening for Other Arginase2 Peptides

The entire arginase2 protein sequence was divided into overlapping 20-amino-acid-long peptides (with a final peptide of 24 amino acids), generating a library of 34 peptides covering the whole sequence (SEQ ID NOs 1-34)). Each peptide in the library overlapped with the first 10 amino acids of the following peptide. Using this arginase2 peptide library and the IFNγ ELISPOT assay, we next screened PBMCs from 6 healthy donors for spontaneous responses. The PBMCs were stimulated for one week with a pool of 3-4 adjacent 20-mer arginase2 library peptides and low-dose IL-2 (120 U/mL). They were then set up for an IFNγ ELISPOT assay to screen for responses against each 20-mer peptide separately.

Figure 3:
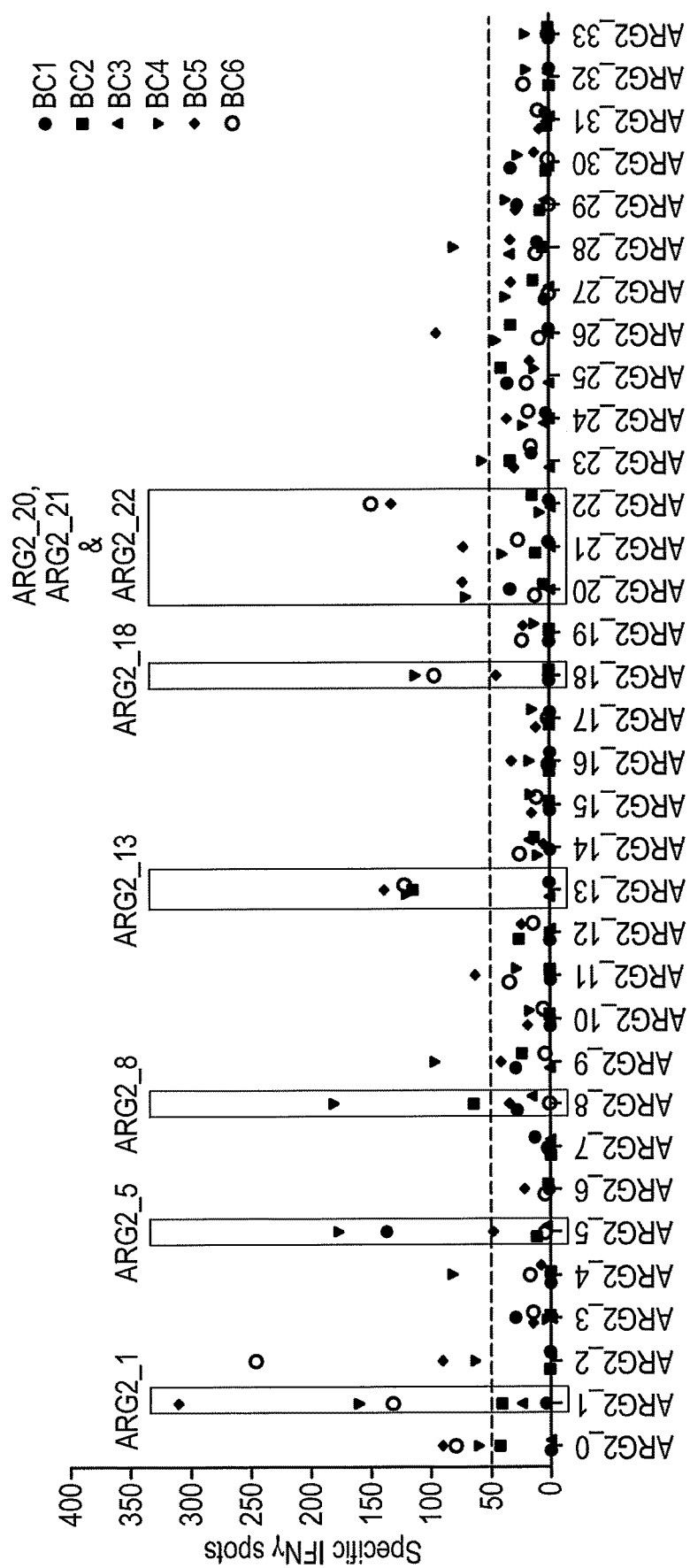
FIG. 3 shows that multiple ARG2 library peptides are recognized by PBMCs from healthy donors. Spot counts are given as a difference between averages of the wells stimulated with peptide and control wells without peptide. $4-4.5*10^5$ cells were plated pr. well and peptide and control stimulations were performed in triplicates. Boxes denote peptides that shows the highest and most abundant responses after screening of 6 healthy donors.

As is shown in FIG. 3, the following eight peptides showed the highest and most abundant responses:

ARG2_1 (aa11-30), ARG2_5 (aa51-70), ARG2_8 (aa81-100), ARG2_13 (aa131-150), ARG2_18 (181-200), ARG2_20 (201-220), ARG2_21 (aa211-230) and ARG2_22 (221-240).

Arg2_18, Arg2_20, Arg2_21 and Arg2_22 are all contained within or overlapping with the previously identified hotspot region. However, the other peptides (including the peptide with the highest responses, Arg2_1) are from different regions of the Arginase2 protein.

Validation of Library Screen (Hotspot Region)

PBMCs from two healthy donors were stimulated for one week with a single peptide and low-dose IL-2 (120 U/mL) before IFNy ELISPOTassay to validate the responses observed in the library screen.

ARG2_18, ARG2_19, ARG2_20 and ARG2_21 were each tested in this validation experiment, with ARG2-E18, ARG2-E19 and ARG2-E20 also included since they overlap with the same region of Arginase2. Arg2-E17 was again excluded because it could not be synthesized by routine methods.

The six tested peptides are shown below in alignment:

| | | |
|---|---|---|
| FSWIKPCISSASIVYIGLRD-------------------------- | Arg2_18 | SEQ ID 19 |
| ----------ASIVYIGLRDVDPPEHFILK------------------ | Arg2_19 | SEQ ID 20 |
| ---------SASIVYIGLRDVDPPEHFIL------------------- | Arg2-E18 | SEQ ID 36 |
| -----------------VDPPEHFILKNYDIQYFSMR---------- | Arg_20 | SEQ ID 21 |
| -----------------DVDPPEHFILKNYDIQYFSM---------- | Arg2-E19 | SEQ ID 37 |
| --------------------------NYDIQYFSMRDIDRLGIQKV | Arg2_21 | SEQ ID 22 |
| -------------------------KNYDIQYFSMRDIDRLGIQK- | Arg2-E20 | SEQ ID 38 |

Figure 4:
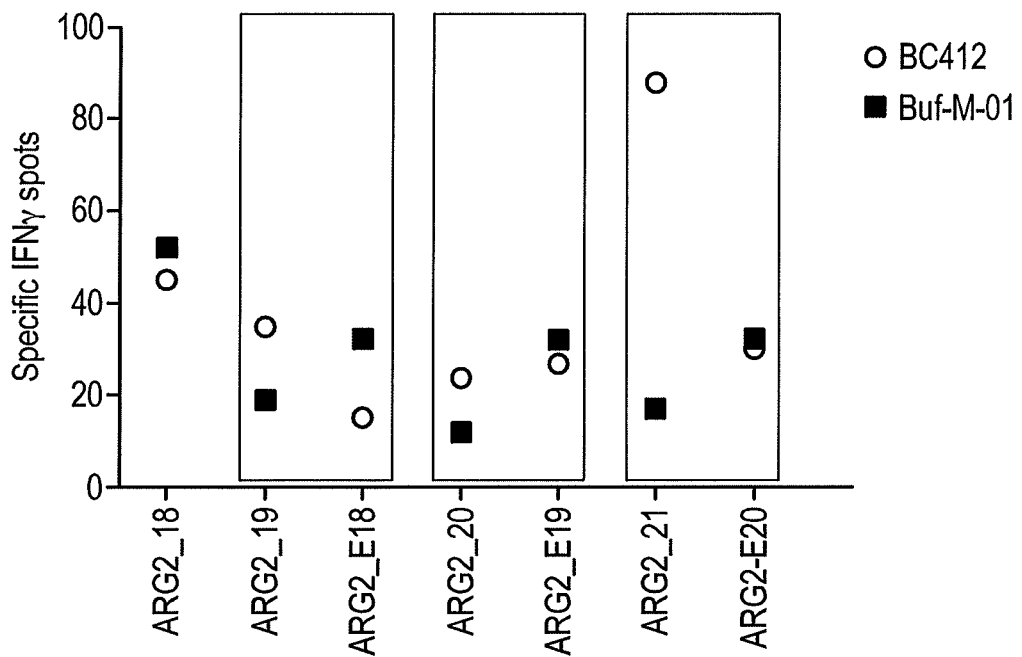
FIG. 4 validates the responses to hotspot region peptides. Spot counts are given as a difference between averages of the wells stimulated with peptide and control wells without peptide. $5*10^5$ cells were plated pr. well and peptide and control stimulations were performed in triplicates. Boxes indicate peptides that have almost identical sequences for easier comparison of the responses obtained.

As shown in FIG. 4, responses to each of the tested peptides were observed, validating the original screens. Overlapping pairs of peptides produced almost identical responses, except for ARG2_21 and ARG2-E20 where a stronger response was observed in one healthy donor against ARG2_21. The strongest and most consistent responses in this experiment were obtained with ARG2_18.

Validation of Library Screen (Other Regions)

Figure 5:
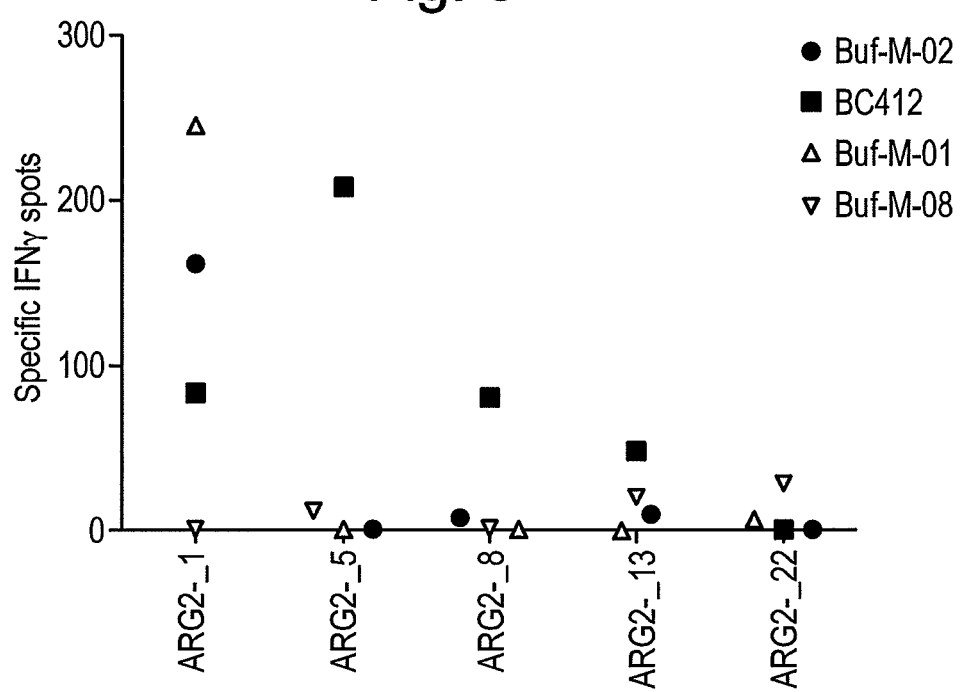
FIG. 5 shows validation of responses to ARG2_1, ARG2_5, ARG2_8, ARG2_13 and ARG2_22. Spot counts are given as a difference between averages of the wells stimulated with peptide and control wells without peptide. $3*10^5$ cells were plated pr. well with and without peptide stimulations, performed in triplicates. Strong and prominent responses were observed against ARG2_1.

PBMCs from four healthy donors were stimulated for one week with a single peptide and low-dose IL-2 (120 U/mL) before IFNy ELISPOTassay to validate the responses observed in the library screen. ARG2_1, ARG2_5, ARG2_13, ARG2_18 and ARG2_22 were tested in this validation. As shown in FIG. 5, strong and prominent responses were observed against Arg2_1 in particular.

Figure 6B:
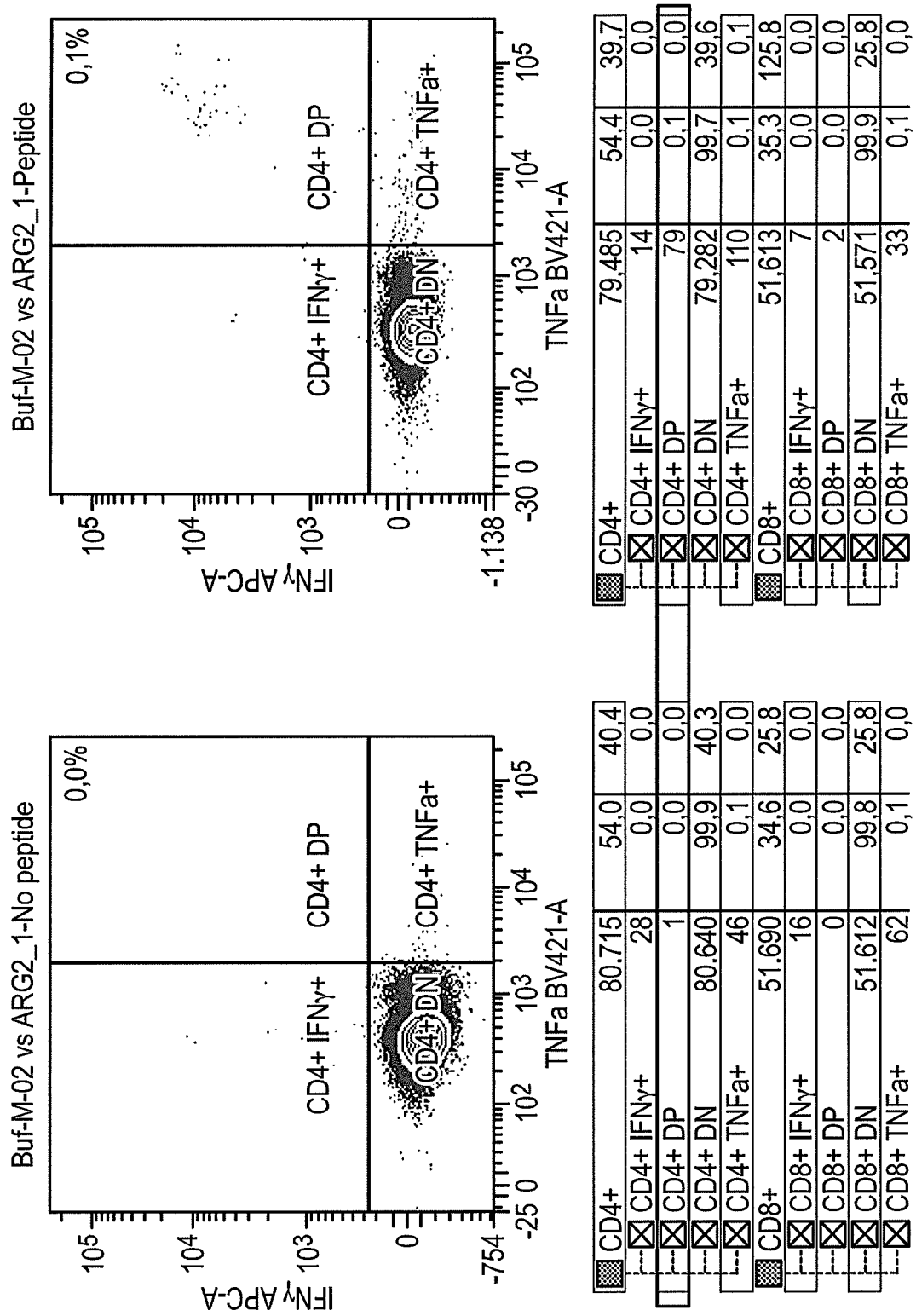

An intracellular cytokine staining assay was thus used on the same cells to elucidate whether CD4+ or CD8+ responses were present. For two healthy donors, Buf-M-01 and Buf-M-02, 0.2% and 0.1% double positive (DP) CD4+ cells were observed (see representative plots in FIGS. 6A and 6B), suggesting a CD4+ response against ARG2_1 in these donors.

Further Screening of Cancer Patients and Healthy Donors for Responses to ARG2_1

ARG2_1 was used to screen for responses in 8 melanoma patients (AA07-AA31), 4 prostate cancer patients (UR07-27) and 13 healthy donors. PBMCs from each were stimulated for one week with a single peptide and low-dose IL-2 (120 U/mL) before IFNy ELISPOT assay.

Figure 8:
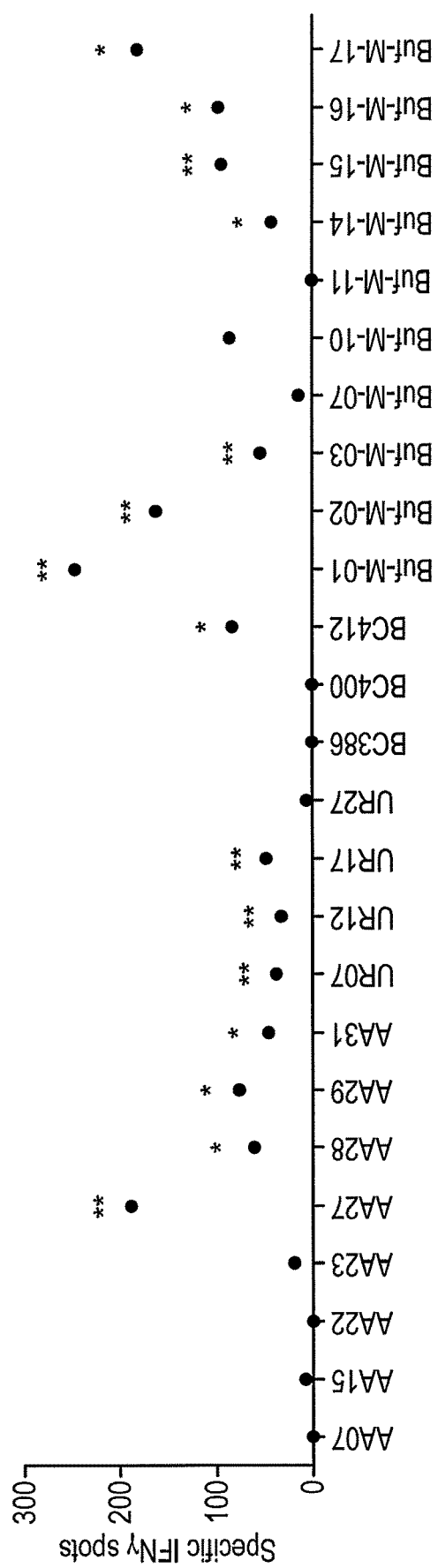
FIG. 8 shows that ARG2 peptides corresponding to the hotspot region are recognized by PBMCs from healthy donors (BC or Buf-M) and cancer patients (AA, melanoma; UR, renal cell carcinoma). Spot counts are given as a difference between averages of the wells stimulated with peptide and control wells without peptide. $4*10^5$ cells were plated pr. well and peptide and control stimulations were performed in triplicates. Responses were analyzed using distribution free resampling (DFR) rule. *-$p\leq0.05$, **-$p\leq0.01$.

As shown in FIG. 8, significant responses were seen in 15 out of 25 donors tested (60%) and the responses seems to be almost equally strong in patients and healthy donors.

Figure 9:
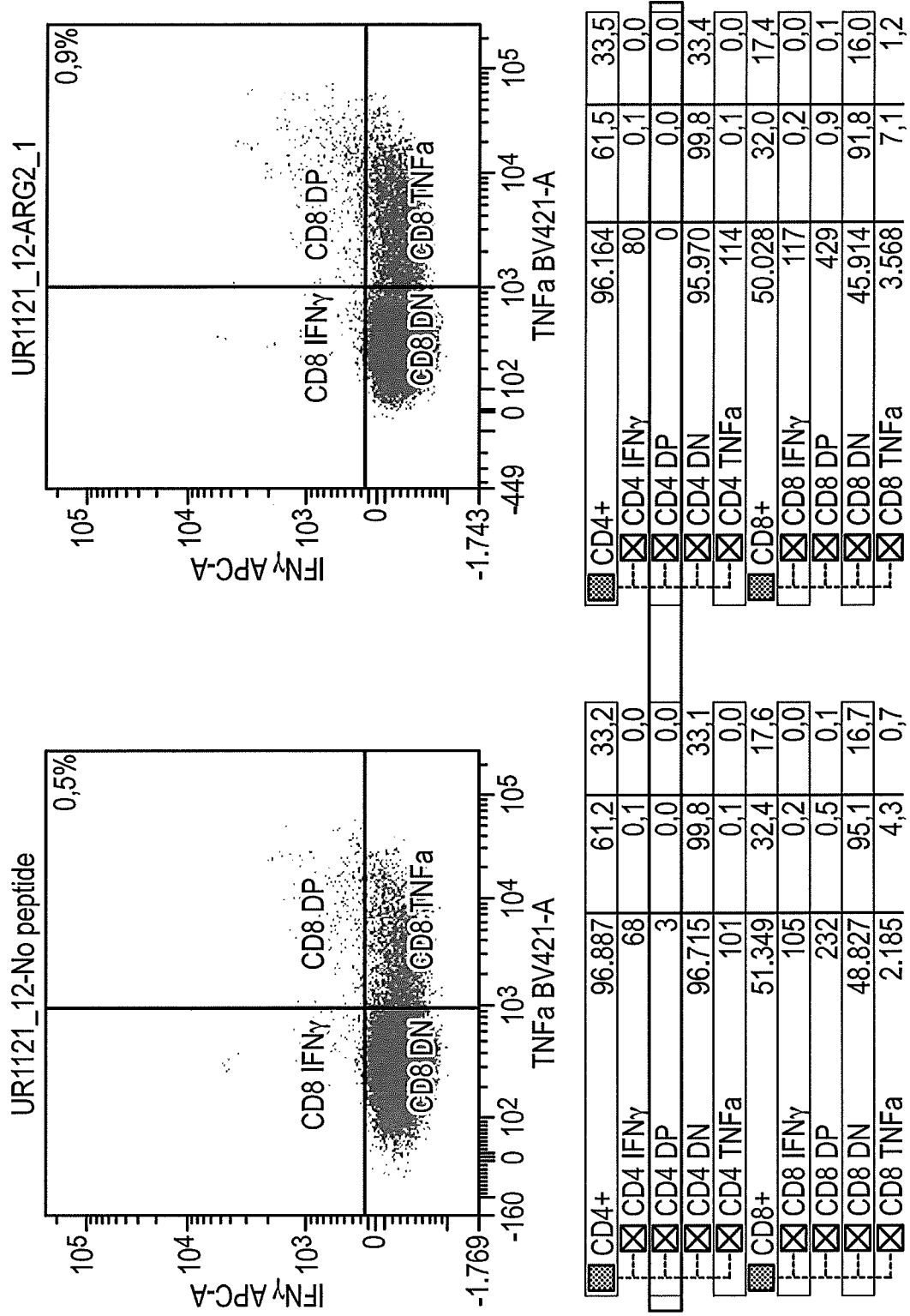
FIG. 9 shows CD8+ T cell responses in one cancer patient to ARG2_1 or with no peptide. PBMC cells were stained with CD8 antibody and analyzed in an intracellular cytokine release assay by flow cytometry with or without ARG2_1 stimulation. It can be seen from the figure that the CD8+ T cells release more of IFN-gamma (y-axis) and TNF-alfa (x-axis) when stimulated with the ARG2-derived peptide even though some background release of TNF-alfa was observed.

PBMCs that showed clear responses in IFNy ELISPOT were also used for intracellular cytokine staining. We analyzed CD4 cells from two healthy donors and showed that in these two donors CD4 cells were reacting specifically to the ARG2_1. In addition, we found that among PBMC from a prostate cancer patient (UR12) there were also a CD8+ response to ARG2_1 (0.9% CD8+ DP cells vs. 0.5% for control)—see FIG. 9. Taken together, these ICS results show that the detected ARG2_1 responses are T-cell mediated, and furthermore, may be mediated by both CD4 and CD8 T cells.

Prediction for HLA-A2 and HLA-A3 epitopes within ARG2_1 was therefore conducted using the www.syfpeithi.de server. The following epitopes were predicted as present within the ARG2_1 sequence:

| | | |
|---|---|---|
| HLA-A3_decamer | -ILKKSVHSVA | Score = 20 |
| HLA-A2_nonamer | -ILKKSVHSV- | Score = 28 |
| HLA-A2_decamer | SILKKSVHSV- | Score = 29 |

All three predicted epitopes incorporate the transit peptide boundary at positions 21, 22 and 23 of SEQ ID NO: 51

Responses to ARG2_1 Are Also Observed Without Pre-Stimulation ("Ex Vivo ELISPOT")

Figure 10:
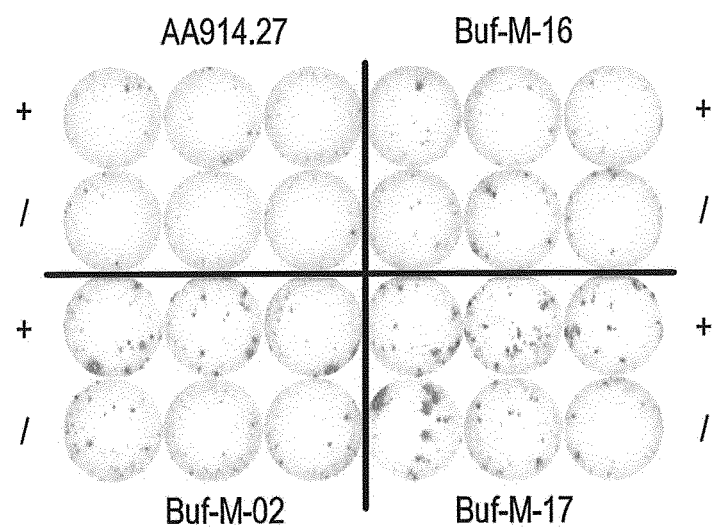
FIG. 10 shows ex vivo ELISPOT responses toward ARG2_1 after no pre-stimulation but 72 hrs incubation+/−peptide in the ELISPOT plate. $9*10^5$ cells were plated pr. well with and without (control) peptide ARG2_1, performed in triplicates. Spot counts are given as averages of the wells stimulated with peptide and control wells without peptide.
Figure 10:
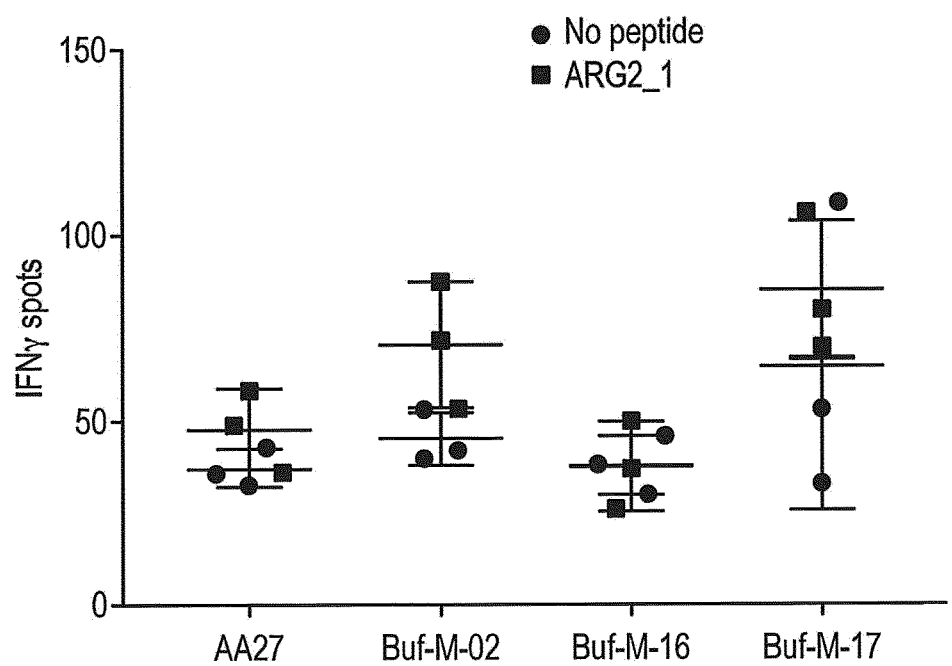

A cancer patient and three healthy donors that had shown strong responses in the previous experiments (which are in vitro or "indirect" IFNy ELISPOTs) were also tested in an ex vivo ELISPOT. This means that the PBMCs are not pre-stimulated but are simply incubated +/−Arg2_1 peptide for 72 hours prior to the IFNy ELISPOTassay. As shown in FIG. 10, responses to ARG2_1 were detected. The fact that specific T-cell responses were directly detectable ex vivo is especially noteworthy. With very few exceptions it is not normally possible to detect tumor associated antigen-specific T cells either by tetramer stainings or by ELISPOT in PBMC directly ex vivo without prior in vitro peptide stimulation. It is very unusual to be able to detect immune response against non-viral antigens without a pre-stimulation step in vitro. As such, these results underline the high immunogenicity of the ARG2_1 sequence and the epitopes comprised within it. Such sequences are therefore a good vaccination target since the data implies that the immune system can selectively target Arginase2-expressing cells, reducing the immunomodulatory effect of Arginase expression and thereby enhancing anti-tumor immune responses. Furthermore, these data suggest that Arginase2-specific T cells (particularly those which recognise epitope(s) within ARG2_1) play a natural role in the immune system. This implies that vaccination against such sequences will most likely not induce toxicities in patients.

Discussion

The presence of arginase2-expressing cells in a cancer contributes to an immunosuppressive tumor microenvironment that prevents proliferation of cancer-specific effector lymphocytes. Specifically targeting such arginase2-expressing cells (which may include tumor cells as well as other regulatory cells) will therefore have a direct benefit and an indirect benefit by reducing the immunosuppressive effect, permitting the activation and proliferation of cancer-specific effector cells. Given that anti-cancer immunotherapy is often antagonized by immune-suppressive cells, this dual effect of targeting Arginase2 epitopes could be highly synergistic. Given that these experiments have shown that natural CD4 and CD8 T-cell mediated immunity towards Arginase2 exists (particularly for epitopes within the Arg2_1 sequence), there is a high likelihood for success in targeting Arginase2 in a vaccination setting.

EXAMPLE 2-FURTHER INVESTIGATION OF HUMAN ARG2 PEPTIDES

Materials and Methods

Patient Material

PBMCs from healthy donors were isolated using density gradient separation over Lymphoprep™ (Alere) and cryo-preserved at −150° C. in FBS (Life Technologies) supplemented with 10% DMSO. PBMCs from cancer patients with were isolated from blood sample a minimum of four weeks after the termination of any anti-cancer therapy. PBMCs from patients with AML were isolated from blood sample from patients at different disease and treatment status, thus including patients in therapy. All protocols were approved by the Scientific Ethics Committee for The Capital Region of Denmark and conducted in accordance with the provisions of the Declaration of Helsinki. Written informed consent from the patients was obtained before study entry. PMBCs were maintained in X-vivo (BioNordika) supplemented with 5% human serum (Sigma Aldrich).

Cell Culture

THP-1 were cultured in RPMI (Gibco) supplemented with 10% FBS. Set2 cells were cultured in RPMI with 20% FBS. OCI-AML-2 cells were cultured in Alpha-MEM (Life Technologies) with 10% FBS. MONO-MAC-1 cells were cultured in RPMI supplemented with 10% FBS, 1 mM sodium pyruvate (Life Technologies), 2 mM L-glutamine (Life Technologies) and 1× non-essential amino acids (Life Technologies). All cell lines were tested and confirmed negative for mycoplasma. Cells were passaged 2-3 times a week.

Cytokine stimulation with IL-4 (400 U/ml), IL-13 (50 ng/ml), IFNy (100 U/ml) or cytokine cocktail (400 U/ml IL-4, 1000 U/ml GM-CSF and 1000 U/ml TNFa) was done by seeding of 0.5-0.75×10$^6$ cell/mL medium supplemented with the respective cytokines and 48 hrs of incubation before cells were harvested for various experiments. All cytokines are from Trichem.

Peptides

The ARG2 peptide library of 34 20 mer peptides was synthesized by PepScan and dissolved in DMSO at 10 mM for screening for immune responses. For remaining experiments, ARG2-1 was dissolved in sterile water at 2 mM. Long ARG2 peptides (A2L1, A2L2, A2L3 (SEQ ID NOs: 58, 59, 57) were synthesized by Schafer and dissolved at 2 mM in sterile water. Peptides dissolved in sterile water was filtered through a 0.22 µm filter before use. Purity of the synthesized peptides were >90%. For a list of all peptides, see Table 1.

Peptide Stimulation and ELISPOT Assay

PBMCs from healthy donors or cancer patients were stimulated with 10 µM of ARG2-derived peptides in vitro to enhance assay sensitivity. On day 2, IL-2 was added to a total of 120 U/ml IL-2 (Novartis). After 7 days, 4-6×10$^5$ PBMCs were placed at the bottom of an ELISPOT plate pre-coated with IFNy capture antibody (Mabtech). PBMCs from each donor or patient were set up in triplicates or quadruplicates for peptide (5 µM ARG2-derived peptide) and control stimulations. Cells were incubated in ELISPOT plates in the presence of an antigen for 14-16 hrs after which they were washed off and secondary biotinylated antibody (Mabtech) was added. After two hour incubation the secondary antibody was washed off before addition of streptavidin conjugated alkaline phosphatase (Mabtech) for 1 hr. Next, unbound enzyme was washed off and the assay was developed by adding BCIP/NBT substrate (Mabtech). Developed ELISPOT plates were analyzed on CTL Immunospot S6 Ultimate-V analyzer with ImmunoSpot software, version 5.1. Responses are reported as the difference between average number of spots in well stimulated with ARG2-derived peptides and control wells.

ELISPOT assays with ARG2-specific T cells (effector cells) and various immune or cancer cells as target cells (target cells) were setup by placing 1-5×10$^4$ effector cells (as indicated) and 1-2.5×10$^4$ target cells (as indicated) in the bottom of an ELISPOT well. Peptide pulsing of target cells were performed by incubation of cells with 20 µM peptide for 1hr followed by two washes to remove unbound peptide. These cells served as positive control. Effector cells plated without target cells served as negative control. All conditions were setup in triplicates or quadruplicates.

Intracellular Cytokine Staining Assay

Intracellular staining of cell cultures was performed on PBMCs after one week of ARG2-derived peptide stimulation in vitro. For the assay, 9×10$^5$ PBMCs were re-stimulated with ARG2-derived peptides (or incubated with no peptide as a control) for 5 hours in the presence of BD GolgiPlug™ (added after the first hour of peptide stimulation). Stimulated cells were stained with fluorescently labeled antibodies for surface markers (CD3, CD4, CD8) and thereafter permeabilized by using Fixation/Permeabilization and Permeabilization Buffer (eBioscience, cat. 00-{5123-43), according to manufacturer's instructions. Permeabilized cells were then stained with fluorochrome-labeled antibodies for IFNγ and TNFα. Flow cytometry analysis was performed on a FACSCanto™ II (BD Biosciences). Antibodies used: IFNγ-APC, TNFα-BV421, CD4-PerCP, CD8-FITC, CD3-APC-H7, CD4-FITC, CD8-PerCP, and dead cells stain-FVS510 (all from BD Biosciences) according to manufacturer's instructions. For intracellular cytokine staining to detect cytokine production of ARG2-specific T cells in response to target cells, 5×10$^5$ ARG2 specific cells were incubated with 2.5×10⁵ target cells for 5 hours with GolgiPlug™ added after the first hour.

Establishment of ARG2-Specific T Cell Cultures

The ARG2-specific T cell culture was established by initial stimulation of PMBCs from a prostate cancer patient with irradiated ARG2-1 loaded autologous mature dendritic cells. The following day IL-12 (20 U/ml) and IL-7 (40 U/ml) was added. PBMCs were restimulated every 8 days with ARG2-1 peptide loaded autologous DCs followed by addition of IL-2 (120 U/ml) the next day. ARG2-specific T cells were enriched using IFNy enrichment kit (MiltenyiBiotec) after 4 stimulations. Cells were expanded and ARG2-specific T cells were further enriched using CD4+ enrichment kit (MiltenyiBiotec).

Production of In-Vitro Transcribed mRNA

The cDNA encoding ARG2 (NM 001172.4) was synthesized and cloned into the HLA Class II targeting plasmid pGEM-sig-DC.LAMP (kindly provided by Dr. K. Thielemans, Medical School of the Vrije Universiteit Brussel) using BamHI restriction sites. The pGEM-ARG2-DC-LAMP plasmid was linearized with Spel before serving as DNA template for in vitro transcription (ref to ÖM article**).

Total RNA Extraction

Cells were harvested, washed in PBS and pelleted by centrifugation. Cell pellets were kept on ice or frozen down at −80° C. until RNA extraction. Total RNA was extracted using the RNAeasy Plus Mini Kit (Qiagen) according to manufacturers instruction with final elution in 30 µl of RNA-free water. The RNA concentration was measured on the NanoDrop 2000 Spectrophotometer (Thermo Scientific). RNA was stored at −80° C.

RT-qPCR

Total RNA was reverse transcribed using the High Capacity cDNA Reverse Transcription Kit (Applied Biosystems). For each reaction, 1000 ng RNA was reverse transcribed. For RT-qPCR, the cDNA was diluted 1:5 and subjected to RT-qPCR analysis using the TaqMan Gene Expression Assay on the Roche Lightcycler 480 Instrument. RT-qPCRs were run in quadruplicates and data was analyzed using the ddCT-method with normalization to expression level of the house keeping gene RPLPO and control sample. For low concentration samples that were not amplified, Ct was set to 40. No-reverse transcriptase controls (cDNA reactions setup without reverse transcriptase) served as controls of specific amplification. A list of primers used in this study is found below.

| RT-qPCR PRIMERS | | |
|---|---|---|
| Gene name | Identifier | Source |
| ARG1 | Hs00163660_ml | Thermo Scientific |
| ARG2 | Hs00982833_ml | Thermo Scientific |
| RPLPO | Hs99999902_ml | Thermo Scientific |
| ACTB | Hs99999903_ml | Thermo Scientific |

Electroporation

For mRNA, DCs or cancer cells were transfected with ARG1-DC-LAMP mRNA, ARG2-DC-LAMP mRNA or control mRNA encoding eGFP using electroporation parameters as previously described. Briefly, cells were washed twice in Opti-MEM medium (Thermo Scientific) and adjusted to a final cell concentration of 9-12×10⁶ cells/ml. 350 µl cell suspension was preincubated on ice for 5 minutes before addition of 10 µg mRNA. The cell suspension was then quickly transferred into a 2-mm (cancer cells) or 4-mm (DCs) gap electroporation cuvette and electroporated (ref: OM paper). After electroporation, cells were quickly transferred to a dish with pre-warmed medium and incubated in humidified atmosphere with 5% CO2 before use for different experimental analysis. mRNA transfected cells were rested for 1 hr before they were setup in ELISPOT assay or rested overnight before set up in intracellular cytokine staining assay. Electroporation efficiency was determined 24 hours post transfection by FACS analysis of the GFP transfected cells.

siRNA Mediated ARG2 Silencing

A set of three siRNA duplexes targeting ARG2 was obtained from Ambion (ARG2 Silencer Select Validated siRNA, ID s1571, s1572, s1573). siRNAs were suspended in nuclease free water to 0.1 nmol stock solutions and stored at −80° C. For ARG2 silencing experiments, THP-1 cells were prepared for electroporation as described above and 10 µl of a working solution of 0.02 nmol siRNA solution was added of each of the three siRNA before transfection as previously described. Immediately after transfection, cells were transferred to pre-warmed medium and incubated for 1 hr. Transfected cells were then split in two and to half of the cells cytokine cocktail (400 U/ml IL-4, 1000 U/ml GM-CSF and 1000 U/ml TNFa) was added. Cells were incubated in medium or medium containing cytokine cocktail for 48 hrs before they were set up in intracellular cytokine staining assay. Cells were pelleted for RNA after 48 hrs for accession of knock down efficiency by RT-qPCR.

Flow Cytometric Analysis of HLA-DR Expression

HLA-DR expression analysis was performed on cells stimulated for 48 hrs with mock (no cytokines), IFNy (100U/ml) or cytokine cocktail (400U/ml IL-4, 1000 U/ml GM-CSF and 1000 U/ml TNFa). Briefly, cells were washed and stained with 7-AAD (cat: 51-68981E, BD Bioscience) and FITC-conjugated mouse anti-human HLA-DR, DP, DQ (cat: 5555581, BD Bioscience) or FITC-conjugated mouse IgG1 K isotype ctrl (FC) (cat: 400109, BD Bioscience) for 30 minutes at 4° C. Excess antibody was washed off before cells were analyzed on FACSCanto™ II instrument. HLA-DR expression levels is given as the difference in MFI between MHC Class II stained live cells and isotype control stained live cells.

Statistical Analysis

ELISPOT responses were analyzed using distribution free resampling (DFR) method. Statistical analysis of ELISPOT responses was performed using R studio. The difference in responses (specific IFNy-secreting cells) toward ARG2-1 and A2L2 were compared with the use of Wilcoxon matched pairs signed ranked t test (using Prism 8) with a significance level of 0.05. Statistical analysis of difference in average tumor growth between control and Arg2 vaccinated groups was performed by mixed effect analysis using Prism 8.

Results

Spontaneous Immune Responses Toward ARG2

As outlined in Example 1, ARG2-1 was found to give the highest and most frequent responses in the screened donors. Interestingly, ARG2-1 is a part of the transit sequence (aa1-22) of ARG2. Signal peptide sequences represent an interesting type of peptide epitopes that largely do not depend on proteosomal degradation or TAP for their processing and presentation in the context of HLA molecules. Furthermore, this part of ARG2 has almost no sequence overlap with the corresponding sequence of ARG1—see alignment below:

```
ARG1    MSAKS----------------RTIGIIGAPFSKGQPRGGVEEGPTVLRKAGLLE (SEQ ID 63)

ARG2    MSLRGSLSRLLQTRVHSILKKSVHSVAVIGAPFSQGQKRKGVEHGPAAIREAGLMK (SEQ ID 64)
```

ARG2-1 was therefore used to screen for ARG2 immune responses in 33 HDs and 19 cancer patients with solid tumors (11 melanoma, 7 prostate cancer, and 1 breast cancer patient) by IFNy ELISPOT assay. Strong and frequent responses were found in both healthy donors and cancer patients with solid tumors with significant responses in around 75% of the screened donors (See FIG. 14A—some data points in this figure are also present in FIG. 8).

Figure 14:
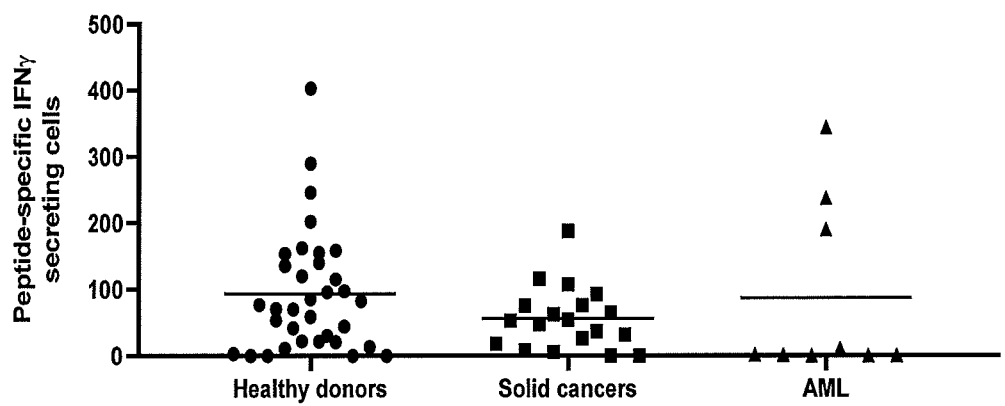
FIG. 14 shows that ARG2-1 is widely recognized by both PMBCs from both healthy donors and cancer patients with solid tumors or AML. (A) IFNy ELISPOT responses against ARG2-1 peptide in PMBCs from healthy donors (n=33), cancer patients with solid tumors (n=19) or cancer patients with AML (n=19). $3-4*10^5$ cells were plated pr. well. Peptide and control stimulations were performed in triplicates. Each spot represents one donor and is the number of peptide-specific IFNy secreting cells (the difference between the average of wells stimulated with peptide and control wells). (B) Representative intracellular cytokine staining for IFNy and TNFa production in healthy donors (HD49 and HD50) and cancer patients (AA27) with solid tumors stimulated with ARG2-1 or non-stimulated control.
Figure 14:
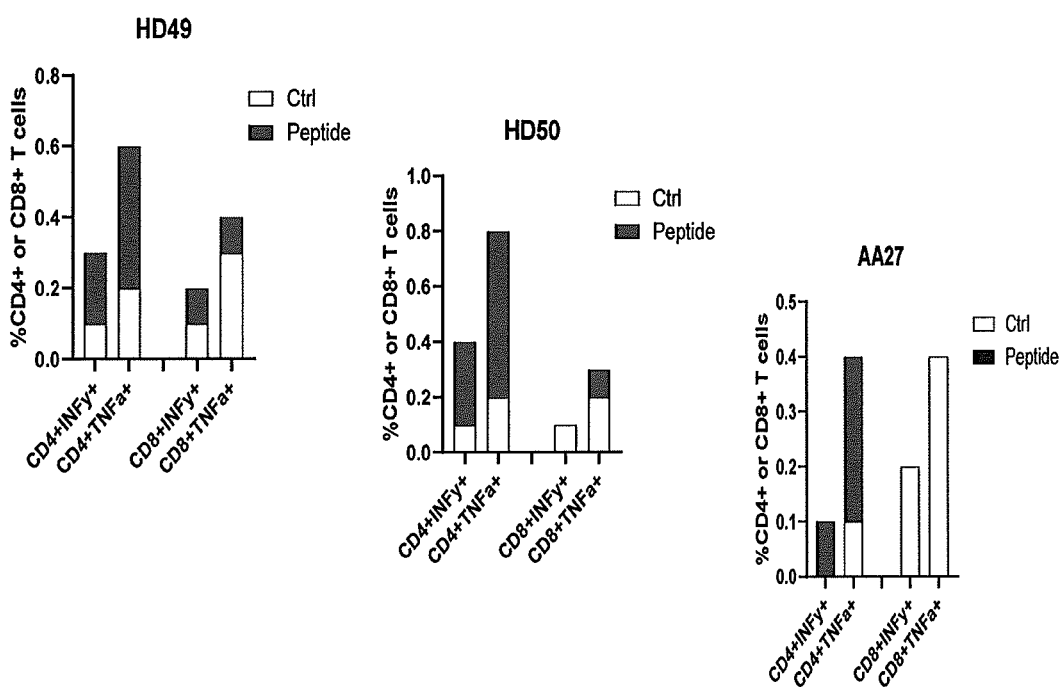

Since ARG2 is reported to play an important role in the immunosuppressive microenvironment observed in patients with Acute myeloid leukemia (AML), the potential presence of ARG2-specific T cells among PBMCs from patients diagnosed with AML was also investigated by IFNy ELISPOT. To this end, we collected peripheral blood from nine patients diagnosed with AML. Blood collection and subsequent PBMC isolation was performed independently of treatment status and the patients included thus represent very different disease- and treatment stages. A significant response was observed in 3 out of 9 patients tested (see FIG. 14A), suggesting that ARG2-specific T cells indeed can be present in AML patients. Intracellular cytokine staining for IFNy and TFNa production in healthy donors and cancer patients with solid tumors primarily showed CD4+ responses to ARG2-1 (FIG. 14B).

Characterization of Long ARG2 Peptide Epitopes

It has previously been demonstrated that a longer (38-mer) ARG1 peptide is superior at stimulating ARG1-specific T cells as compared to 20- and 30mer ARG1 peptides. To identify an optimal, promiscuous ARG2-derived epitope for the stimulation of ARG2-specific T cells in individuals independent of tissue type, longer ARG2 peptide epitope spanning larger parts of the sequence around ARG2-1 were therefore also designed based on HLA prediction algorithms (available at www.syfpeithi.de and cbs.dtu.dk). These sequences are shown below aligned with the predicted signal sequence of human Arginase 2 and with the 20mer sequences of ARG2-0, ARG2-1 and ARG2-2.

Figure 15:
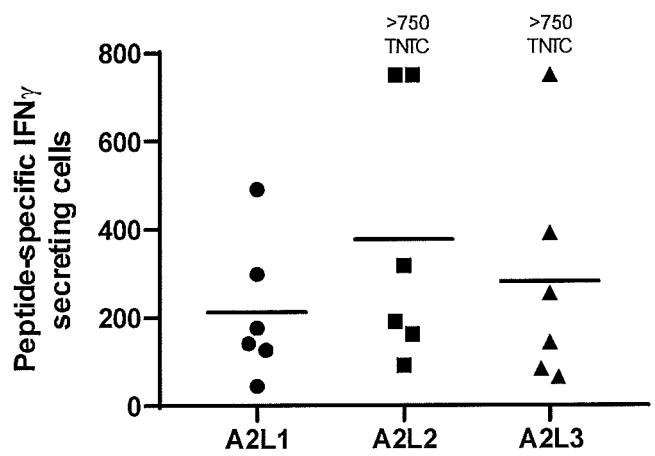
FIG. 15 shows the long ARG2 peptide A2L2 elicit strong and frequent CD4+ T-cell responses in healthy donors and cancer patients. (A) IFNy ELISPOT responses against the long peptides A2L1, A2L2 and A2L3 in PBMCs from six healthy donors. $4*10^5$ cells were plated pr. well and peptide and control stimulation were performed in triplicates. Specific spot counts (peptide-specific IFNy secreting cells) are given as the difference in number of IFNy spots between averages of the wells stimulated with peptide and control wells. Responses against peptide were too numerous to count (TNTC) in 3 settings and set to be >750 spots. (B) IFNy ELISPOT responses to A2L2 and ARG2-1 in PBMCs from 6 healthy donors. 4*10^5 cells were plate pr. well and peptide and control stimulation were performed in triplicates. Specific spot counts (peptide-specific IFNy secreting cells) are given as the difference in number of IFNy spots between averages of the wells stimulated with peptide and control wells. *p≤0.05 or **p≤0.01 according to the distribution free resampling rule. (C) IFNy ELISPOT responses against A2L2 peptide in PBMCs from healthy donors (n=30) and cancer patients with solid tumors (n=18). 3-4*10^5 cells were plated pr. well. Peptide and control stimulations were performed in triplicates. Each spot represents one donor and is the number of peptide-specific IFNy secreting cells (the difference between the average of wells stimulated with peptide and control wells). (D) Representative intracellular cytokine staining for IFNy and TFNa production in healthy donors (HD48 and HD53) and a cancer patient (AA27) with solid tumors stimulated with A2L2 or non-stimulated control. (E) IFNy ELISPOT responses to ARG2-1 and A2L2 in PBMCs from healthy donors (n=26) and cancer patients with solid tumors (n=11) for comparison of the magnitude of responses to the two peptides. 4*10^5 cells were plated pr. well and peptide and control stimulation were performed in triplicates. Specific spot counts (peptide-specific IFNy secreting cells) are given as the difference in number of IFNy spots between averages of the wells stimulated with peptide and control wells. ns: p=0.7038.
Figure 15:
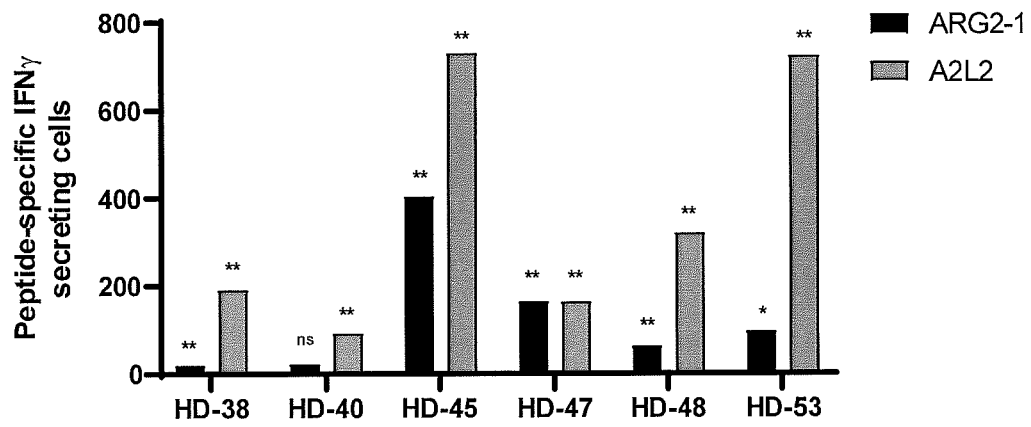
Figure 15:
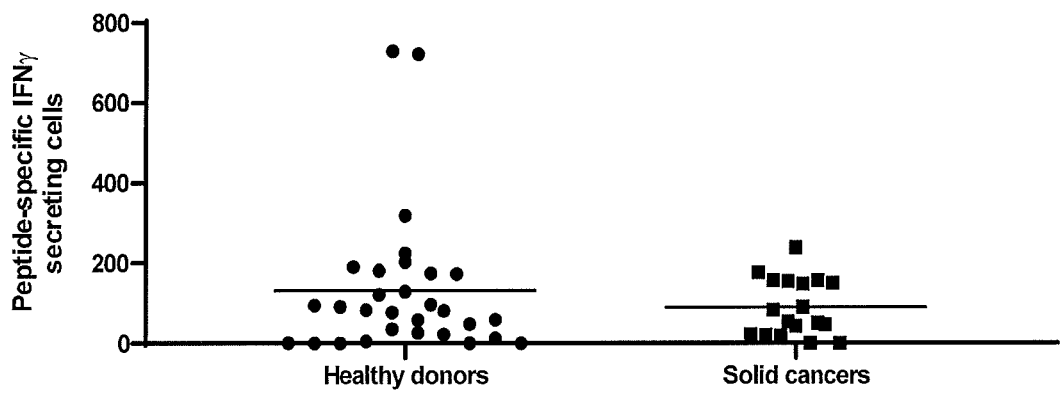
Figure 15:
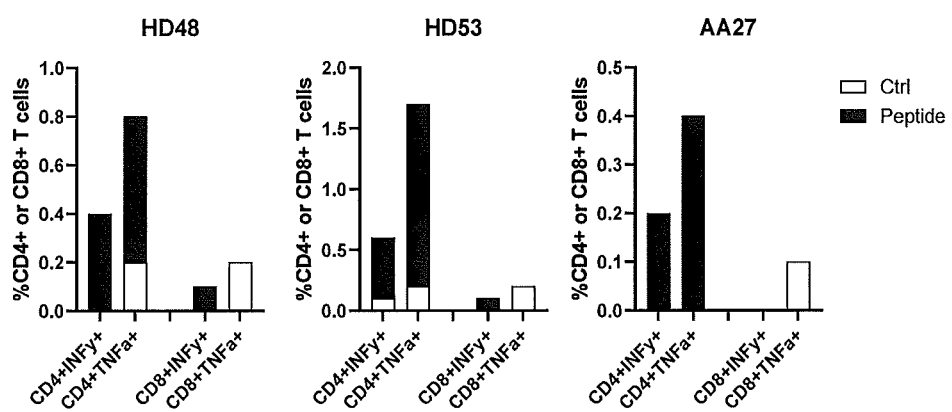
Figure 15:
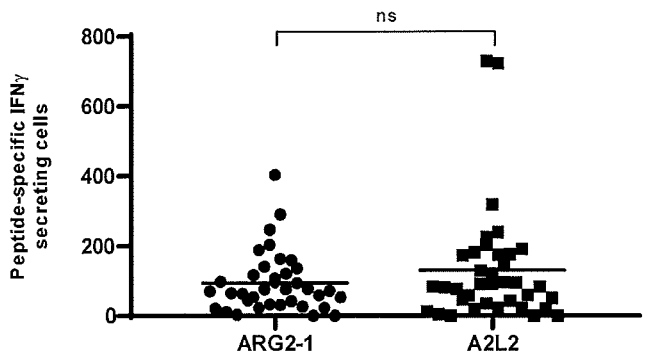

To test whether these long ARG2 peptides could be used to identify ARG2 responses, PBMCs from 6 healthy donors were stimulated once with each of the three long peptides. Subsequently, PBMCs were used to screen for immune responses in IFNy ELISPOT. As shown in FIG. 15A, immune responses against all three long peptides were identified, however, the 33-mer A2L2 gave the strongest and most frequent immune responses of the three long peptides in the examined donors. Since ARG2-1 is contained within A2L2, the longer peptide A2L2 was examined to determine if it more effectively stimulated ARG2-specific T cells. Thus, 6 healthy donors were stimulated with either ARG2-1 or A2L2 once and then setup in an IFNy ELISPOT assay. In 5 out of 6 donors, A2L2 immune responses were higher than ARG2-1 responses (FIG. 15B), although not significant (p=0.0625), suggesting that both peptides elicit frequent immune responses.

To characterize the immunogenicity of the A2L2, PBMCs from 30 healthy donors and 18 cancer patients (14 melanoma, 3 prostate cancer, 1 breast cancer patient) were screened by IFNy ELISPOT assay. Strong and frequent responses were observed in about 80% of both healthy donors and cancer patients (FIG. 15C). Intracellular cytokine staining for IFNy and TNFα production showed only CD4+ responses to A2L2 stimulation (FIG. 15D) similar to what was observed for ARG2-1. The immune responses towards A2L2 were on average higher compared to ARG2-1 responses in the same donor although not significant (p=0.7038) (FIG. 15E).

Characterization of ARG2-Specific T Cells

Figure 16:
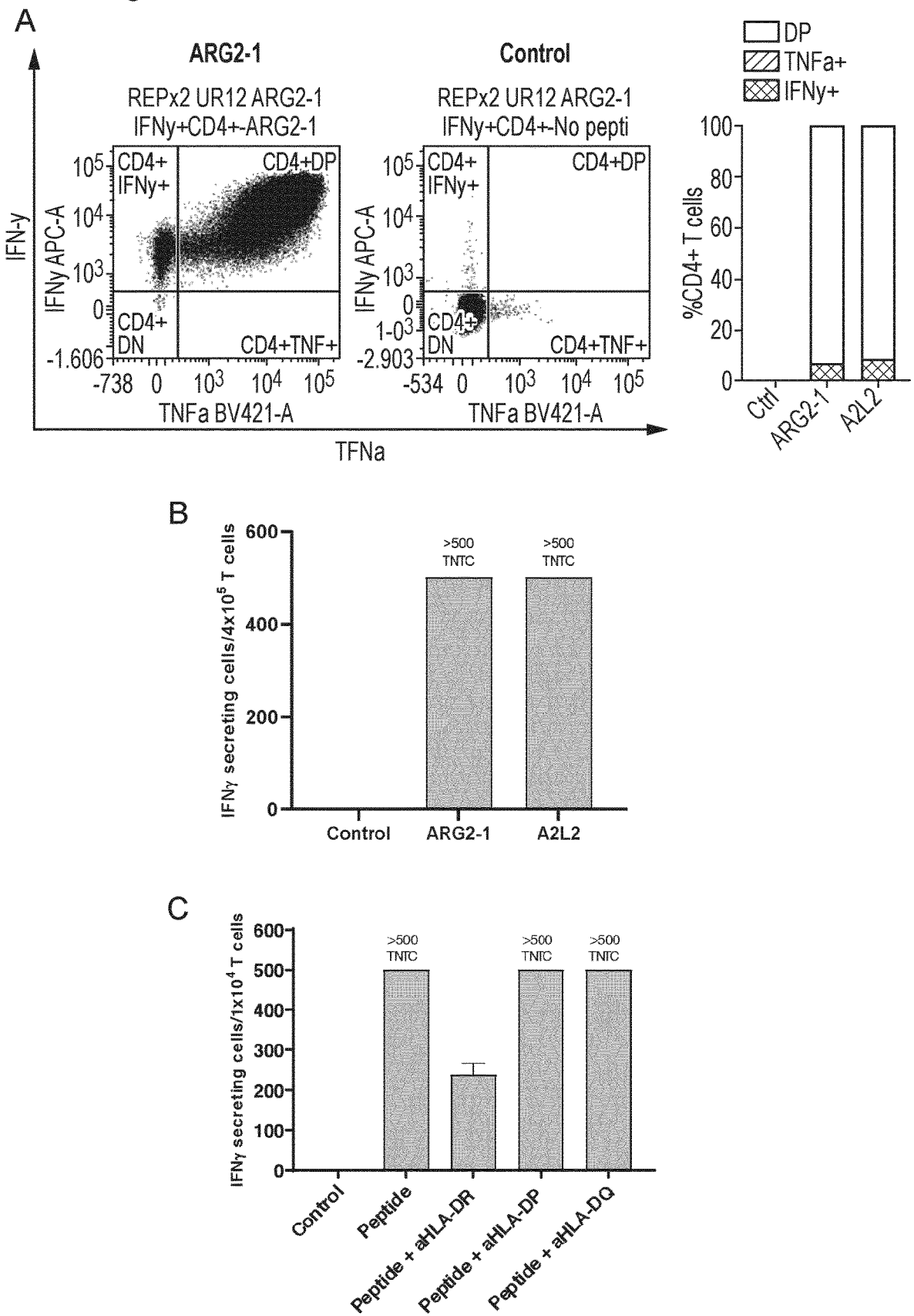
FIG. 16 shows that ARG2-specific T cells recognize ARG2-expressing dendritic cells. (A) ARG2-specific T cells were expanded from a patient with prostate cancer. The specificity of the T cell culture was assessed by intracellular cytokine staining for TNFa and IFNy production in peptide stimulated cells and a non-stimulated control. Left: Dot plot for ARG2-1 peptide stimulated and non-stimulated (control) cells. Right: % CD4+ T cells producing IFNy, TNFa or both in response to control stimulation (no peptide), ARG2-1 peptide stimulation or A2L2 peptide stimulation. (B) Specificity of the ARG2-specific T cells assessed by ELISPOT responses to control stimulation (no peptide), ARG2-1 peptide or A2L2 peptide. 4*10^4 cells were plated pr. well. TNTC=too numerous to count (more than 500 spots). (C) The HLA-restriction of ARG2-specific T-cells were examined. IFNy ELISPOT response of the ARG2-specific T cells toward ARG2-1 peptide in the presence of different class II blockers. (D) IFNy ELISPOT response by the ARG2-specific T cells to autologous dendritic cells transfected with irrelevant control mRNA (mock mRNA) or ARG2 mRNA. Effector to target ratio 5:1 with 5*10^4 effector cells plated pr. well. *p≤0.05 or **p≤0.01 according to the distribution free resampling rule.
Figure 16:
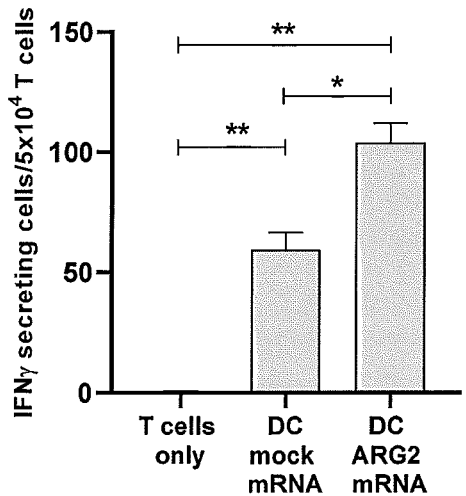

To further characterize the immune response towards ARG2, an ARG2-specific CD4+ T cell culture was generated. This was done by repeated stimulation of PBMCs isolated from a prostate cancer patient with ARG2 peptide loaded autologous DCs followed by enrichment and rapid expansion of specific cells. The T cell culture was highly specific to both ARG2- and A2L2 in intracellular cytokine staining for TNFα and IFNy (FIG. 16A) and IFNy ELISPOT (FIG. 16B). Furthermore, it was found that IFNγ production from the ARG2-specific T cell culture stimulated with peptide were inhibited by the addition of HLA-DR blockers, but not HLA-DP or HLA-DQ blockers in IFNy ELISPOT

| SEQ ID NO | Sequence | Name | Length |
|---|---|---|---|
| 62 | MSLRGSLSRLLQTRVHSILKKS------------------ | Signal sequence | 22 |
| 1 | MSLRGSLSRLLQTRVHSILK-------------------- | ARG2-0 | 20 |
| 2 | ----------LQTRVHSILKKSVHSVAVIG---------- | ARG2-1 | 20 |
| 3 | --------------------KSVHSVAVIGAPFSQGQKRK | ARG2-2 | 20 |
| | LONGER ARG2 SEQUENCES | | |
| 57 | -----SLSRLLQTRVHSILKKSVHSVAVIGAPFS------ | A2L3 | 29 |
| 58 | -SLRGSLSRLLQTRVHSILKKSVHSVAVIGA--------- | A2L1 | 30 |
| 59 | -SLRGSLSRLLQTRVHSILKKSVHSVAVIGAPFS------ | A2L2 | 33 |

(FIG. 16C). To assess the specificity of the ARG2-specific T cell culture the ability of the ARG2-specific T cell culture to recognize and react against cells with intracellular expression of ARG2 was examined. To this end, autologous DCs were transfected with mRNA encoding ARG2 fused to the DC-LAMP signal sequence, which targets a protein toward the lysosomal compartment and thus directs the protein toward class II presentation. Higher reactivity against ARG2 mRNA transfected DCs compared to mock transfected DCs was observed (FIG. 16D). FACS analysis of transfected cells showed >90% transfection efficiency and mRNA analysis of mock and mRNA transfected DC showed a large increase in ARG2 expression 24 hrs after transfection (data not shown).

Figure 17:
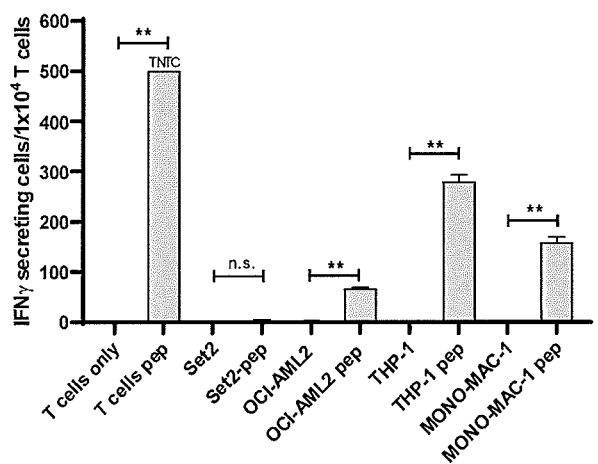
FIG. 17 shows that ARG2-specific T cells recognize ARG2-expressing malignant myeloid cells. (A) To identify HLA-matched malignant cells the ARG2-specific T cells were examined in IFNy ELISPOT response toward different relevant cancer cell lines pre-pulsed with ARG2-1 peptide. The same cancer cell lines without peptide stimulation were examined as control. Effector to target ratio 1:1 with 1*10^4 effector cells plated pr. well. *p≤0.05 or **p≤0.01 according to the distribution free resampling rule. TNTC=too numerous to count (>500). (B) IFNy ELISPOT response of the ARG2-specific T cells toward THP-1 cells pulsed with ARG2-1 peptide and class II blockers. (C) ARG2 expression in THP-1 evaluated by RT-qPCR following 48 hr incubation of THP-1 cells with different cytokines. Data are represented as fold change vs unstimulated THP-1 cells, mean+SD, n=4. (D) IFNy ELISPOT response of the ARG2-specific T cells toward THP-1 cells stimulated with the cytokine cocktail. Effector to target ratio 5:1 with 1.5*10^5 effector cells plated pr. well. **p≤0.01 and ns=not significant according to the distribution free resampling rule. (E) Intracellular staining of TNFa and IFNy production from CD4+ T cells in the ARG2-specific T cell culture when incubated with unstimulated THP-1 cells or THP-1 cells pre-stimulated with cytokine cocktail for 48 hrs. Effector to target ratio 2:1 with 500,000 effector cells used pr. condition. (F) ARG1 and ARG2 expression in THP-1 cells evaluated by RT-qPCR following 48 hrs incubation with cytokine cocktail. Unstimulated THP-1 cells served as control. Data are represented as relative expression to the housekeeping gene ACTB, mean+SD, n=4. (G) IFNy ELISPOT response of the ARG2-specific T cells toward THP-1 cells stimulated with the cytokine cocktail (THP-1+cyto) and the class II blocker, aHLA-DR. Effector to target ratio 5:1 with 1.5*10^5 effector cells plated pr. well. **p≤0.01 and ns=not significant according to the distribution free resampling rule. (H) ARG2 expression in THP-1 cells evaluated by RT-qPCR following 48 hrs of stimulation with cytokine cocktail or IFNy. Unstimulated THP-1 cells are included as control. Data are represented as relative expression to the housekeeping gene RPLPO, mean+SD, n=4. (I) IFNy ELISPOT response of the ARG2-specific T cells toward THP-1 cells pre-stimulated with the cytokine cocktail (THP-1+cytokines) or IFNy (THP-1+IFNy). Effector to target ratio 2.5:1 with 5*10^4 effector cells plated pr. well. **p≤0.01 and ns=not significant according to the distribution free resampling rule.
Figure 17:
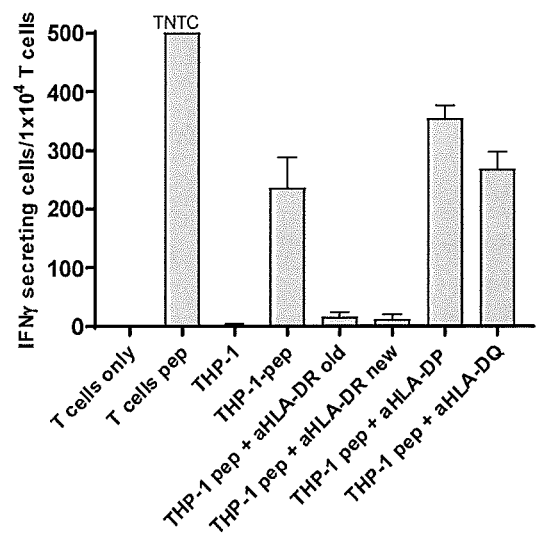
Figure 17:
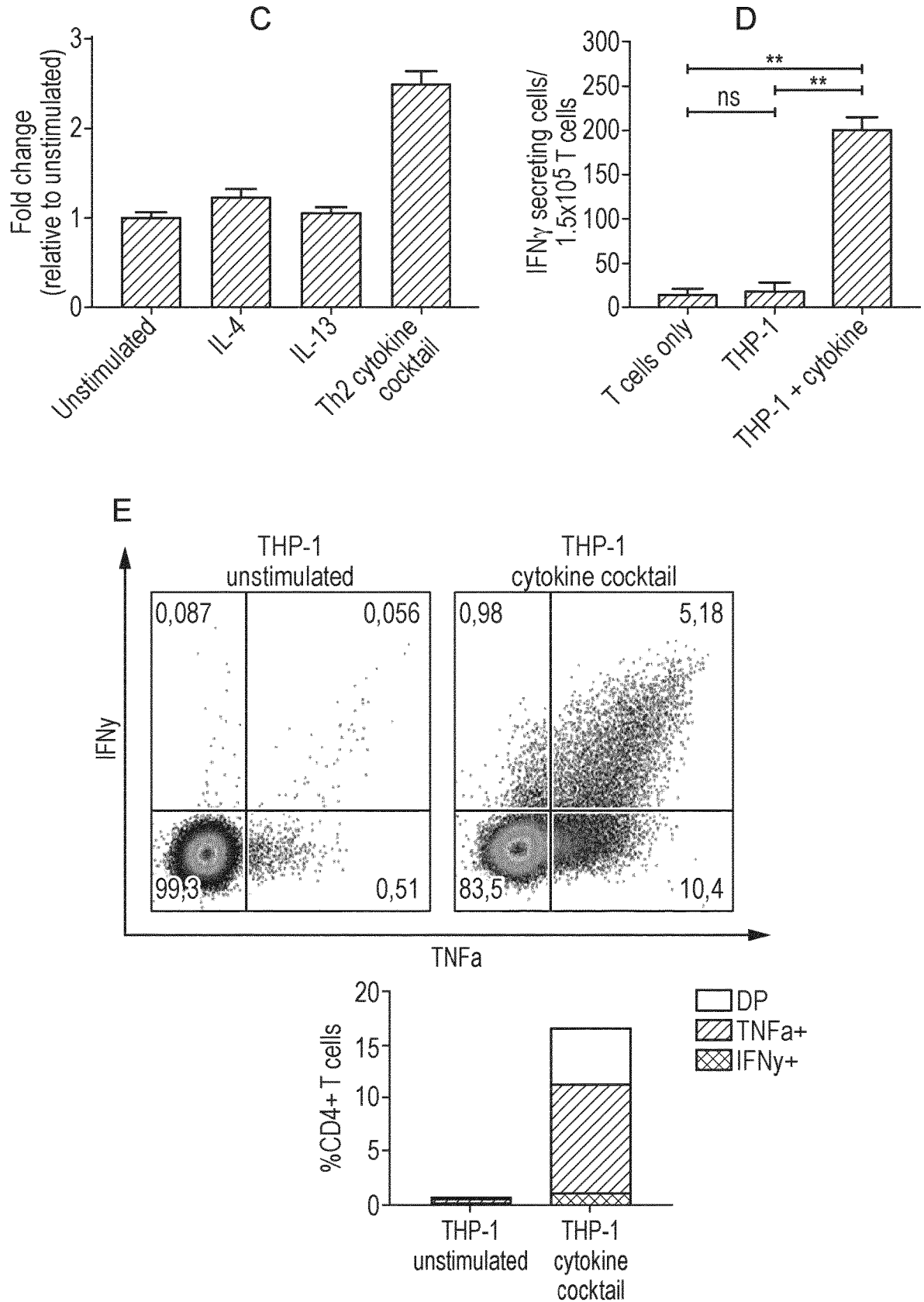
Figure 17:
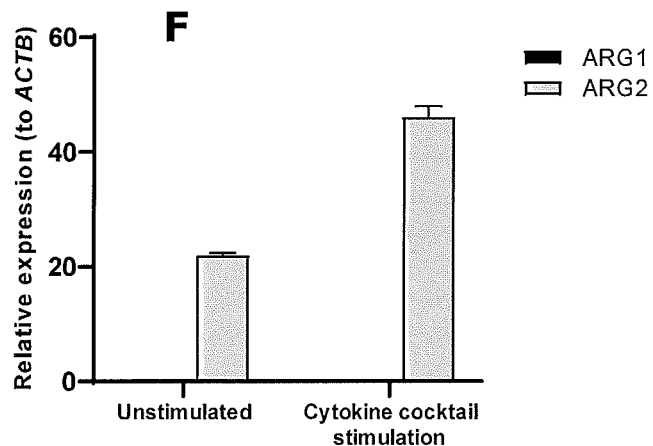
Figure 17:
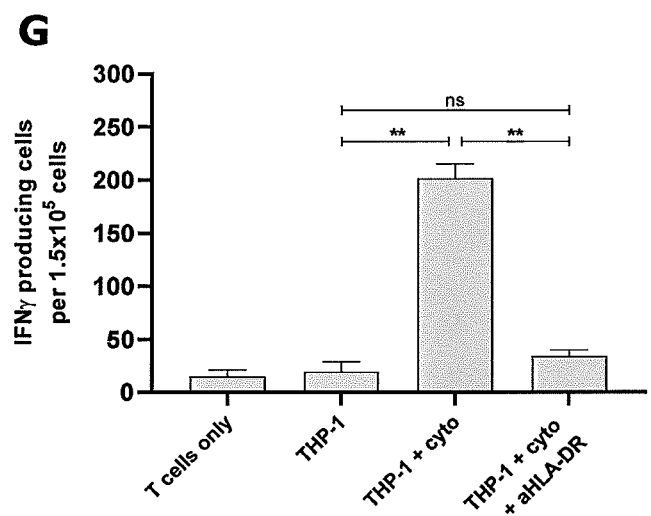
Figure 17:
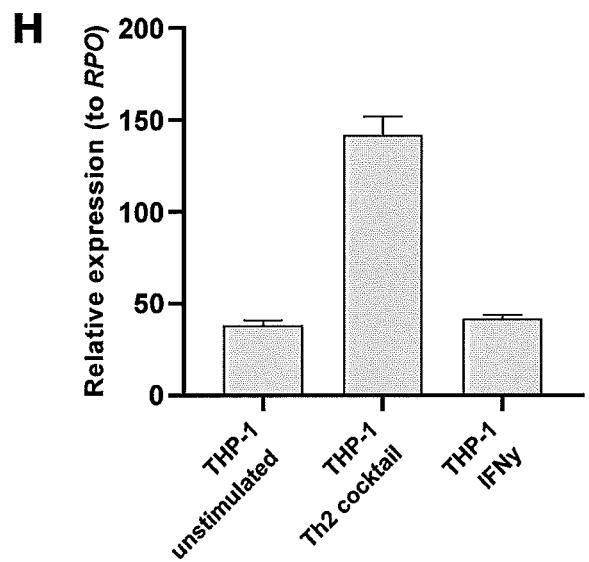
Figure 17:
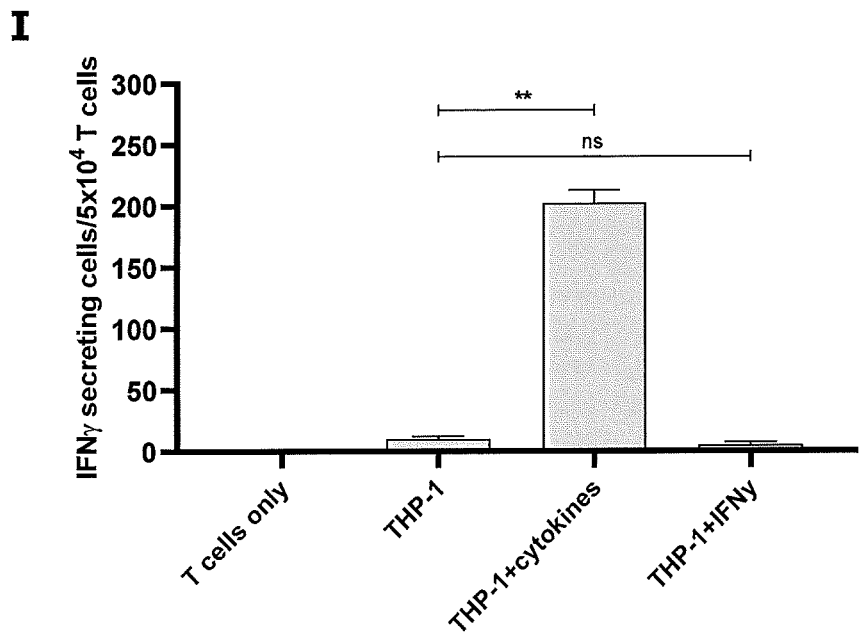

Having shown reactivity toward ARG2-producing immune cells the ability of the ARG2-specific T cell culture to recognize and react against different cancer cells was investigated using IFNy ELISPOT assays. HLA sequencing analysis of the donor for the specific T cell culture allowed us to choose three HLA-matched (HLA-DR01:01) AML cell lines with low endogenous ARG2 expression (OCI-AML2, THP-1 and MONO-MAC-1,—data not shown) and pulse with ARG2-1 peptide to subsequently use as target cells for IFNy ELISPOT. Set2, another AML cell line with high endogenous ARG2 expression but HLA-mismatch with the ARG2-specific T cell culture, was included as a negative control. OCI-AML2, THP-1 and MONO-MAC-1 were effectively recognized by the ARG2-specific T cells (FIG. 17A) whereas Set2 was not. The HLA-DR restriction of the ARG2-specific T cells was confirmed by the addition of two different HLA-DR specific antibodies, since addition of both HLA-DR blockers abrogated the recognition of ARG2-1 pulsed THP-1 cells (FIG. 17B).

The THP-1 cell line is a monocytic cell line derived from a peripheral blood of a patient with AML. THP-1 cells are reported to have maintained some plasticity with their function depending on the presence of specific cytokines in their surroundings. IL-4 and IL-13 are reported to be the main inducers of ARG1, but their function on ARG2 is not well known. Moreover, THP-1 cells are reported to acquire DC-like characteristics upon 48 hr stimulation with a cytokine cocktail of IL-4, GM-CSF and TFNα (referred to herein as "the cytokine cocktail"). It was therefore examined if stimulation of THP-1 cells with IL-4, IL-13 or the cytokine cocktail would increase ARG2 expression in THP-1 cells. A more than 2-fold induction of ARG2 expression was found upon stimulation with the cytokine cocktail, whereas IL-4 and IL-13 did not have much effect on ARG2 expression levels (FIG. 17C). Next it was investigated if the increase in ARG2 expression after cytokine cocktail stimulation could elicit an immune response from ARG2-specific T cells. Indeed, it was found that the cytokine cocktail led to recognition of the stimulated THP-1 cells in IFNy ELISPOT (FIG. 17D) and production of TNFα and IFNγ detected by intracellular cytokine staining (FIG. 17E). Only ARG2 expression increased after treatment of the THP-1 cells with the cytokines whereas ARG1 expression remained unchanged (FIG. 17F). The response toward cytokine stimulated THP-1 cells could be blocked by HLA-DR specific antibodies (FIG. 17G).

Of note, the cytokine cocktail stimulated THP-1 cells changed morphology compared to unstimulated cells with more colony-formation, small protrusions and an acquired adherence (data not shown). Importantly, the cytokine cocktail did not upregulate HLA-DR expression (data not shown). In contrast, treatment of THP-1 cells with IFNy increase HLA-DR expression on the cell surface (not shown), but not ARG2 expression (FIG. 17H) and IFNy stimulated THP-1 cells were not recognized by ARG2-specific T cells in IFNy ELISPOT assay (FIG. 17I).

Figure 18:
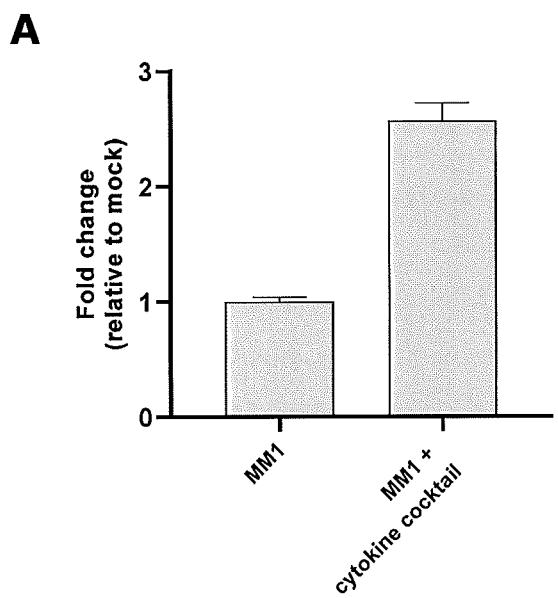
FIG. 18 shows that ARG2-specific T cells recognize several ARG2-expressing malignant myeloid cells. (A) ARG2 expression in MONO-MAC-1 (MM1) cells evaluated by RT-qPCR following 48 hrs incubation with cytokine cocktail. Data are represented as fold change vs unstimulated MM1 cells, mean+SD, n=4. (B) ARG2 expression in MM1 cells evaluated by RT-qPCR following 48 hrs incubation with cytokine cocktail or IFNy. Data are represented as fold change vs unstimulated MM1 cells, mean+SD, n=4. (C) IFNy ELISPOT response of the ARG2-specific T cells toward MM1 cells pre-stimulated with the cytokine cocktail (MM1+cytokine cocktail) or IFNy (MM1+IFNy). Effector to target ratio 2.5:1 with 5*10^4 effector cells plated pr. well. **p≤0.01 and ns=not significant according to the distribution free resampling rule.
Figure 18:
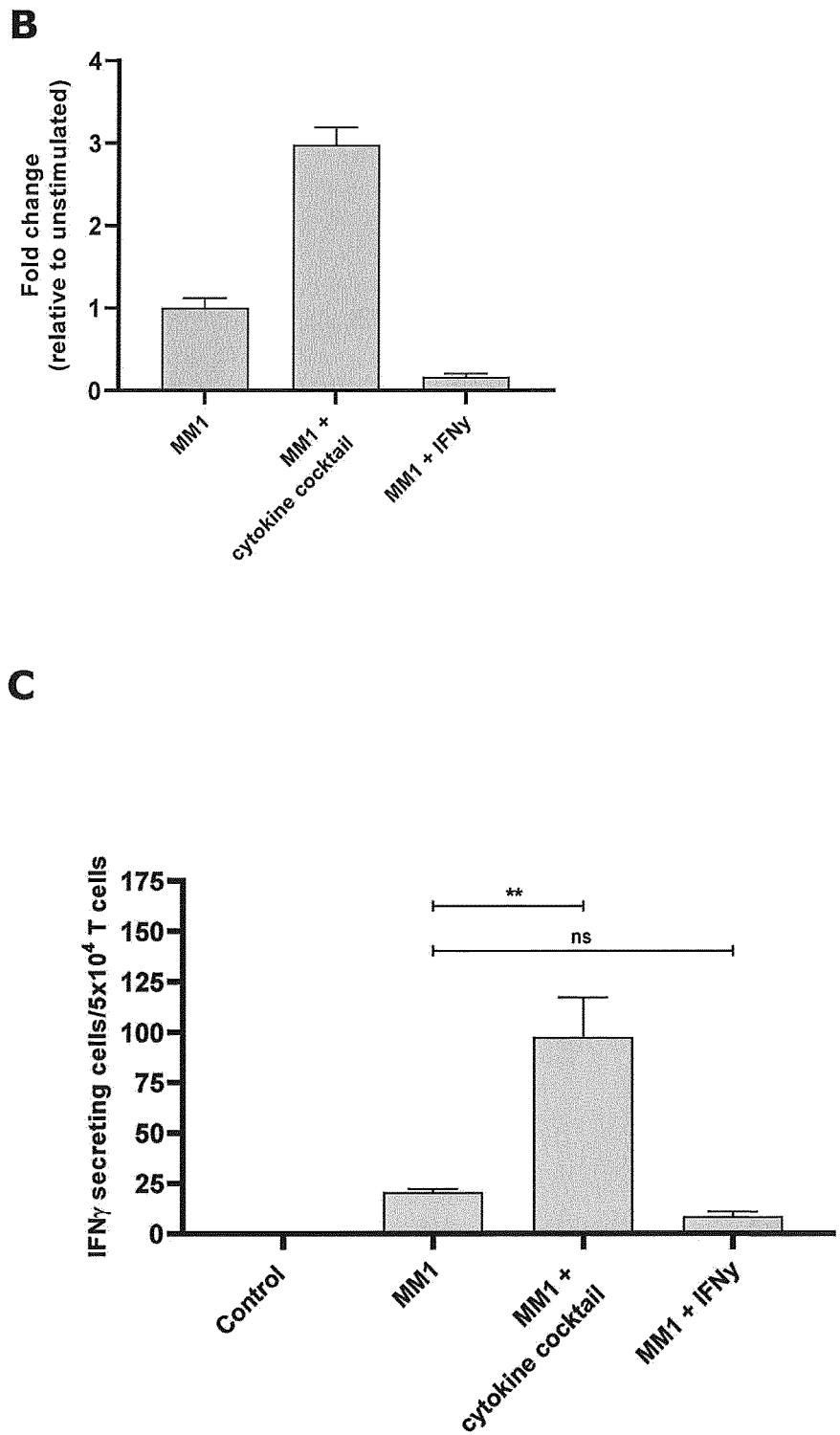

MONO-MAC-1 is an AML cell line that like THP-1 cells have maintained the ability to differentiate or be affected by cytokine stimulations. Similar to the observation for THP-1 cells, it was possible to increase ARG2 expression in MONO-MAC-1 cells by cytokines (FIG. 18A). Stimulation of MONO-MAC-1 cells with the cytokine cocktail did not increase HLA-DR expression compared to unstimulated cells in MONO-MAC-1 cells (not shown). Furthermore, MONO-MAC-1 cells stimulated with IFNy did not upregulate ARG2 expression (FIG. 18B) and only cytokine treated MONO-MAC-1 cells were recognized by the ARG2-specific T cells in IFNy ELISPOT (FIG. 18C). MONO-MAC-1 stimulated with the cytokine cocktail also change morphology similar to what was observed for THP-1 cells (not shown)

Figure 7:
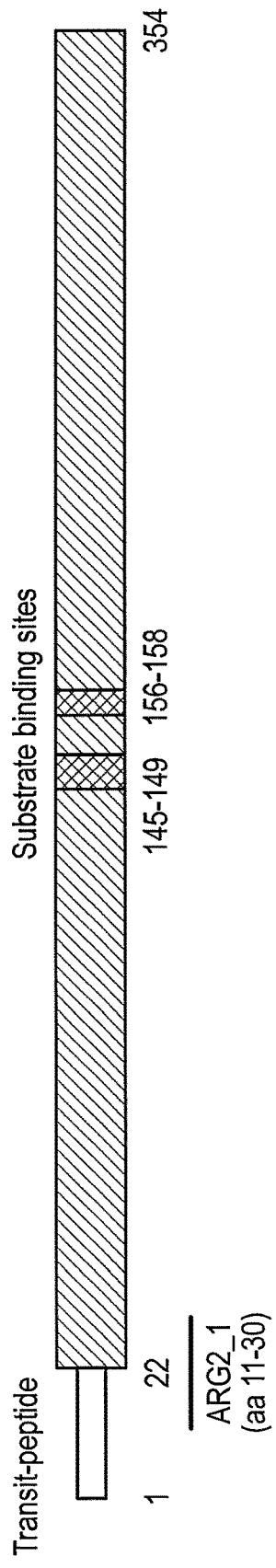
FIG. 7 shows a schematic representation of Arginase2 illustrating the position of the ARG2_1 fragment.
Figure 19:
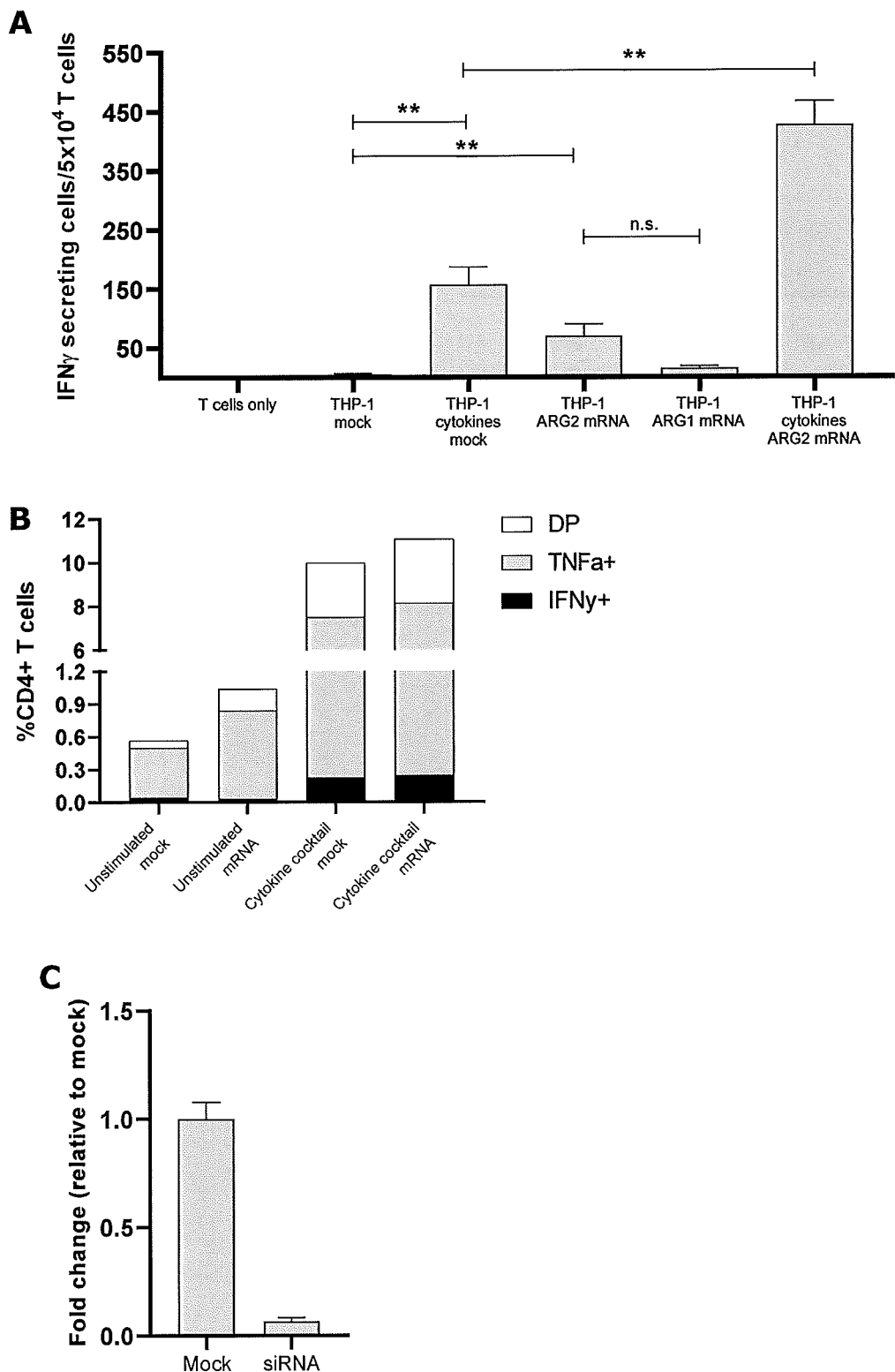
FIG. 19 shows that the recognition of ARG2-expressing cells by ARG2-specific T cells depend on the level of ARG2 expression in addition to the antigen processing apparatus of the target cells. (A) IFNy ELISPOT response of the ARG2-specific T cells toward THP-1 cells unstimulated or pre-stimulated with the cytokine cocktail and mock transfected or transfected with ARG1 or ARG2 mRNA. Effector to target ratio 2.5:1 with 5*10^4 effector cells plated pr. well. **p≤0.01 and ns=not significant according to the distribution free resampling rule. (B) Intracellular staining of TNFa and IFNy production from CD4+ T cells in the ARG2-specific T cell culture when incubated with unstimulated THP-1 cells or THP-1 cells pre-stimulated with cytokine cocktail followed by either mock (mock) or ARG2 mRNA (mRNA) transfection. Effector to target ratio 2:1 with 500.000 effector cells used pr. condition. (C) ARG2 expression in THP-1 cells evaluated by RT-qPCR 48 hrs post transfection with ARG2-specific siRNAs. Data are represented as fold change vs mock transfected THP-1 cells, mean+SD, n=4. (D) Intracellular staining of TNFa and IFNy production from CD4+ T cells in the ARG2-specific T cell culture when incubated with mock or siRNA transfected cells kept under unstimulated or cytokine cocktail stimulated conditions for 48 hrs prior to setup. Effector to target ratio 2:1 with 500.000 effector cells used pr. condition. (E) ARG2 expression in THP-1 cells evaluated by RT-qPCR 48 hrs post transfection with ARG2-specific siRNAs followed by cytokine cocktail stimulation. Data are represented as fold change vs unstimulated mock transfected THP-1 cells, mean+SD, n=4.
Figure 19:
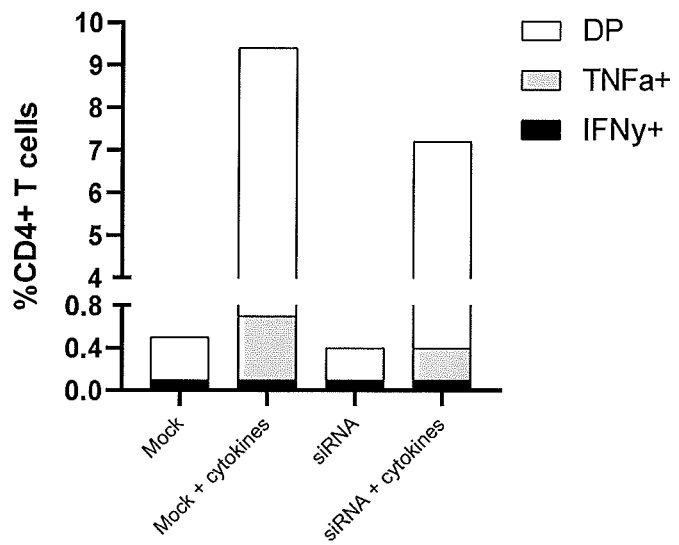
Figure 19:
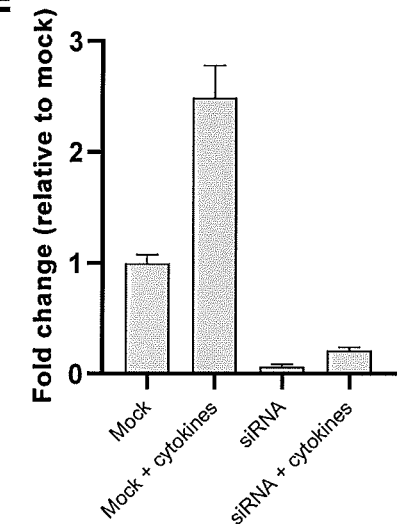

To further test the notion of ARG2 expression dependent T-cell recognition, THP-1 cells were transfected with ARG2 mRNA using the ARG2-DC-LAMP construct. The DC-LAMP sequence is reported to be specific for mature DCs, but THP-1 cells can be differentiated into DC-like cells and the construct is thus applicable for transfection of THP-1 cells as well. Indeed, it was observed that the ARG2-specific T-cell culture react towards THP-1 cells transfected with ARG2-DC-LAMP mRNA (FIG. 19A). The reactivity was in addition significantly higher toward cells transfected with ARG2-DC-LAMP mRNA compared to cells transfected with ARG1-DC-LAMP mRNA (FIG. 7A), emphasizing the specificity of the ARG2-specific T cells. Furthermore, 48 hrs of stimulation with cytokines prior to transfection increased the immune response compared to cells that were only mRNA transfected or cytokine stimulated (FIG. 19A). Intracellular cytokine staining for TNFα and IFNγ production showed a similar trend (FIG. 19B). Electroporation efficiency was assessed 24 hrs post transfection by FACS analysis of GFP-expressing cells and showed efficient transfection (>99% GFP+ cells) (data not shown). In line with this, a large fold increase in ARG2 and ARG1 expression compared to mock cells was observed 24 hrs post transfection with ARG2-DC-LAMP mRNA or ARG1-DC-LAMP mRNA, respectively (data not shown). ARG2 expression levels in mRNA transfected THP-1 cells were high compared to endogenous ARG2 expression levels in Set2 cells (data not shown).

Next, we used siRNA mediated knock down of ARG2 to further prove that T cell recognition and activation were dependent on ARG2 expression. Transfection of THP-1 cells with a pool of three ARG2 specific siRNAs led to efficient ARG2 KD (FIG. 19C). TNFα and IFNy production was inspected by intracellular cytokine staining 48 hrs after transfection with siRNAs and cytokine stimulation. We observed a decrease in both TNFα and IFNy production from ARG2-specific T cells toward siRNA+cytokine cells compared to mock+cytokine cells, even if we did not manage to abrogate the production completely (FIG. 19D). RT-qPCR of ARG2 expression in the cells also showed ARG2 KD in siRNA+cytokine cells, however ARG2 expression levels are slightly higher than the levels obtained with only siRNA KD (FIG. 19E).

EXAMPLE 3—PROOF OF VACCINE PRINCIPLE IN MURINE MODEL

In order to demonstrate the therapeutic potential of vaccination against Arginase2, mouse models were developed. Murine Arginase2 has 85% sequence homology to human Arginase2, so it is not possible simply to use the human sequences. Epitope prediction servers were used to search for likely epitopes in murine Arginase2 for C57 mice (H-2Kb, H2-Db).

Epitopes predicted for binding to H2-Kb and H2-Db were found in two clusters; around aa85 and aa182. These are shown below, in alignments to illustrate the overlap.

| SEQ ID | SEQUENCE | NAME | START POS | END POS |
|---|---|---|---|---|
| 45 | VVYPRSVGL--------- | mArg2 P1 | 85 | 93 |
| 46 | VVYPRSVGLANQELAEVV | mArg2 P2 | 85 | 102 |
| 47 | --------PNIVYIGL | mArg2 P3 | 191 | 198 |
| 48 | WIKPCLSPPNIVYIGL | mArg2 P4 | 182 | 197 |
| 49 | -----LSPPNIVYI-- | mArg2 P5 | 188 | 196 |
| 50 | IQYFSMREI | mArg2 P6 | 213 | 221 |

Each predicted epitope is predicted to bind either H2-Kb or H2-Db, but mArg2_P2 is put together by two predicted epitopes and would—theoretically—be able to bind to both H2-Kb and H2-Db. mArg2_P6 was predicted to bind to both H2-Kb and H2-Db.

Figure 11:
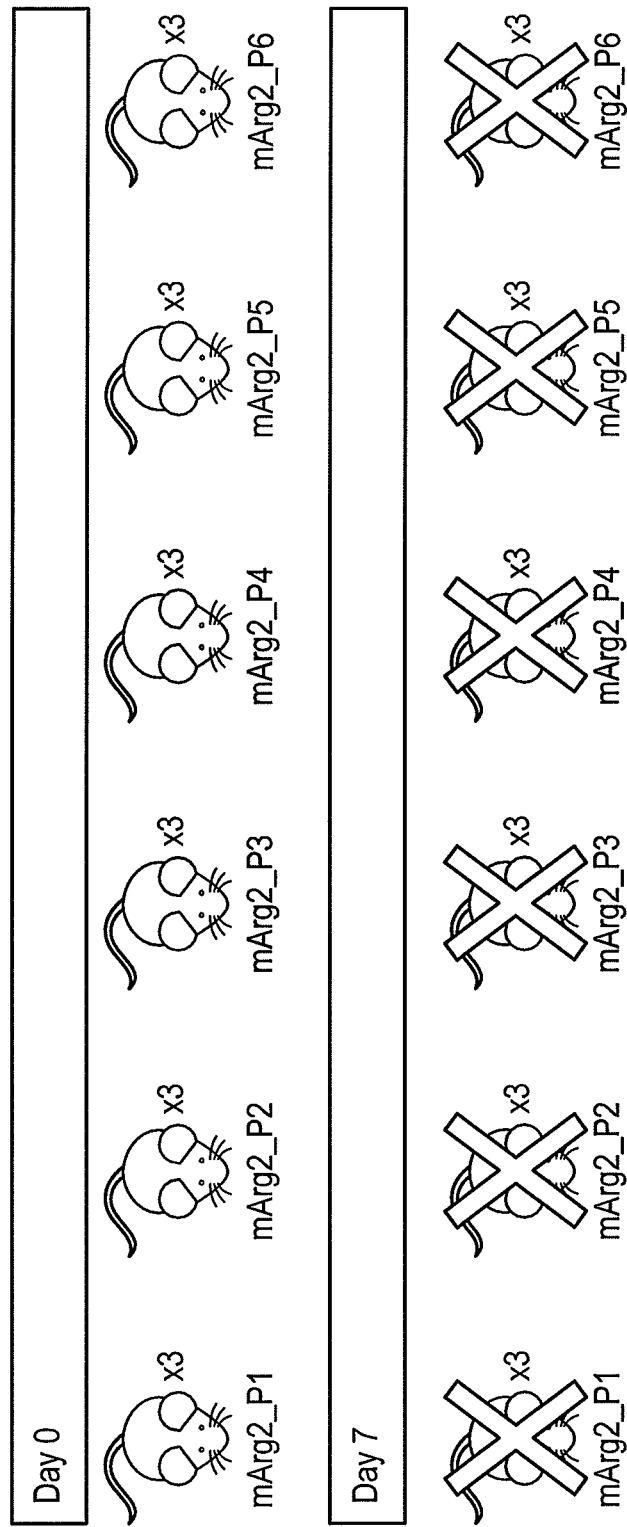
FIG. 11 shows the experimental scheme for in vivo murine Arg2 testing. 3 mice in each group are vaccinated s.c. with one of the six peptides. 7 days after, the mice are terminated, spleens are homogenised and PBMC are used for mIFNy ELISPOT.

These peptides are used for a vaccination screen (see experimental schematic in FIG. 11), where three C57 mice are vaccinated subcutaneously with one of the 6 peptides. One week later, the mice are sacrificed and the spleens homogenized to obtain PBMC. These are used to set up IFNy ELISPOT to screen for responses against both the peptide used for vaccination and the other predicted epitope peptides with overlapping sequences.

Figure 12:
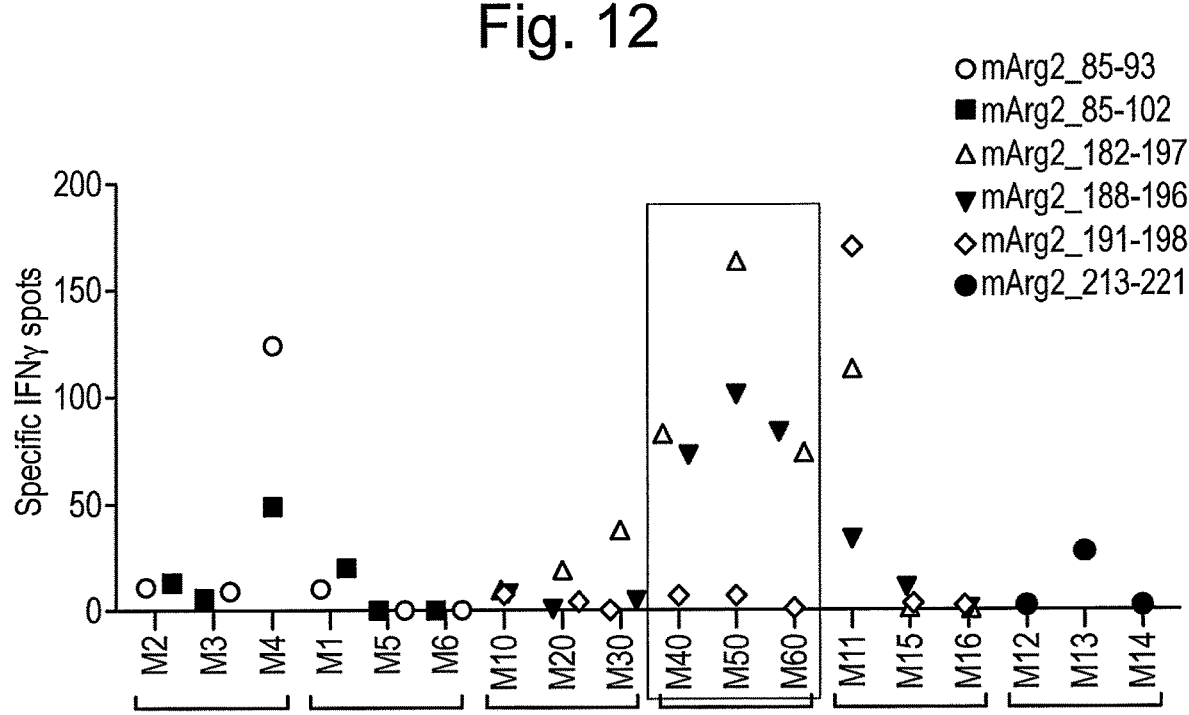
FIG. 12 shows results of the mIFNy ELISPOT performed following the experiment of FIG. 11. Spot counts are given as a difference between averages of the wells stimulated with peptide with the controls without peptide. $8*10^5$ cells were plated pr. well with or without peptide was performed in triplicates. Brackets indicate mice that were vaccinated with the same peptide, and a box highlights the mice with the strongest and most prominent response.
Figure 13:
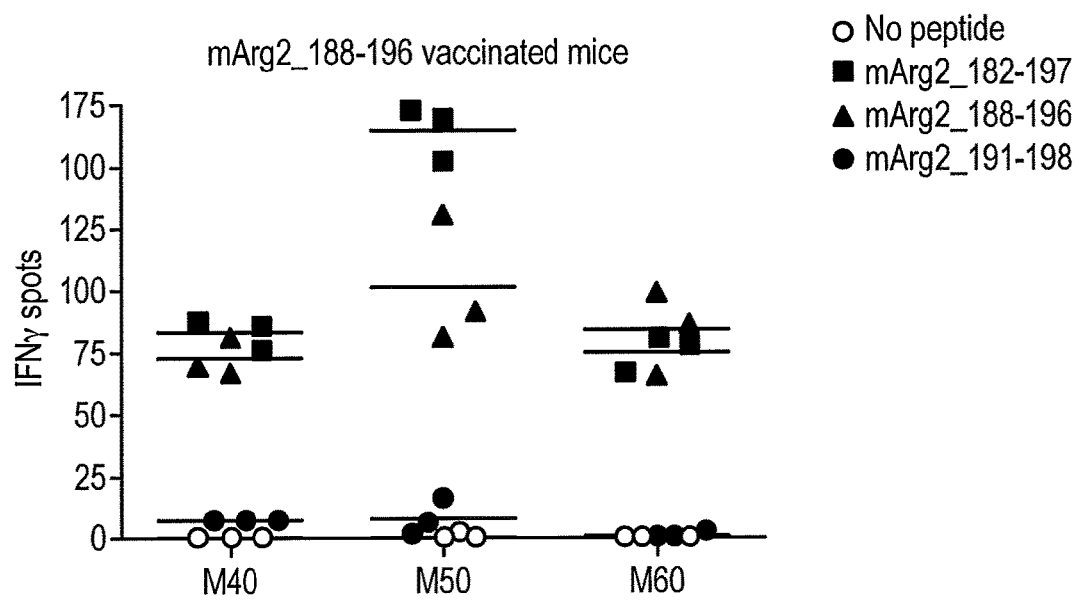
FIG. 13 shows that vaccination with mARG2_188-196 gives strong mIFNy responses against both mArg2_188-196 and mArg2_182-197. $8*10^5$ cells were plated pr. well and peptide and control stimulations was performed in triplicates.

As shown in FIG. 12, mice vaccinated with mArg2 P5 (aa188-196) gave the strongest and most prominent responses. Further vaccination experiments with this peptide were conducted. As shown in FIG. 13, responses in mice vaccinated with mArg2 P5 were observed to both mArg2 P5 (aa188-196) and P4 (aa182-197), whereas no response or only weak responses were observed to mArg2 P3 (as191-198). This suggests that the main epitope is located within aa188-196. However, overall, the experiment demonstrates that vaccination with Arginase2 peptides is able to stimulate immune responses in vivo, validating the therapeutic potential for Arginase2 vaccination as a general principle.

EXAMPLE 4—FURTHER PROOF OF VACCINE PRINCIPLE IN MURINE MODEL-LEWIS LUNG CARCINOMA

Materials and Methods

Peptide Design—see Example 3.
Cell Culture

Tumor derived cell line Lewis Lung (LL2) were cultured in DMEM supplemented with penicillin, streptomycin and 10% FBS. Cells were passaged 2-3 times a week by detachment from the flask with 0.25% Trypsin-EDTA (Gibco).
Animal Experiments Animal experiments were performed at the animal facility of the Department of Oncology, Herlev Hospital. All experiments with mice were reviewed and approved by the Danish Animal Experimentation Council. Daily care and breeding of C57BL/6 mice was performed by animal caretakers of the animal facility. For the therapeutic vaccination studies, C57BL/6 mice were purchased from Taconic.
Tumor Injections LL2 cells (5*10^5) were resuspended in 100 ul of serum free medium and were injected subcutaneously in the right flank of female C57BL/6 mice. Tumor volumes were measured by digital caliper and the endpoint of tumor study was a tumor reaching the threshold size of 800 mm$^3$ or due to the formation of ulcers on the tumor.

Peptide Vaccination and Murine ELISPOT

Murine Arg2 peptides (P1-P6) were synthesized by PepScan or Schäfer and dissolved in either ultrapure water or DMSO at 2 mM or 10 mM, respectively, depending on the reported solubility.

Dissolved peptides were subsequently emulsified with Montanide™ adjuvant (50ul/mouse) (Seppic Inc.) for an optimal dose of 100 ug total peptide given in a total volume of 100 ul. The emulsified peptide vaccination was injected subcutaneously at the base or the tail or the flank of 12-16 week old C57BL/6 mice with a 27G needle. Control mice were given water and Montanide™ emulsification in a total volume of 100 ul. For therapeutic vaccine studies on tumor inoculated mice, vaccinations were given at day 0 and 7 after tumor inoculation at the flank of the tail and the left flank, respectively. For epitope screening- and validation experiments, a single dose of vaccine was given to mice at the right flank. One week later, mice were sacrificed, and spleens were recovered. Spleens were smashed through a 70 μM filter and red blood cells were lysed using Red Blood Cell Lysis Buffer (Qiagen). Cells were washed 4 times and counted before setup for murine IFNy ELISPOT assay with 8*10$^6$ cells pr. well.
Treatment with PD-1 Blocking Antibody Anti-mouse PD-1 (CD279) monoclonal antibody was purchased from BioXCell (clone: RMP1-14). For efficacy studies, mice received 250 μg PD-1 blocking antibody in 200 μl PBS injected intraperitoneally. Mice were treated with anti-PD-1 three times pr. week starting on day 4 after LL2 inoculation.
Statistical Analysis ELISPOT responses were analyzed using distribution free resampling (DFR) method, described by Moodie et al (ref). Statistical analysis of ELISPOT responses was performed using R studio. The difference in responses (specific IFNy-secreting cells) toward ARG2-1 and A2L2 were compared with the use of Wilcoxon matched pairs signed ranked t test (using Prism 8) with a significance level of 0.05. Statistical analysis of difference in average tumor growth between control and Arg2 vaccinated groups was performed by mixed effect analysis using Prism 8.

Results

Figure 20:
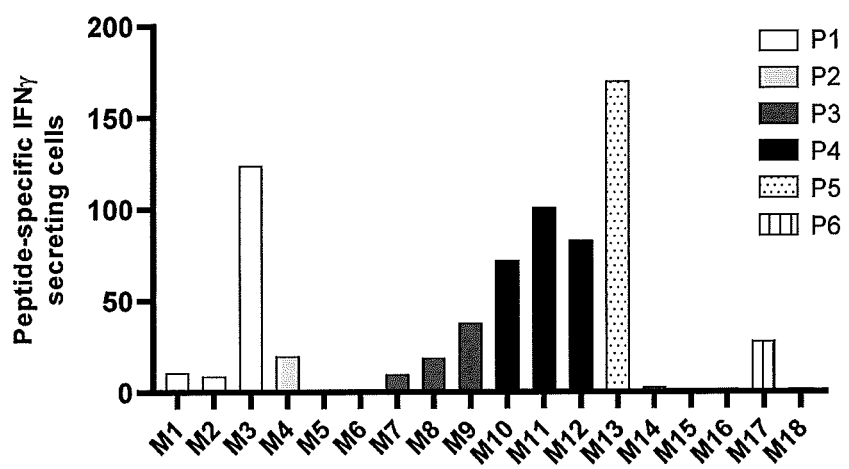
FIG. 20(A) Murine IFNy ELISPOT screening of splenic cells from C57BL/6 mice vaccinated with one of six different predicted Arg2 epitopes. 8*10^5 cells were plated pr. well and peptide and control stimulation were performed in triplicates. Specific spot counts (peptide-specific IFNy secreting cells) are given as the difference in number of IFNy spots between averages of the wells stimulated with peptide and control wells. (B) Murine IFNy ELISPOT of splenic cells from C57BL/6 mice vaccinated with Arg2 peptide P4 (M1-M5) or a control vaccination (Ctr11-4). 8*10A5 cells were plated pr. well and peptide and control stimulation were performed in triplicates. Specific spot counts (peptide-specific IFNy secreting cells) are given as the difference in number of IFNy spots between averages of the wells stimulated with peptide and control wells. (C) Arg2 expression in engrafted tumors of different origin in C57BL/6 background. 3 engrafted tumors were evaluated pr. tumor type. Data are represented as relative expression to the housekeeping gene Hprt 1, mean+SD, n=3. (D) Treatment schedule for two individual efficacy studies with Arg2 vaccination in LL2 inoculated mice with or without addition of anti-PD-1 treatment. 5*10^5 LL2 cells were subcutaneously injected in the right flank at day 0 followed by treatment with (E) control or Arg2 vaccinations with Arg2 peptide (n=20 for both groups) or (F) control vaccination, Arg2 vaccination, anti-PD-1 treatment, or Arg2 vaccination+anti-PD-1 treatment (n=10 for all groups). (E-F) Average tumor growth of LL2 tumors in the individual efficacy studies. Error bars indicate the standard error of the mean (SEM), ****=p≤0.0001. (G) Individual tumor sizes from the treatment groups described in (E). Error bars indicate the standard deviation (SD).
Figure 20:
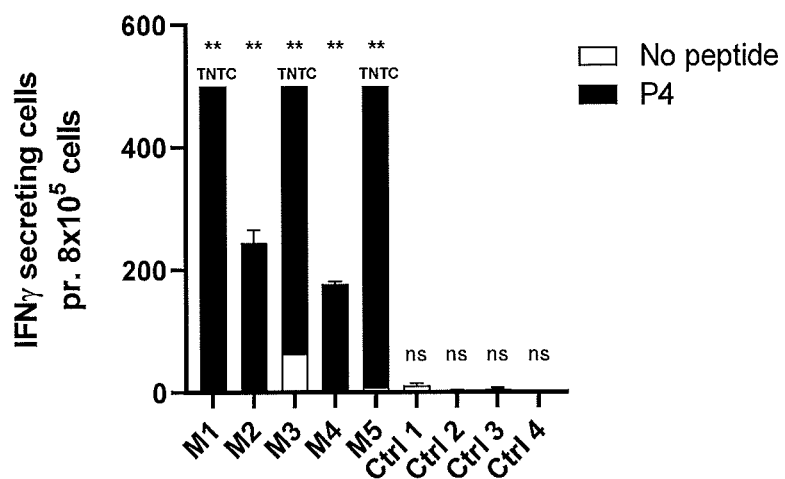
Figure 20:
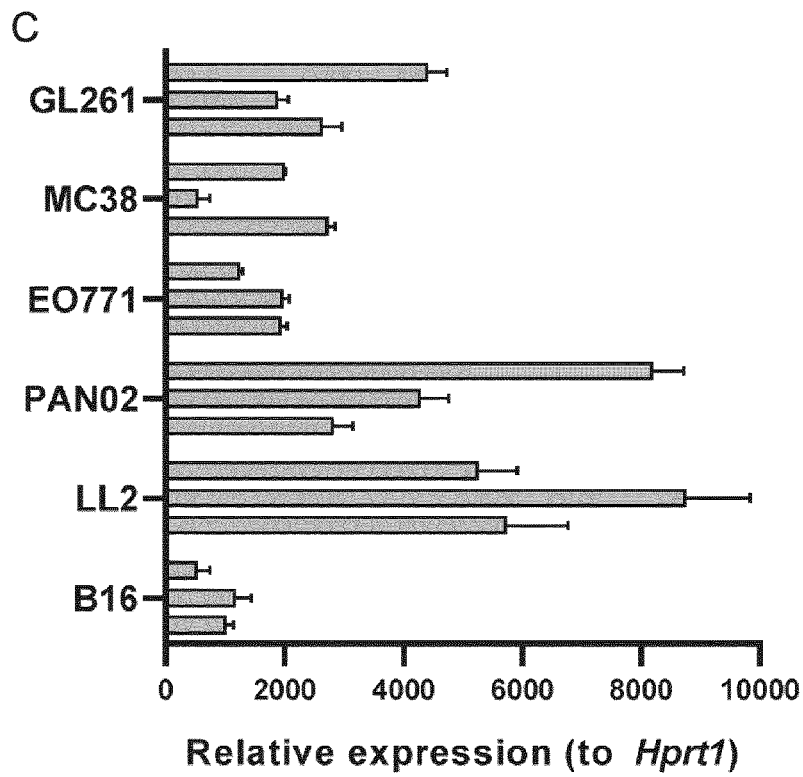
Figure 20:
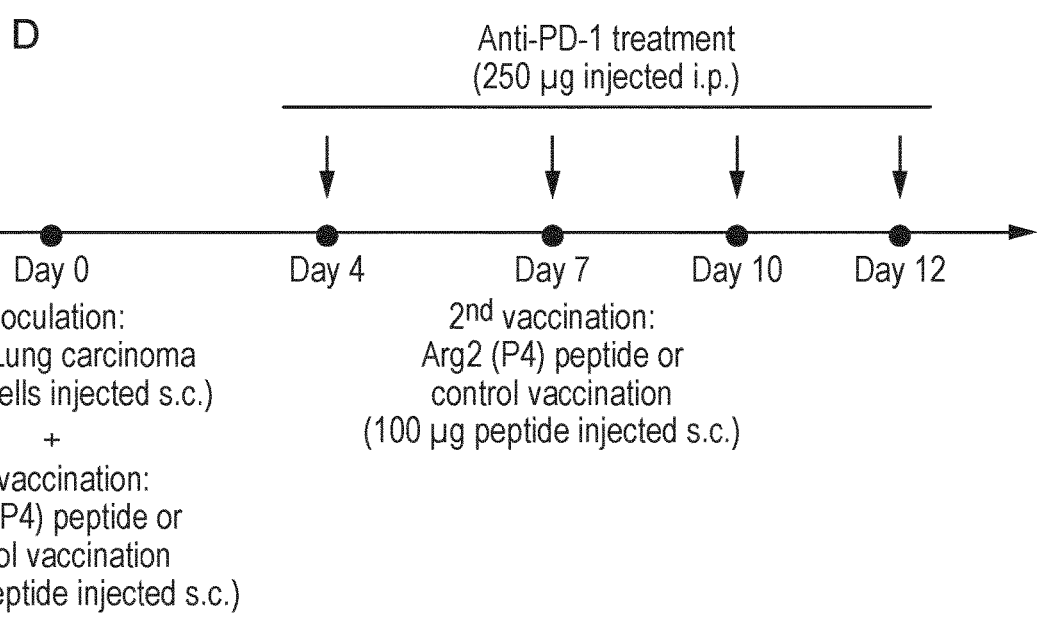
Figure 20:
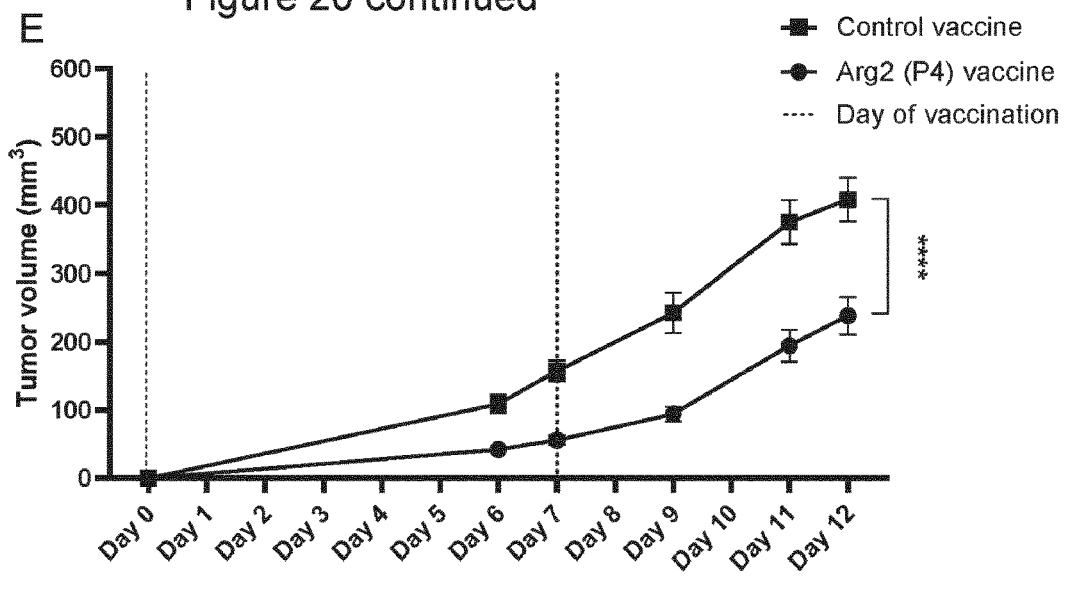
Figure 20:
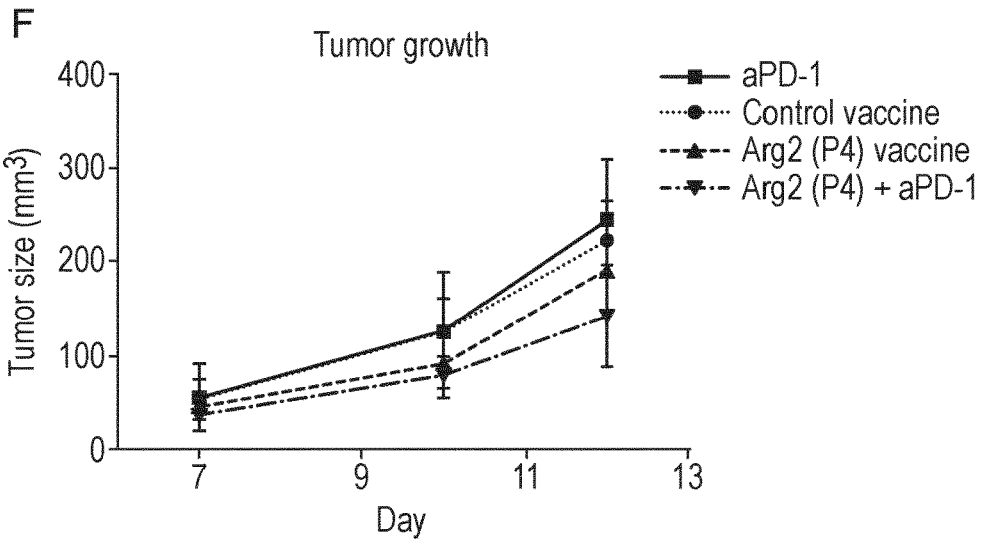
Figure 20:
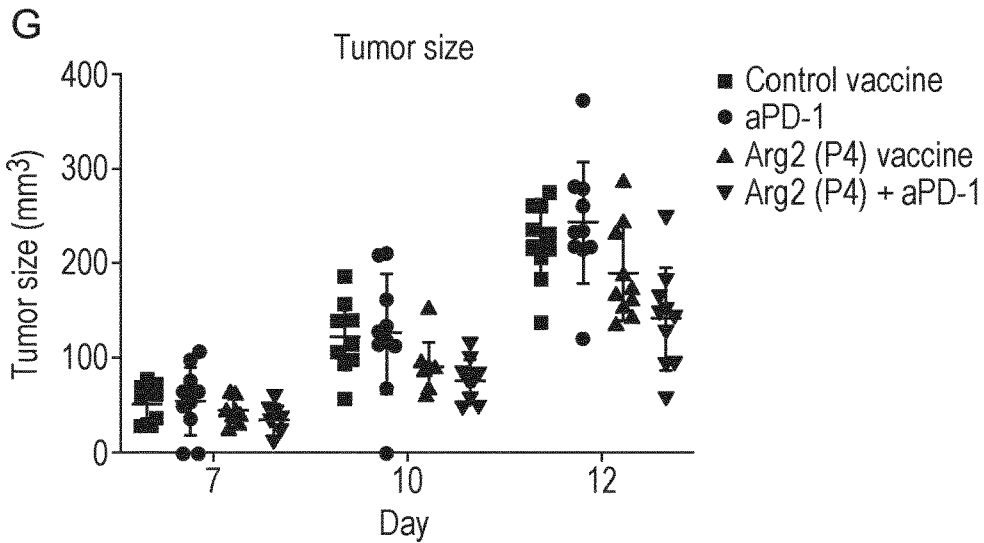

Examples 1 and 2 show ARG2 as a target for specific T cells in vitro where both immune cells and cancer cells expressing ARG2 are specifically recognized by ARG2-specific T cells. To examine a potential functional effect of ARG2-specific T cells in vivo, Example 3 identified relevant murine Arg2 peptide epitopes which were evaluated further. C57BL/6 mice were screened for immune responses by s.c. vaccination of mice in a peptide-Montanide™ emulsion. Three mice per group were vaccinated with each of the 6 candidate peptides and 7 days later mice were sacrificed, splenocytes were isolated and analyzed in an ex vivo mIFNy ELISPOT assay. Strong immune responses were observed in all 3 mice vaccinated with P4 (see FIG. 12, plus the same data is also presented in FIG. 20A). This was subsequently confirmed in a similar experiment with more mice per group (FIG. 20B).

To identify the most relevant tumor model, Arg2 expression was evaluated in a panel of different engrafted tumors of C57BL/6 origin. We found the most consistent high expression of Arg2 in tumors formed by Lewis Lung (LL2) tumor cells (FIG. 20C). Challenge of C57BL/6 mice with LL2 tumor cells followed by two vaccinations (day 0 and day 7 after tumor inoculation—see treatment schedule in FIG. 2D) caused a decreased tumor growth in Arg2 vaccinated mice (P4) compared to mock vaccinated control group (Ctrl) (FIG. 20E). Mice were sacrificed at day 12 after tumor inoculation due to ulcer formation on tumors. To examine if Arg2 vaccination could modify the TME in a manner that could induce effect of anti-PD1 antibodies, we combined vaccination against mARG2(188-197) (denoted P4) with anti-PD1 in the LL2 model. As expected, monotherapy with anti-PD1 antibody did not affect tumor growth in this model. However, the combination of anti-PD1 with ARG2 vaccination had an additive effect (FIGS. 20F and G). Mice were sacrificed at day 12 after tumor inoculation due to ulcer formation on tumors.

Overall Summary and Discussion of Examples 1-4

The Examples have shown that ARG2 is the target of specific T-cells and thus that specific ARG2-specific effector T cells could be exploited as a possible novel means of targeting ARG2-expressing immunosuppressive cells. Firstly, the Examples identified peripheral ARG2-specific T cells that were naturally present in both cancer patients and healthy donors by screening a peptide library covering the entire ARG2 sequence. Interestingly, it was discovered that ARG2 contained multiple epitopes that were frequently recognized by peripheral T cells. The frequent T-cell responses against ARG2 underline the high immunogenicity of ARG2, and supports the likelihood of boosting an ARG2-specific immune response patient with ARG2 expressing cancers, e.g., patients with prostate cancer or AML. Furthermore, strong immune responses in healthy individuals suggest that ARG2-specific T cells are a natural part of the immune system and may be important for immune homeostasis. Additionally specific CD4+ T cells were isolated and expanded that reacted to peptides derived from the apparently most immunogenic region of ARG2. The results demonstrate that ARG2-specific T cells indeed recognize and react to ARG2 expressing myeloid cells.

In general, tumors are now divided into different categories depending on immune infiltration; (i) a scarce immune infiltrate (in so-called 'cold' tumors); (ii) an immune infiltrate precluded from getting in contact with malignant cells (in so-called 'excluded' tumors); or (iii) an abundant tumor infiltrate (in so-called 'hot' tumors) that is held in check by robust immunosuppressive mechanisms. An important therapeutic strategy is clinical combinations that convert 'cold' and 'excluded' tumors into 'hot' tumors, because the latter are generally associated with improved disease outcome on immunotherapy, especially checkpoint blockade. An important characteristic of Arginase is its expression in the 'excluded' tumor types due to arginase-expressing immune-suppressive immune cells in these tumors. It is well described that ARG1 is upregulated in M2-like macrophages in response to Th2 cytokines such as IL-4 and IL-13 in addition to IL-10 and TGF-β. In contrast, the regulation of ARG2 is only very limited described, but interestingly it has been suggested that Toll-like receptor ligands such as lipopolysaccharide and oligodeoxynucleotides containing high amounts of unmethylated cytosine guanine motifs (CpG) induce ARG2 expression in murine macrophages.

It was furthermore recently described that IL113 and TNFa induced ARG2 in neuroblastoma cells. Importantly, in the present study, we further show that a mixture of cytokines, i.e. IL4, GM-CSF and TNF-α induce ARG2 in malignant myeloid cells. Hence, ARG2 seems to be induced by environments present not only in excluded tumors but also in the more 'intermediate' to 'hot' tumors. Thus, as the microenvironments in which ARG1 or ARG2 are induced differ, it is no surprise that ARG1 and ARG2 are found to be expressed by different cells and in different tumor types in the tumor microenvironment (TME). Hence, whereas ARG1 is expressed mainly by MDSCs and TAMs, ARG2 has been described expressed by various solid tumor cells, AML blasts and CAFs. Therefore, the combination of ARG1 and ARG2 for vaccination might be beneficial to target different immunosuppressive Arginase-expressing cells in the TME, which could benefit more patients. Furthermore, it is well described that activated M1 macrophages that propagate inflammation arise in response to Th1 cytokines such as IFNγ. Importantly, many stroma cells are not terminally differentiated cells and may be reverted into immunocompetent cells given a pro-inflammatory stimulus. Activation of Arginase-specific T-cells by e.g. vaccination should indeed cause Th1 inflammation at the tumor site. It is known that other types of anti-regulatory T cells exist, e.g. IDO- and PD-L1 specific pro-inflammatory T cells and it has been reported that Th1-inflammation signals, e.g. IFNγ, spontaneously lead to the expansion of such IDO- and PD-L1 specific T cells, suggesting the potential synergistic action of Arginase with IDO- or PDLL-based vaccines. In this scenario, ARG1/ARG2 vaccination could induce Th1 inflammation at tumor sites, where Arginase expressing cells otherwise prevent lymphocyte infiltration. In turn, this effect would induce IDO and/or PD-L1, enabling further targeting by anti-Tregs recognizing epitopes derived from these targets. Thus, the combination of epitopes from different anti-Treg target antigens could be additive in a vaccination approach. Likewise, combination therapy with ARG2 immune modulatory vaccines that activate ARG2-specific T cells and checkpoint blocking antibodies should increase the number of patients who could respond to therapy in comparison with checkpoint blockade alone, which works only in inflamed tumors. Hence, Arginase-expressing cells prevent effector lymphocyte proliferation at the tumor site and are therefore an important reason for the lack of effect of anti-PD1 therapy in many patients with cancer. In the current study, we show that ARG2 is indeed expressed in the well-described PD-L1 resistant tumor model Lewis Lung. We show that the activation of ARG2-specific T cells by vaccination inhibits Lewis lung cell growth of and, most importantly, function synergistically with anti-PD1. Thus, combination with immune modulatory ARG2 vaccination may indeed make the resistant Lewis Lung cells susceptible for anti-PD1 therapy.

Overall the Examples show that ARG2 specific T cells exist as a natural part of the immune system and can be readily employed to tilt the balance away from immune suppression in cancer. Therapeutic vaccination against ARG2 should promote the generation of an inflammatory TME that would favor cancer-specific immune responses against cancer cells. It is therefore likely that an ARG2 based vaccine would function synergistically with additional immunotherapy especially checkpoint inhibitors. The most immunogenic peptide from human ARG2 used in the Examples is efficient at stimulating ARG2-specific T-cell responses which may be vital for rebalancing of the microenvironment and should increase the effect of T-cell-enhancing drugs such as checkpoint blockers in comparison to single approach therapies or current cancer vaccines that only aim to target cancer cells.

SEQUENCES

Start pos and End pos indicate the positions within full length human Arginase 2 (SEQ ID NO: 51) unless otherwise indicated.

TABLE X

| SEQ ID NO | Sequence | Name | Start pos | End pos |
|---|---|---|---|---|
| 1 | MSLRGSLSRLLQTRVHSILK | ARG2_0 | 1 | 20 |
| 2 | LQTRVHSILKKSVHSVAVIG | ARG2_1 | 11 | 30 |
| 3 | KSVHSVAVIGAPFSQGQKRK | ARG2_2 | 21 | 40 |
| 4 | APFSQGQKRKGVEHGPAAIR | ARG2_3 | 31 | 50 |
| 5 | GVEHGPAAIREAGLMKRLSS | ARG2_4 | 41 | 60 |
| 6 | EAGLMKRLSSLGCHLKDFGD | ARG2_5 | 51 | 70 |
| 7 | LGCHLKDFGDLSFTPVPKDD | ARG2_6 | 61 | 80 |
| 8 | LSFTPVPKDDLYNNLIVNPR | ARG2_7 | 71 | 90 |
| 9 | LYNNLIVNPRSVGLANQELA | ARG2_8 | 81 | 100 |
| 10 | SVGLANQELAEVVSRAVSDG | ARG2_9 | 91 | 110 |
| 11 | EVVSRAVSDGYSCVTLGGDH | ARG2_10 | 101 | 120 |
| 12 | YSCVTLGGDHSLAIGTISGH | ARG2_11 | 111 | 130 |
| 13 | SLAIGTISGHARHCPDLCVV | ARG2_12 | 121 | 140 |
| 14 | ARHCPDLCVVWVDAHADINT | ARG2_13 | 131 | 150 |
| 15 | WVDAHADINTPLTTSSGNLH | ARG2_14 | 141 | 160 |
| 16 | PLTTSSGNLHGQPVSFLLRE | ARG2_15 | 151 | 170 |
| 17 | GQPVSFLLRELQDKVPQLPG | ARG2_16 | 161 | 180 |
| 18 | LQDKVPQLPGFSWIKPCISS | ARG2_17 | 171 | 190 |
| 19 | FSWIKPCISSASIVYIGLRD | ARG2_18 | 181 | 200 |
| 20 | ASIVYIGLRDVDPPEHFILK | ARG2_19 | 191 | 210 |
| 21 | VDPPEHFILKNYDIQYFSMR | ARG2_20 | 201 | 220 |
| 22 | NYDIQYFSMRDIDRLGIQKV | ARG2_21 | 211 | 230 |
| 23 | DIDRLGIQKVMERTFDLLIG | ARG2_22 | 221 | 240 |
| 24 | MERTFDLLIGKRQRPIHLSF | ARG2_23 | 231 | 250 |
| 25 | KRQRPIHLSFDIDAFDPTLA | ARG2_24 | 241 | 260 |
| 26 | DIDAFDPTLAPATGTPVVGG | ARG2_25 | 251 | 270 |
| 27 | PATGTPVVGGLTYREGMYIA | ARG2_26 | 261 | 280 |
| 28 | LTYREGMYIAEEIHNTGLLS | ARG2_27 | 271 | 290 |
| 29 | EEIHNTGLLSALDLVEVNPQ | ARG2_28 | 281 | 300 |
| 30 | ALDLVEVNPQLATSEEEAKT | ARG2_29 | 291 | 310 |
| 31 | LATSEEEAKTTANLAVDVIA | ARG2_30 | 301 | 320 |
| 32 | TANLAVDVIASSFGQTREGG | ARG2_31 | 311 | 330 |
| 33 | SSFGQTREGGHIVYDQLPTP | ARG2_32 | 321 | 340 |

TABLE X-continued

| SEQ ID NO | Sequence | Name | Start pos | End pos |
|---|---|---|---|---|
| 34 | HIVYDQLPTPSSPDESENQARVRI | ARG2_33 | 331 | 354 |
| 35 | GFSWIKPCISSASIVYIGLR | ARG2-E17 | 180 | 199 |
| 36 | SASIVYIGLRDVDPPEHFIL | ARG2-E18 | 190 | 209 |
| 37 | DVDPPEHFILKNYDIQYFSM | ARG2-E19 | 200 | 219 |
| 38 | KNYDIQYFSMRDIDRLGIQK | ARG2-E20 | 210 | 229 |
| 39 | GFSWIKPCISSASIVYIGLRDVDPPEHFILKNYDIQYFSMRDIDRLGIQK | Hotspot | 180 | 229 |
| 40 | GFSWVTPCISAKDIVYIGLRDVDPGEHYILKTLGIKYFSMTEVDRLGIGK* | Hotspot | 161 | 210 |
| 41 | GFSWVTPCISAKDIVYIGLR* | Arg-17 | 161 | 180 |
| 42 | AKDIVYIGLRDVDPGEHYIL* | Arg-18 | 171 | 190 |
| 43 | DVDPGEHYILKTLGIKYFSM* | Arg-19 | 181 | 200 |
| 44 | KTLGIKYFSMTEVDRLGIGK* | Arg-20 | 191 | 210 |
| 45 | VVYPRSVGL# | mArg2 P1 | 85 | 93 |
| 46 | VVYPRSVGLANQELAEVV# | mArg2 P2 | 85 | 102 |
| 47 | PNIVYIGL# | mArg2 P3 | 191 | 198 |
| 48 | WIKPCLSPPNIVYIGL# | mArg2 P4 | 182 | 197 |
| 49 | LSPPNIVYI# | mArg2 P5 | 188 | 196 |
| 50 | IQYFSMREI# | mArg2 P6 | 213 | 221 |
| 51 | Full length human Arg2-see below table | | | |
| 52 | Full length murine Arg2-see below table | | | |
| 53 | Full length human Arg1-see below table | | | |
| 54 | ILKKSVHSVA | | 18 | 27 |
| 55 | ILKKSVHSV | | 18 | 26 |
| 56 | SILKKSVHSV | | 17 | 26 |
| 57 | SLSRLLQTRVHSILKKSVHSVAVIGAPFS | A2L3 | 6 | 34 |
| 58 | SLRGSLSRLLQTRVHSILKKSVHSVAVIGA | A2L1 | 2 | 31 |
| 59 | SLRGSLSRLLQTRVHSILKKSVHSVAVIGAPFS | A2L2 | 2 | 34 |
| 60 | FSWIKPCISSASIVYIGLRDVDPPEHFIL | | 181 | 209 |
| 61 | LPGFSWIKPCISSASIVYIGLRDVDPPEHFIL | | 178 | 209 |
| 62 | MSLRGSLSRLLQTRVHSILKKS | Signal sequence | 1 | 22 |

TABLE X-continued

| SEQ ID NO | Sequence | Name | Start pos | End pos |
|---|---|---|---|---|
| 63 | MSLRGSLSRLLQTRVHSILKKSVHSVAVIGAPF SQGQKRKGVEHGPAAIREAGLMK | N terminus incl signal | 1 | 56 |
| 64 | MSAKSRTIGIIGAPFSKGQPRGGVEEGPTVLRK AGLLE* | N terminus for comparison | 1 | 38 |

*indicates a sequence from human Arginase1. Start and end positions are the positions in human Arginase 1 (SEQ ID NO: 53).

indicates a sequence from murine Arginase2. Start and end positions are the positions in murine Arginase2 (SEQ ID NO: 52), although since the murine and human proteins are identical in length, the numbering also matches human Arginase2

Full length human Arginase 2 (NP_001163.1)(SEQ ID NO: 51)
MSLRGSLSRL LQTRVHSILK *KSV*HSVAVIG APFSQGQKRK GVEHGPAAIR EAGLMKRLSS
LGCHLKDFGD LSFTPVPKDD LYNNLIVNPR SVGLANQELA EVVSRAVSDG YSCVTMGGDH
SLAIGTISGH ARHCPDLCVV WVDAHADINT PLTTSSGNLH GQPVSFLLRE LQDKVPQLPG
FSWIKPCISS ASIVYIGLRD VDPPEHFILK NYDIQYFSMR DIDRLGIQKV MERTFDLLIG
KRQRPIHLSF DIDAFDPTLA PATGTPVVGG LTYREGMYIA EEIHNTGLLS ALDLVEVNPQ
LATSEEEAKT TANLAVDVIA SSFGQTREGG HIVYDQLPTP SSPDESENQA RVRI Region identified as a hotspot for immunogenicity based on Arginase 1 homology is shown bold and underlined. The transit peptide boundary identified as the centre of a previously unappreciated hotspot is shown bold and italic "KSV".

Full length murine Arginase 2 (NP_033835.1) (SEQ ID NO: 52)
MFLRSSASRL LHGQIPCVLT RSVHSVAIVG APFSRGQKKL GVEYGPAAIR EAGLLKRLSR
LGCHLKDFGD LSFTNVPQDD PYNNLVVYPR SVGLANQELA EVVSRAVSGG YSCVTMGGDH
SLAIGTIIGH ARHRPDLCVI WVDAHADINT PLTTVSGNIH GQPLSFLIKE LQDKVPQLPG
FSWIKPCLSP PNIVYIGLRD VEPPEHFILK NYDIQYFSMR EIDRLGIQKV MEQTFDRLIG
KRQRPIHLSF DIDAFDPKLA PATGTPVVGG LTYREGVYIT EEIHNTGLLS ALDLVEVNPH
LATSEEEAKA TARLAVDVIA SSFGQTREGG HIVYDHLPTP SSPHESENEE CVRI Full length human Arginase 1 (NP_000036.2) (SEQ ID NO: 53)
MSAKSRTIGI IGAPFSKGQP RGGVEEGPTV LRKAGLLEKL KEQECDVKDY GDLPFADIPN
DSPFQIVKNP RSVGKASEQL AGKVAEVKKN GRISLVLGGD HSLAIGSISG HARVHPDLGV
IWVDAHTDIN TPLTTTSGNL HGQPVSFLLK ELKGKIPDVP **GFSWVTPCIS AKDIVYIGLR
DVDPGEHYIL KTLGIKYFSM TEVDRLGIGK** VMEETLSYLL GRKKRPIHLS FDVDGLDPSF
TPATGTPVVG GLTYREGLYI TEEIYKTGLL SGLDIMEVNP SLGKTPEEVT RTVNTAVAIT
LACFGLAREG NHKPIDYLNP PK
Region identified as a hotspot for immunogenicity shown bold and underlined

---

The invention claimed is:

1. A composition comprising a polypeptide which is animmunogenic fragment of human Arginase2 (SEQ ID NO: 51) that comprises or consists of a sequence of at least 9 consecutive amino acids of SEQ ID NO: 51 which includes at least the amino acids at positions 21, 22 and 23 of SEQ ID NO: 51, wherein the polypeptide has a maximum length of 50 amino acids and an adjuvant.

2. The composition of claim 1 which comprises or consists of up to 15, 20, 25, 30, 35, 40, 45 or 50 consecutive amino acids of SEQ ID NO: 51.

3. The composition of claim 1 which comprises or consists of the amino acid sequence of any one of SEQ ID NOs: 59, 58, 57, 54, 55, 56, 2 or 3.

4. The composition of claim 1, which has a maximum length of 10, 15, 20, 25, 30, 35, 40 or 45 amino acids and/or in which the C terminal amino acid is replaced with the corresponding amide.

5. The composition according to claim 1, comprising at least one pharmaceutically acceptable diluent, carrier or preservative.

6. The composition according to claim 1 wherein the adjuvant is selected from the group consisting of bacterial DNA based adjuvants, oil/surfactant based adjuvants, viral dsRNA based adjuvants, and imidazoquinolines.

7. The composition according to claim 5, wherein the oil/surfactant based adjuvant is a water-in-oil (W/O) emulsion composed of a mineral oil and a surfactant from the mannide monooleate family.

* * * * *

UNITED STATES PATENT AND TRADEMARK OFFICE
CERTIFICATE OF CORRECTION

| | | |
|---|---|---|
| PATENT NO. | : 12,234,288 B2 | Page 1 of 1 |
| APPLICATION NO. | : 17/293325 | |
| DATED | : February 25, 2025 | |
| INVENTOR(S) | : Mads Hald Andersen | |

It is certified that error appears in the above-identified patent and that said Letters Patent is hereby corrected as shown below:

In the Claims

At Column 65, Claim number 1, Line number 24:
"animmunogenic" should read --an immunogenic--

At Column 66, Claim number 7, Line number 32:
"claim 5" should read --claim 6--

Signed and Sealed this
Twenty-second Day of April, 2025

Coke Morgan Stewart
*Acting Director of the United States Patent and Trademark Office*